(12) United States Patent
Griffis

(10) Patent No.: US 12,202,662 B2
(45) Date of Patent: Jan. 21, 2025

(54) SCENT DELIVERY AND PRESERVATION SYSTEMS AND METHODS FOR BEVERAGE CONTAINERS

(71) Applicant: Szent Co., La Jolla, CA (US)

(72) Inventor: Shawn Griffis, La Jolla, CA (US)

(73) Assignee: Szent Co., La Jolla, CA (US)

( * ) Notice: Subject to any disclaimer, the term of this patent is extended or adjusted under 35 U.S.C. 154(b) by 0 days.

(21) Appl. No.: 18/185,357

(22) Filed: Mar. 16, 2023

(65) Prior Publication Data

US 2024/0051717 A1 Feb. 15, 2024

Related U.S. Application Data

(63) Continuation of application No. 17/396,121, filed on Aug. 6, 2021, now Pat. No. 11,613,415, which is a
(Continued)

(51) Int. Cl.
*B65D 51/28* (2006.01)
*A61L 9/12* (2006.01)

(52) U.S. Cl.
CPC .............. *B65D 51/28* (2013.01); *A61L 9/12* (2013.01); *A61L 2209/13* (2013.01)

(58) Field of Classification Search
CPC .. B65D 51/28; B65D 1/28; A61L 9/12; A61L 2209/13
(Continued)

(56) References Cited

U.S. PATENT DOCUMENTS

D25,131 S  2/1896 Fowler, Jr.
D28,746 S  5/1898 Blount
(Continued)

FOREIGN PATENT DOCUMENTS

CN  201694464 U  1/2011
CN  104172723 A  12/2014
(Continued)

OTHER PUBLICATIONS

Etsy. Mini Orange Plastic Soda Bottle Rings/Safety Seals. Mar. 23, 2018 [earliest online date], [site visited Apr. 23, 18]. Available from Internet, <URL:https://etsy.me/2HSzu7f>. (Year: 2018).
(Continued)

*Primary Examiner* — J. Gregory Pickett
*Assistant Examiner* — Niki M Eloshway
(74) *Attorney, Agent, or Firm* — Perkins Coie LLP

(57) ABSTRACT

Disclosed are devices, systems and methods for controlling scent delivery by a scented article for beverage containers. In some aspects, a scent delivery system includes a cap attachable to a beverage container; and a scented article that couples to the cap, wherein the cap comprises a base, a movable component coupled to the base and able to move between a first position and a second position, and a scent chamber including an encasement to which the scented article is attached, the encasement coupled to the movable component or the base, wherein a portion of the scented article is exposed to air from an outside environment with respect to the cap when the movable component is in the second position, and wherein the encasement creates a contact seal to enclose the scented article within the scent chamber and lock in the scent when the movable component is in the first position.

19 Claims, 29 Drawing Sheets

Related U.S. Application Data continuation of application No. 16/428,737, filed on May 31, 2019, now Pat. No. 11,097,877.

(60) Provisional application No. 62/678,808, filed on May 31, 2018.

(58) Field of Classification Search
USPC ........................................ 220/212, 714, 717
See application file for complete search history.

(56) References Cited

U.S. PATENT DOCUMENTS

| | | |
|---|---|---|
| D30,094 S | 1/1899 | Busch |
| D30,338 S | 3/1899 | Mann |
| D31,451 S | 8/1899 | Norris |
| D32,681 S | 5/1900 | Morgenthaler |
| D44,392 S | 7/1912 | Whitney |
| D54,241 S | 12/1919 | Christian |
| 1,695,822 A | 12/1928 | Restein |
| D99,688 S | 5/1936 | Tomlinson |
| D101,242 S | 9/1936 | Poglein |
| D138,198 S | 7/1944 | Jackson |
| D159,985 S | 9/1950 | Heisey |
| D172,090 S | 5/1954 | Pree |
| 2,830,721 A | 4/1958 | Pinsky et al. |
| 3,043,464 A | 3/1959 | Cerasari |
| 2,922,454 A | 1/1960 | Vossloh |
| D191,418 S | 9/1961 | Nassour |
| D206,889 S | 2/1967 | Benes |
| D209,311 S | 11/1967 | Schilling |
| 3,405,828 A | 10/1968 | St. Pierre |
| 3,409,181 A | 11/1968 | McDonnell |
| D212,843 S | 12/1968 | Hart et al. |
| 3,414,183 A | 12/1968 | Wilcox |
| 3,432,177 A | 3/1969 | Colwell |
| D215,417 S | 9/1969 | MacDonald |
| 3,464,576 A | 9/1969 | Rohde |
| 3,590,989 A | 7/1971 | Wittwer |
| D221,625 S | 8/1971 | Kinney et al. |
| D230,187 S | 1/1974 | Schultz |
| D242,200 S | 11/1976 | Ashton et al. |
| D243,406 S | 2/1977 | Mooney et al. |
| D251,650 S | 4/1979 | Heller |
| D252,373 S | 7/1979 | Eisenrod |
| D256,003 S | 7/1980 | Barr |
| D256,046 S | 7/1980 | Perrin |
| D258,202 S | 2/1981 | Astor et al. |
| D272,213 S | 1/1984 | Daenen |
| 4,540,721 A | 9/1985 | Staller |
| D285,778 S | 9/1986 | Smith |
| D288,902 S | 3/1987 | Lewis |
| 4,687,203 A | 8/1987 | Spector |
| 4,717,017 A | 1/1988 | Sprinkel et al. |
| D303,915 S | 10/1989 | Knutson |
| D305,310 S | 1/1990 | Flinchbaugh |
| 4,969,570 A | 11/1990 | Harvey, Sr. |
| D312,768 S | 12/1990 | Eastman |
| 4,981,230 A | 1/1991 | Marshall et al. |
| D315,309 S | 3/1991 | Baughman |
| D317,274 S | 6/1991 | Redina |
| D319,035 S | 8/1991 | Kruse |
| 5,165,603 A * | 11/1992 | Hahn ................. A45D 40/0068 |
| | | 206/823 |
| 5,197,620 A | 3/1993 | Gregory |
| 5,249,676 A | 10/1993 | Ashcraft et al. |
| D344,763 S | 3/1994 | Vitantonio |
| D348,836 S | 7/1994 | McCallum et al. |
| D354,681 S | 1/1995 | Nolte |
| D355,708 S | 2/1995 | Caine |
| 5,388,731 A | 2/1995 | Mengeu et al. |
| D358,988 S | 6/1995 | Nolte |
| 5,477,640 A | 12/1995 | Holtkamp, Jr. |
| D367,818 S | 3/1996 | Zana |
| D372,765 S | 8/1996 | Sisk |
| D374,837 S | 10/1996 | Austin |
| 5,582,308 A | 12/1996 | Kishi et al. |
| 5,588,562 A | 12/1996 | Sander et al. |
| 5,635,229 A * | 6/1997 | Ray ........................ B65D 23/12 |
| | | 426/115 |
| D383,677 S | 9/1997 | Darr et al. |
| 5,707,696 A | 1/1998 | Boxler |
| D390,111 S | 2/1998 | Mccarrick |
| D390,461 S | 2/1998 | Piselli |
| D391,628 S | 3/1998 | Carwile |
| D394,824 S | 6/1998 | Itzkowitz |
| 5,785,240 A | 7/1998 | Showler |
| 5,795,644 A | 8/1998 | Delarosa |
| 5,806,242 A | 9/1998 | Park |
| 5,810,184 A | 9/1998 | Adams et al. |
| 5,858,141 A | 1/1999 | Repp et al. |
| 5,865,535 A | 2/1999 | Edwards |
| 5,913,437 A | 6/1999 | Ma |
| D412,281 S | 7/1999 | Lindsay |
| 5,954,247 A | 9/1999 | Savine |
| 5,957,312 A | 9/1999 | Adams et al. |
| 6,006,472 A * | 12/1999 | Holtkamp, Jr. ......... A01G 27/04 |
| | | 47/79 |
| D418,414 S | 1/2000 | Cheng |
| D422,905 S | 4/2000 | Walker |
| 6,045,833 A * | 4/2000 | Landau .................. B65D 51/00 |
| | | 426/106 |
| D424,948 S | 5/2000 | Ullmo |
| 6,062,441 A | 5/2000 | Mengeu et al. |
| 6,102,224 A | 8/2000 | Sun |
| 6,112,749 A | 9/2000 | Hall et al. |
| 6,112,923 A | 9/2000 | Ma |
| D438,050 S | 2/2001 | Huntzinger |
| D441,650 S | 5/2001 | Salzburg |
| 6,290,914 B1 | 9/2001 | LeJune et al. |
| D449,556 S | 10/2001 | Pasquetti |
| D453,000 S | 1/2002 | Shinjo |
| D457,245 S | 5/2002 | Royal et al. |
| D457,783 S | 5/2002 | Bodum |
| D460,357 S | 7/2002 | Kras et al. |
| D465,731 S | 11/2002 | Brant et al. |
| 6,484,873 B1 | 11/2002 | Pizarro |
| 6,484,896 B2 | 11/2002 | Ma |
| 6,497,337 B1 | 12/2002 | Kehe |
| D468,492 S | 1/2003 | Wilhelm |
| 6,511,726 B1 | 1/2003 | Kinigakis |
| D470,057 S | 2/2003 | Bowen |
| 6,581,793 B1 | 6/2003 | Racine et al. |
| D476,893 S | 7/2003 | Pinnavaia |
| D477,225 S | 7/2003 | Pinnavaia |
| D482,562 S | 11/2003 | Demers |
| D482,794 S | 11/2003 | Whitley |
| D483,982 S | 12/2003 | Irvine |
| 6,659,297 B2 | 12/2003 | Gregory et al. |
| D485,126 S | 1/2004 | Watson |
| 6,677,397 B1 | 1/2004 | Baranowski et al. |
| D491,066 S | 6/2004 | Le Goff |
| 6,766,916 B2 | 7/2004 | Ma |
| D498,826 S | 11/2004 | Takahiro et al. |
| D501,625 S | 2/2005 | Biggerstaff |
| 6,964,346 B1 | 11/2005 | Taber et al. |
| D512,914 S | 12/2005 | Moretti |
| 6,981,602 B2 | 1/2006 | Ma et al. |
| D515,353 S | 2/2006 | Martin |
| 7,005,152 B2 | 2/2006 | Landau |
| D518,717 S | 4/2006 | German |
| D518,718 S | 4/2006 | vonSpreckelsen et al. |
| D522,368 S | 6/2006 | Darr et al. |
| D533,747 S | 12/2006 | Jin |
| D533,802 S | 12/2006 | Thompson et al. |
| D534,428 S | 1/2007 | Reed et al. |
| D534,802 S | 1/2007 | German |
| D535,210 S | 1/2007 | Park |
| D545,235 S | 6/2007 | Carter-Smith et al. |
| D546,225 S | 7/2007 | Brown |
| D546,226 S | 7/2007 | Brown |
| D546,227 S | 7/2007 | Brown |
| D548,092 S | 8/2007 | Klemm |
| D553,238 S | 10/2007 | Haggkvist |
| D553,254 S | 10/2007 | Colin et al. |

(56) References Cited

U.S. PATENT DOCUMENTS

| | | | | |
|---|---|---|---|---|
| 7,284,711 B2 | * | 10/2007 | Reed | A61L 9/12 239/289 |
| 7,306,108 B2 | | 12/2007 | Cleevely | |
| D561,595 S | | 2/2008 | Le Bras-Brown | |
| D564,711 S | | 3/2008 | Modi et al. | |
| D565,253 S | | 3/2008 | Modi et al. | |
| D571,214 S | | 6/2008 | Cazatt | |
| D575,154 S | | 8/2008 | Andrews | |
| D576,047 S | | 9/2008 | Reihle | |
| D578,889 S | | 10/2008 | Sadiq et al. | |
| 7,470,035 B1 | | 12/2008 | Benitez | |
| D584,149 S | | 1/2009 | Lohrman et al. | |
| D584,632 S | | 1/2009 | Lloyd | |
| D587,118 S | | 2/2009 | Sadiq et al. | |
| 7,484,675 B2 | | 2/2009 | Brown | |
| D591,603 S | | 5/2009 | Robin-Prevallee | |
| D592,950 S | | 5/2009 | Kopulos | |
| D593,858 S | | 6/2009 | Kubicek et al. | |
| D595,581 S | | 7/2009 | Brunson | |
| D598,238 S | | 8/2009 | Durdon et al. | |
| D600,115 S | * | 9/2009 | Trayser | D9/434 |
| D601,309 S | | 9/2009 | Babal | |
| D602,651 S | | 10/2009 | Modi et al. | |
| RE41,055 E | | 12/2009 | Choke-arpornchai | |
| D606,864 S | | 12/2009 | Robinson | |
| D607,091 S | | 12/2009 | Weston | |
| D610,011 S | | 2/2010 | De Pieretti | |
| D611,814 S | | 3/2010 | Marotti et al. | |
| D611,822 S | | 3/2010 | Rajani | |
| D614,247 S | | 4/2010 | Clausen | |
| D614,271 S | | 4/2010 | Weston | |
| D615,816 S | | 5/2010 | Joy et al. | |
| D617,426 S | | 6/2010 | Zeyfang | |
| D618,500 S | | 6/2010 | Hardaway | |
| 7,748,557 B2 | | 7/2010 | Robinson | |
| D621,266 S | | 8/2010 | Smith | |
| D622,600 S | | 8/2010 | Bradfield | |
| D623,056 S | | 9/2010 | Sessa | |
| D623,460 S | | 9/2010 | Krasner | |
| 7,798,320 B2 | * | 9/2010 | Pham | B65D 65/42 229/87.13 |
| D625,183 S | | 10/2010 | Bartsch | |
| D633,386 S | | 3/2011 | Taber et al. | |
| D633,387 S | | 3/2011 | Gatto | |
| D634,199 S | | 3/2011 | Taber et al. | |
| D634,200 S | | 3/2011 | Taber et al. | |
| D635,352 S | | 4/2011 | Himley et al. | |
| D635,399 S | | 4/2011 | DelVecchio | |
| D637,448 S | | 5/2011 | Cheng | |
| D643,729 S | | 8/2011 | Lovelace, Jr. | |
| D643,912 S | | 8/2011 | Bowman | |
| D646,568 S | | 10/2011 | Heidel et al. | |
| D646,600 S | | 10/2011 | Minkkinen et al. | |
| D650,677 S | | 12/2011 | Wurster et al. | |
| D654,752 S | | 2/2012 | Krasner | |
| D655,167 S | | 3/2012 | Weber-Trinkfass et al. | |
| D657,675 S | | 4/2012 | Averill | |
| D662,767 S | | 7/2012 | Hotell et al. | |
| D666,461 S | | 9/2012 | Siegel | |
| D669,781 S | | 10/2012 | Fields | |
| D671,406 S | | 11/2012 | Sawicki et al. | |
| 8,364,028 B1 | | 1/2013 | Vaske et al. | |
| D678,989 S | | 3/2013 | Zerrer | |
| D679,598 S | | 4/2013 | Miceli | |
| D679,999 S | | 4/2013 | Miceli | |
| 8,440,265 B2 | | 5/2013 | Duan | |
| D684,065 S | | 6/2013 | Wiseman | |
| D684,082 S | | 6/2013 | Alvarez et al. | |
| D684,274 S | | 6/2013 | Hosoya et al. | |
| D686,075 S | | 7/2013 | Guerin et al. | |
| D686,081 S | | 7/2013 | Colangelo | |
| D686,101 S | | 7/2013 | Dailey | |
| 8,474,637 B2 | | 7/2013 | Zhang et al. | |
| D689,332 S | | 9/2013 | Krasner | |
| D689,789 S | | 9/2013 | Hardy | |
| D690,218 S | | 9/2013 | Cobbett | |
| D691,885 S | | 10/2013 | Potts | |
| D693,645 S | | 11/2013 | Keyes | |
| D694,107 S | | 11/2013 | Didio | |
| D696,751 S | | 12/2013 | Beagen, Jr. | |
| D696,952 S | | 1/2014 | Sawicki et al. | |
| D697,805 S | | 1/2014 | You | |
| 8,672,158 B2 | | 3/2014 | Taber | |
| 8,708,189 B2 | | 4/2014 | Reitzig | |
| D704,088 S | | 5/2014 | Farris | |
| D706,908 S | | 6/2014 | Knapp | |
| D706,909 S | | 6/2014 | van de Klippe et al. | |
| D715,092 S | | 10/2014 | Thun et al. | |
| 8,881,988 B2 | | 11/2014 | Miceli | |
| D723,919 S | | 3/2015 | Taber et al. | |
| D724,386 S | | 3/2015 | Royer et al. | |
| D725,953 S | | 4/2015 | Gamelli et al. | |
| D726,006 S | | 4/2015 | Rapparini | |
| D728,757 S | | 5/2015 | Graham | |
| D730,734 S | | 6/2015 | Rapparini | |
| D733,604 S | | 7/2015 | Tan et al. | |
| D734,670 S | * | 7/2015 | Griffis | D9/452 |
| 9,108,763 B2 | * | 8/2015 | Landau | B65D 25/00 |
| D743,255 S | | 11/2015 | Niggemyer | |
| D743,513 S | | 11/2015 | Yamagishi et al. | |
| D744,846 S | | 12/2015 | Koop et al. | |
| D752,378 S | | 3/2016 | Wang | |
| D752,975 S | | 4/2016 | Gatto | |
| D753,490 S | | 4/2016 | O'Donahue | |
| 9,302,830 B2 | | 4/2016 | Ramsey et al. | |
| D756,228 S | | 5/2016 | Premkumar | |
| D758,195 S | | 6/2016 | Braz et al. | |
| D762,115 S | | 7/2016 | Corvaglia et al. | |
| D766,716 S | | 9/2016 | Logel et al. | |
| 9,452,859 B2 | | 9/2016 | Franic | |
| D776,529 S | | 1/2017 | Torrison et al. | |
| D778,199 S | | 2/2017 | Amfitheatrof | |
| D779,941 S | | 2/2017 | Koga | |
| D783,406 S | | 4/2017 | Melrose | |
| D783,607 S | | 4/2017 | Lee et al. | |
| D784,182 S | | 4/2017 | Baker | |
| D785,144 S | | 4/2017 | Kitagawa | |
| D788,587 S | | 6/2017 | Clemence | |
| D789,232 S | | 6/2017 | Baker | |
| D791,591 S | | 7/2017 | Berge | |
| D792,219 S | | 7/2017 | Bueno Nunez | |
| D793,237 S | | 8/2017 | Vitale Rotta | |
| D795,021 S | | 8/2017 | Lindloff | |
| D796,901 S | | 9/2017 | Pisarevsky | |
| D799,900 S | | 10/2017 | Santos et al. | |
| D799,963 S | | 10/2017 | Akiyama | |
| 9,777,244 B2 | | 10/2017 | Lei | |
| 9,801,969 B2 | | 10/2017 | Griffis | |
| D804,305 S | | 12/2017 | White | |
| D804,306 S | | 12/2017 | Simons | |
| D804,900 S | | 12/2017 | Choe | |
| D804,906 S | | 12/2017 | Diener et al. | |
| D807,173 S | * | 1/2018 | Cooper | D9/452 |
| D807,749 S | | 1/2018 | Beaver | |
| D808,810 S | | 1/2018 | Rajesh | |
| D809,923 S | | 2/2018 | Marantis | |
| D810,504 S | | 2/2018 | Goodwin | |
| D815,951 S | | 4/2018 | Solovy | |
| D817,096 S | | 5/2018 | Kauss et al. | |
| 9,957,076 B2 | | 5/2018 | Tung | |
| D820,679 S | | 6/2018 | Ali | |
| D821,150 S | | 6/2018 | Liao | |
| D824,257 S | | 7/2018 | Wood et al. | |
| D824,264 S | | 7/2018 | Toribio | |
| D824,763 S | | 8/2018 | Suess et al. | |
| D826,047 S | * | 8/2018 | Griffis | D9/454 |
| D827,435 S | * | 9/2018 | Griffis | D9/454 |
| D828,088 S | | 9/2018 | Furneaux et al. | |
| D829,101 S | | 9/2018 | Spivey et al. | |
| D830,773 S | | 10/2018 | Jacobsen | |
| D832,105 S | | 10/2018 | Clemence | |
| D832,130 S | | 10/2018 | Bostic | |
| 10,086,104 B2 | * | 10/2018 | Griffis | H05K 999/99 |
| D832,734 S | | 11/2018 | Warren | |

(56) References Cited

U.S. PATENT DOCUMENTS

| | | | |
|---|---|---|---|
| D833,293 S | 11/2018 | Lin | |
| D836,389 S | 12/2018 | Abante et al. | |
| D837,052 S | 1/2019 | Rapparini | |
| D837,054 S | 1/2019 | Mallahan, III | |
| D838,171 S | 1/2019 | Wood et al. | |
| 10,189,611 B2 * | 1/2019 | Cox | B65D 47/0804 |
| D839,673 S | 2/2019 | Meyers | |
| D842,030 S | 3/2019 | Meyers | |
| D844,433 S | 4/2019 | Hall et al. | |
| D846,095 S | 4/2019 | Copeland | |
| D846,096 S | 4/2019 | Copeland | |
| D846,097 S | 4/2019 | Copeland | |
| D846,098 S | 4/2019 | Copeland | |
| 10,252,842 B2 | 4/2019 | Miceli | |
| D848,844 S | 5/2019 | Byron et al. | |
| D851,996 S | 6/2019 | Umholtz | |
| D852,335 S | 6/2019 | Copeland | |
| D852,336 S | 6/2019 | Copeland | |
| 10,328,172 B2 * | 6/2019 | Griffis | B65D 41/34 |
| D852,634 S | 7/2019 | Balletta et al. | |
| D852,935 S | 7/2019 | Copeland | |
| D855,464 S | 8/2019 | Hall et al. | |
| D857,859 S | 8/2019 | Copeland | |
| D858,903 S | 9/2019 | Jennings | |
| D873,142 S | 1/2020 | Jones | |
| D875,525 S | 2/2020 | Griffis | |
| D875,899 S | 2/2020 | Yoshida | |
| D875,900 S | 2/2020 | Yoshida | |
| D876,236 S | 2/2020 | Griffis | |
| D884,479 S | 5/2020 | Hall | |
| D884,540 S | 5/2020 | Tse | |
| D885,906 S | 6/2020 | Griffis | |
| D885,962 S | 6/2020 | Jones | |
| D885,963 S | 6/2020 | Riviere | |
| D891,287 S | 7/2020 | Fort, Jr. | |
| D891,967 S | 8/2020 | Fort, Jr. | |
| D891,970 S | 8/2020 | Fort, Jr. | |
| D891,971 S | 8/2020 | Fort, Jr. | |
| 10,744,223 B2 | 8/2020 | Griffis | |
| D895,777 S | 9/2020 | Chase | |
| D896,679 S | 9/2020 | Lachyani Abiri | |
| D901,306 S | 11/2020 | Clark | |
| D905,559 S | 12/2020 | Ungrady | |
| 10,864,293 B2 | 12/2020 | Griffis | |
| D909,186 S | 2/2021 | Wang | |
| D911,208 S | 2/2021 | Tysander | |
| D911,846 S | 3/2021 | Van Den Heijkant | |
| D913,140 S | 3/2021 | Grace | |
| D917,963 S | 5/2021 | Ozturk | |
| D919,469 S | 5/2021 | Fort, Jr. | |
| 11,097,877 B2 | 8/2021 | Griffis | |
| D931,105 S | 9/2021 | Griffis | |
| D931,688 S | 9/2021 | Wang | |
| D934,102 S | 10/2021 | Barnes | |
| D939,352 S | 12/2021 | Kelley | |
| D943,449 S | 2/2022 | Yang | |
| D944,679 S | 3/2022 | Lopez | |
| D946,449 S | 3/2022 | Mclear | |
| D947,056 S | 3/2022 | Choo | |
| D947,707 S | 4/2022 | Mclear | |
| 11,312,528 B2 | 4/2022 | Griffis | |
| D950,384 S | 5/2022 | Griffis | |
| 11,357,881 B2 | 6/2022 | Griffis | |
| 11,389,557 B2 | 7/2022 | Griffis | |
| D966,105 S | 10/2022 | Cronk | |
| D966,892 S | 10/2022 | Cornehl | |
| D971,724 S | 12/2022 | Stevenson | |
| 11,613,415 B2 | 3/2023 | Griffis | |
| D982,443 S | 4/2023 | Graux | |
| 11,628,989 B2 | 4/2023 | Sanchez | |
| 11,724,853 B2 | 8/2023 | Griffis | |
| 2001/0027957 A1 | 10/2001 | Kano et al. | |
| 2002/0139093 A1 | 10/2002 | Landau | |
| 2002/0158037 A1 | 10/2002 | Kano et al. | |
| 2002/0190023 A1 * | 12/2002 | Landau | A47G 19/2227 215/387 |
| 2003/0132244 A1 | 7/2003 | Birkmayer et al. | |
| 2004/0018278 A1 | 1/2004 | Popplewell | |
| 2004/0020890 A1 | 2/2004 | Tan et al. | |
| 2004/0029750 A1 | 2/2004 | Schudel et al. | |
| 2004/0262174 A1 | 12/2004 | Buesching et al. | |
| 2005/0142084 A1 | 6/2005 | Ganguly | |
| 2005/0196571 A1 | 9/2005 | Penny et al. | |
| 2005/0274819 A1 * | 12/2005 | Reed | A61L 9/12 239/57 |
| 2006/0144912 A1 | 7/2006 | Franic | |
| 2006/0246265 A1 | 11/2006 | Rogers et al. | |
| 2006/0255002 A1 | 11/2006 | Takamatsu et al. | |
| 2006/0278542 A1 | 12/2006 | Pham et al. | |
| 2006/0278543 A1 | 12/2006 | Pham | |
| 2006/0291756 A1 | 12/2006 | Thomas et al. | |
| 2007/0023301 A1 | 2/2007 | Pham | |
| 2007/0051690 A1 | 3/2007 | Hidding | |
| 2007/0114142 A1 | 5/2007 | Sine et al. | |
| 2008/0067142 A1 | 3/2008 | Druitt | |
| 2008/0149586 A1 | 6/2008 | Loughrin et al. | |
| 2008/0173611 A1 | 7/2008 | Neputy et al. | |
| 2008/0245757 A1 | 10/2008 | Durand | |
| 2009/0045158 A1 | 2/2009 | Suriol | |
| 2009/0078786 A1 | 3/2009 | Slade | |
| 2009/0098026 A1 | 4/2009 | Wood | |
| 2009/0155505 A1 | 6/2009 | Wagenheim | |
| 2009/0258118 A1 | 10/2009 | Gillian | |
| 2010/0084362 A1 | 4/2010 | Letchinger et al. | |
| 2010/0323134 A1 | 12/2010 | Bostian et al. | |
| 2011/0253584 A1 | 10/2011 | Duan | |
| 2011/0290755 A1 | 12/2011 | Taber et al. | |
| 2012/0006909 A1 * | 1/2012 | Zhang | A23L 2/56 239/34 |
| 2012/0175016 A1 | 7/2012 | Lopez et al. | |
| 2013/0015193 A1 | 1/2013 | Lien et al. | |
| 2013/0043245 A1 * | 2/2013 | Griffis | B65D 41/34 239/34 |
| 2013/0056551 A1 | 3/2013 | Zhang et al. | |
| 2013/0062239 A1 | 3/2013 | Key | |
| 2013/0105066 A1 * | 5/2013 | Landau | B65D 81/3453 427/256 |
| 2013/0119056 A1 | 5/2013 | Jacobson et al. | |
| 2013/0205718 A1 | 8/2013 | Kapolas | |
| 2013/0221007 A1 | 8/2013 | Jung et al. | |
| 2013/0276339 A1 | 10/2013 | Hernandez et al. | |
| 2013/0313218 A1 | 11/2013 | Cox et al. | |
| 2014/0158660 A1 | 6/2014 | Wood et al. | |
| 2014/0263335 A1 | 9/2014 | Taber et al. | |
| 2015/0027974 A1 | 1/2015 | Niec | |
| 2015/0076030 A1 | 3/2015 | Smith | |
| 2015/0102033 A1 | 4/2015 | Banovie | |
| 2015/0305349 A1 | 10/2015 | Johnson et al. | |
| 2015/0329247 A1 | 11/2015 | Lou | |
| 2015/0366250 A1 * | 12/2015 | Landau | A23L 2/56 426/2 |
| 2015/0375906 A1 | 12/2015 | Vieker | |
| 2016/0106149 A1 | 4/2016 | Potter et al. | |
| 2016/0122066 A1 | 5/2016 | DiBaisio | |
| 2017/0081095 A1 | 3/2017 | Mcpherson et al. | |
| 2017/0239382 A1 * | 8/2017 | Griffis | B65D 51/24 |
| 2017/0240325 A1 | 8/2017 | Seelhofer | |
| 2017/0275075 A1 | 9/2017 | Bamonte et al. | |
| 2017/0326263 A1 | 11/2017 | Griffis | |
| 2017/0370505 A1 | 12/2017 | Copeland | |
| 2018/0043047 A1 | 2/2018 | Griffis | |
| 2018/0079552 A1 | 3/2018 | Ayeni | |
| 2018/0127159 A1 * | 5/2018 | Cunningham | B65D 51/2807 |
| 2018/0141730 A1 | 5/2018 | Rognard | |
| 2018/0201414 A1 | 7/2018 | Rouquette | |
| 2019/0009953 A1 | 1/2019 | Edie et al. | |
| 2019/0062007 A1 | 2/2019 | Kim | |
| 2019/0084728 A1 | 3/2019 | Bonfoey et al. | |
| 2019/0091363 A1 | 3/2019 | Griffis | |
| 2019/0118989 A1 | 4/2019 | Kim | |
| 2019/0224359 A1 * | 7/2019 | Griffis | B29B 9/16 |
| 2019/0367230 A1 * | 12/2019 | Griffis | A61L 9/12 |
| 2022/0347334 A1 * | 11/2022 | Hsu | A61L 9/122 |

(56) References Cited

U.S. PATENT DOCUMENTS

| | | | |
|---|---|---|---|
| 2023/0060282 A1 | 3/2023 | Griffis | |
| 2023/0126929 A1 | 4/2023 | Joseph | |
| 2023/0227224 A1 | 7/2023 | Bobb | |

FOREIGN PATENT DOCUMENTS

| | | |
|---|---|---|
| CN | 104495736 A | 4/2015 |
| DE | 102006038257 A1 | 2/2008 |
| DE | 102009020524 A1 | 11/2010 |
| DE | 202017001221 U1 | 7/2017 |
| GB | 5000214 | 10/2015 |
| GB | 9005826559-0006 | 11/2018 |
| GB | 9005826559-0007 | 11/2018 |
| GB | 2569075 A | 6/2019 |
| JP | 06505412 H | 6/1994 |
| JP | 2000085777 A | 3/2000 |
| JP | 2006-168788 A | 6/2006 |
| JP | 2018188221 A | 11/2018 |
| WO | 2010068731 | 6/2010 |
| WO | 2010128149 A1 | 11/2010 |
| WO | 2012006328 A1 | 1/2012 |
| WO | 2013105066 A1 | 7/2013 |
| WO | 2018085580 | 5/2018 |
| WO | 2018203993 | 11/2018 |
| WO | 2019232431 | 12/2019 |

OTHER PUBLICATIONS

First Action Interview Pilot Program Pre-Interview Communication for U.S. Appl. No. 15/782,720, mailed Apr. 2, 2018 (6 pages).
Flavour Bottle: The world's first flavored bottle, available at https://www.kickstarter.com/projects/flavourtechnologies/flavour-bottle-the-worlds-first-flavored-bottle/description.
Forever Gifts. Beveled Edge Black Tungsten Wedding Band. Apr. 26, 2017 [earliest online date], [site visited Apr. 26, 2018]. Available from Internet, <URL:https://www.forevergifts.com/beveled-edge-black-tungsten-wedding-band-free-engraving/>. (Year: 2017).
High-Tech Cocktail Glass Lets You Experience Plain Water as the Perfect Cocktail, Oddity Central, available at http://www.odditycentral.com/technology/high-tech-cocktail-glass-lets-you-experience-plain-water-as-the-perfect-cocktail.html, Nov. 20, 2017.
International Search Report and Written Opinion for International Application No. PCT/US18/24630, mailed Apr. 23, 2018 (7 pages).
Non-Final Office Action for U.S. Appl. No. 15/663,534, mailed Apr. 2, 2018 (26 pages).
Non-Final Office Action for U.S. Appl. No. 29/598,882, mailed May 1, 2018 (29 pages).
Non-Final Office Action for U.S. Appl. No. 29/598,879, mailed May 1, 2018 (26 pages).
The New York Times. Mystery in Sochi Doping Case Lies With Tamper-Proof Bottle by Rebecca R. Ruiz. May 13, 2016 [earliest online date], [site visited Apr. 23, 18]. Available from Internet, <URL:https://www.nytimes.com/2016/05/14/sports/russia-doping-bottles-olympics-2014.html>. (Year: 2016).
Examination Report received for European Union Design Application No. 005826559; mailed Nov. 28, 2018 (2 pages).
First Examiner's Report received for Canadian Application No. 177508; mailed Jul. 23, 2018 (3 pages).
Non-Final Office Action received for U.S. Appl. No. 15/663,534, mailed Aug. 16, 2018 (26 pages).
First Examiner's Report received for Australian Application No. 2018202261; mailed Aug. 30, 2018 (5 pages).
Office Action for German Application No. 10 2018 003 090.4, mailed Jan. 15, 2019 (8 pages).
Examiner's Report received for Canadian Application No. 2999583; mailed Jan. 30, 2019 (3 pages).
Final Office Action received for U.S. Appl. No. 15/663,534; mailed Feb. 13, 2019 (19 pages).
Non-Final Office Action received for U.S. Appl. No. 29/599,447, mailed Mar. 28, 2019 (10 pages).

Szent Water: Announced Nov. 7, 2018 [online]. Site visited [Mar. 22, 2019]. Available from internet URL: https://www.amazon.com/SZE NT-Water-Passionfruit-Ounce-Pack/dp/B07G8 LH B F2/ref=cm_cr_arp_d_product_top?ie= UTF8&th = 1.
Notice of Allowance Received for U.S. Appl. No. 15/663,534, Mailed May 3, 2019.
Notification to Grant Patent Right for Design and Go through Formalities of Registration Received for Chinese Application No. 201830652933.8 Mailed Jul. 16, 2019.
International Search Report and Written Opinion for International Application No. PCT/US19/24708, mailed Jun. 24, 2019 (9 pages).
Notice of Acceptance for Patent Application Received for Australia Application No. 2018202261, mailed May 30, 2019.
Amazon. Szent Water Passionfruit Ounce Pack. Review by Brett Conway on Nov. 9, 2018. hhttps://www.amazon.com/SZENT-Water-Passionfruit-Ounce-Pack/dp/B07G8LHBF2?th=1(Year: 2018).
Amazon. Oxford Ivy—Men's 14K White Gold 6MM Comfort Fit Beveled Edge Wedding Band Sep. 30, 2016. https://www.amazon.com/White-Comfort-Beveled-Wedding-Available/dp/B01LYD52N4 (Year: 2016).
Notice of Allowance Recived for Canadian Application No. 2999583, mailed Aug. 7, 2019.
Non-Final Office Action received for U.S. Appl. No. 16/368,796 mailed Sep. 16, 2019.
International Application No. PCT/US19/34990 International Search Report and Written Opinion, Mailed Oct. 3, 2019.
Final Office Action received for U.S. Appl. No. 29/599,447, mailed Oct. 10, 2019 (26 pages).
Examination Report received for GB 1904947.7; mailed Sep. 3, 2019 (2 pages).
Examination Report received for Canadian Design Application No. 184681; dated Oct. 8, 2019 (44 pages).
Final Office Action received for U.S. Appl. No. 29/599,450; mailed Dec. 11, 2019 (17 pages).
Non-Final Office Action received for U.S. Appl. No. 29/650,568; mailed Dec. 19, 2019 (7 pages).
Non-Final Office Action received for U.S. Appl. No. 29/650,571; mailed Dec. 19, 2019 (10 pages).
Canadian Application No. 2,999,583 Examination Report Mailed Mar. 13, 2020.
U.S. Appl. No. 16/368,796 Notice of Allowance Mailed Apr. 8, 2020. (8 pages).
European Application No. 18794704.9-1104 Extended European Search Report Mailed Jul. 9, 2020, pp. 1-9.
International Application No. PCT/US2019/024708, International Preliminary Report on Patentability Mailed Oct. 8, 2020.
GB Application No. GB2002178.8 Search and Examination Report Mailed Aug. 19, 2020, pp. 1-5.
Ratti Report. A Brand New Kind of Water is Agencyless. Oct. 19, 2018. https://ratti-report.com/industry-food-bev/a-brand-new-kind-of-water-is-agencyless/ (pp. 1-3).
Griffis, Shawn. U.S. Appl. No. 29/707,365, Non-Final Office Action Mailed Oct. 12, 2020, pp. 1-7.
Griffis, Shawn. U.S. Appl. No. 16/428,737 Non-Final Office Action Mailed Nov. 27, 2020 (pp. 1-7).
Chinese Application No. 201911118814.4, First Office Action Mailed Nov. 3, 2020, pages.
U.S. Appl. No. 29/598,879 Notice of Allowance Mailed Apr. 26, 2021, pp. 1-5.
U.S. Appl. No. 29/647,898 Restriction Requirement Mailed Apr. 26, 2021, pp. 1-6.
U.S. Appl. No. 29/647,895 Restriction Requirement Mailed Apr. 26, 2021, pp. 1-5.
Canadian Patent Application No. 2999583 Notice of Allowance Mailed Apr. 20, 2021, pp. 1-14.
U.S. Appl. No. 29/647,905 Non-Final Office Action Mailed Jun. 30, 2021, pp. 1-9.
SKS Bottle & Packaging Tamper Evident Containers, announced Aug. 18, 2011, [online], site visited Jun. 26, 2021. Available from Internet, URL: http://www.sks-bottle.com (Year: 2011).
U.S. Appl. No. 29/647,895 Non-Final Office Action mailed Sep. 2, 2021, pp. 1-7.

(56) References Cited

OTHER PUBLICATIONS

U.S. Appl. No. 29/647,898 Non-Final Office Action Mailed Sep. 2, 2021, pp. 1-11.
U.S. Appl. No. 17/065,342 Non-Final Office Action Mailed Sep. 7, 2021, pp. 1-9.
U.S. Appl. No. 16/944,046 Non-Final Office Action Mailed Sep. 21, 2021, pp. 1-10.
Chinee Application No. 201911118814.4, Second Office Action, Mailed Jul. 1, 2021, pp. 1-5.
European Application No. 19776680.1 Extended European Search Report Mailed Nov. 22, 2021, pp. 1-7.
Chinese Application No. 201911118814.4, Notification of Grant Mailed Jan. 30, 2022, pp. 1-6.
Japanese Application No. 2019-089940 Mailed Jan. 28, 2022, pp. 1-11.
U.S. Patent & Trademark Office, Notice of Allowance for U.S. Appl. No. 17/396,121, mailed Nov. 23, 2022, 8 pages.
U.S. Patent & Trademark Office, Non-Final Office Action for U.S. Appl. No. 17/806,623, mailed Mar. 13, 2023, 9 pages.
Design U.S. Appl. No. 29/808,087, Non-Final Office Action Mailed Nov. 22, 2022, pp. 1-6.
Well + Good. Boosted Waters Are Here to Pep You up, Chill You Out, and Hydrate You to the Fullest. Oct. 23, 2018. https://www.wellandgood.com/hydration-extra-benefits/ (Year: 2018).
United States Patent & Trademark Office, Restriction Requirement, Design U.S. Appl. No. 29/693,869 Mailed Mar. 24, 2023, pp. 1-6.
Food Navigator USA "Beverage Startup SZE NT to enter physical retail: Szent is changing what it means to be a flavored beverage" (online) posted by Mary Ellen Shoup on Feb. 19, 2019. Retrieved from Internet on Mar. 20, 2023, URL: https://www.foodnavigator-USA.com/ Article/2019/02/19/Beverage-startup-SZE NT-to-enter-physical-retai I-SZE NT-is-changing-what-it-means-to-be-a-flavored-beverage (3 pages).
Brazilian Office Action, Office Action for BR Appl. No. BR112019023205-2, mailed Dec. 11, 2022, 3 pages.
U.S. Appl. No. 29/693,869, Ex Parte Quayle Action Mailed Nov. 17, 2023, pp. 1-5.
Silicone Sealing Rings, posted Jul. 16, 2021[retreived Nov. 13, 2023]. Retrieved from internet, https://www.amazon.com/ Replacement-Silicone-Replacements-Seasoning-Insulated/dp/B099N4VFNP/ref (Year: 2021).
Wide Mouth Silicone Sealing Rings Set, posted Apr. 27, 2022 [retrieved Nov. 13, 2023]. Retrieved from internet, https:// www.amazon.com/PA TI KI L-Silicone-Reusable-Leak-Proof-Translucent/dp/B09YY2XPV2/ref (Year: 2022.
Wide Mouth Replacement Gasket, posted Jan. 7, 2019 [retrieved Nov. 13, 2023]. Retrieved from internet, https://www.amazon.com/Bottle-Helpers-Compatible-Replacement-Gasket/dp/B07F3FXP59/ref (Year: 2019).
U.S. Appl. No. 29/695,296, Ex Parte Quayle Action Mailed Oct. 24, 2023, pp. 1-6.
U.S. Appl. No. 17/806,623, Final Office Action dated Dec. 15, 2023.
U.S. Appl. No. 17/806,623, Notice of Allowance dated Jul. 8, 2024.
U.S. Appl. No. 18/185,357, Non Final Office Action dated Jan. 25, 2024.

* cited by examiner

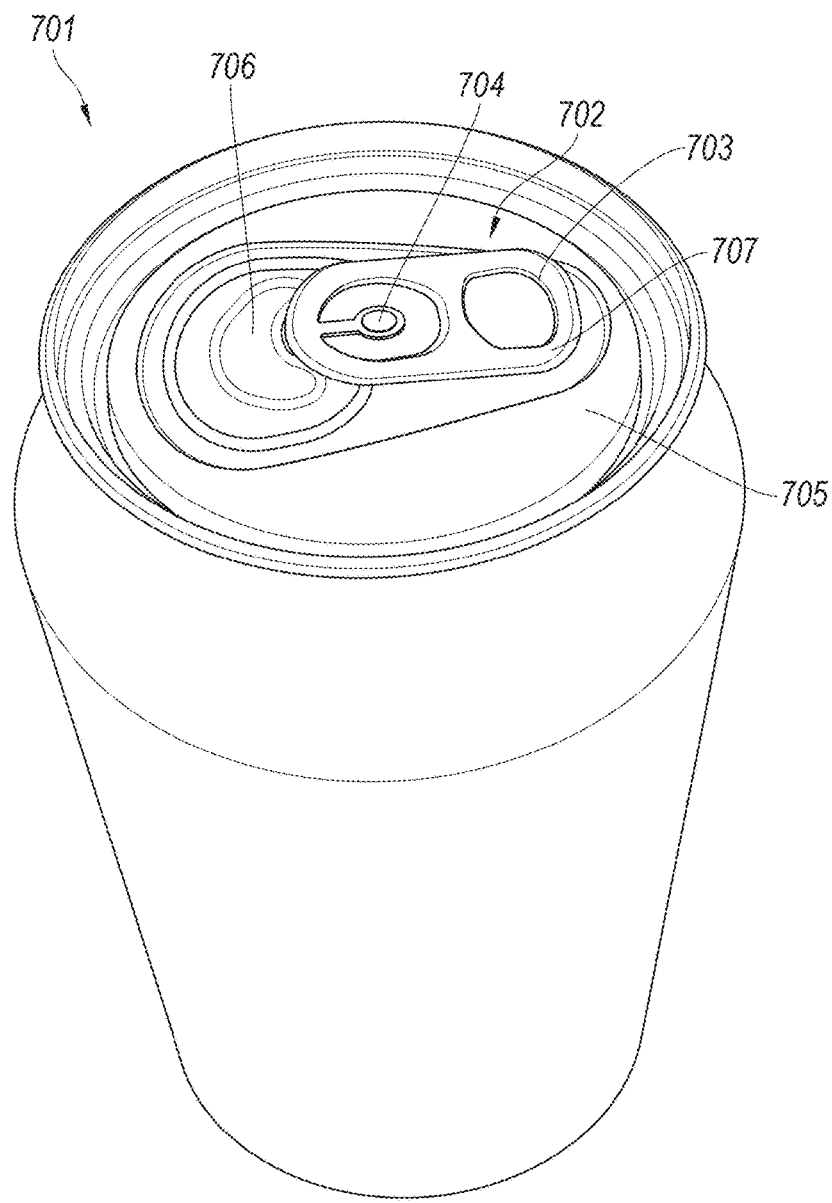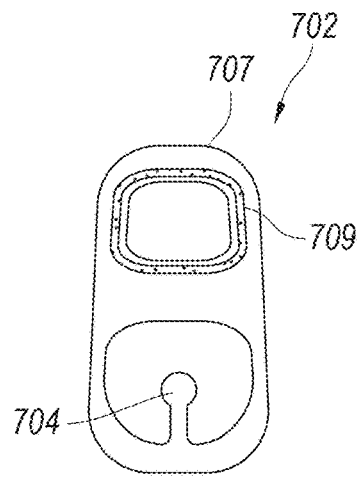
Fig. 7A-1          Fig. 7A-2

SCENT DELIVERY AND PRESERVATION SYSTEMS AND METHODS FOR BEVERAGE CONTAINERS

CROSS-REFERENCE TO RELATED APPLICATIONS

This application is a continuation of U.S. patent application Ser. No. 17/396,121, entitled "SCENT DELIVERY AND PRESERVATION SYSTEMS AND METHODS FOR BEVERAGE CONTAINERS", filed Aug. 6, 2021, now U.S. Pat. No. 11,613,415, which is a continuation of U.S. patent application Ser. No. 16/428,737 entitled "SCENT DELIVERY AND PRESERVATION SYSTEMS AND METHODS FOR BEVERAGE CONTAINERS" filed May 31, 2019, now U.S. Pat. No. 11,097,877, which claims priority to and the benefits of U.S. Provisional Patent Application No. 62/678,808 entitled "SCENT DELIVERY AND PRESERVATION SYSTEMS AND METHODS FOR BEVERAGE CONTAINERS" filed on May 31, 2018. The entire contents of the aforementioned patent applications are incorporated by reference as part of the disclosure of this application.

TECHNICAL FIELD

This patent document relates to techniques, devices and systems for controlling scent delivery by scented articles in beverage containers to enhance a user's sense of smell and/or taste.

BACKGROUND

Fragrance or aroma compounds have been used since antiquity to freshen air and cover odors. One early example includes incense, an aromatic material that forms a fragrant smoke when burned, which is believed to have been used by the ancient Egyptians, Babylonians, and other ancient peoples thousands of years ago. Perfumes were developed over time, having various concentrations of aromatic compounds in a solvent, such as an alcohol. For example, a cologne typically has 3-8% aromatic compound(s) in solvent, whereas an eau de toilette has 5-15% aromatic compound(s) in solvent. By the middle of the twentieth century, fragrance compounds were manufactured into aerosol sprays for air freshener and deodorant products; and decades later, scented materials were developed in products like scented candles.

The nasal cavity has specialized sensory cells that mediate olfaction. The main olfactory system of humans and animals detects volatile chemicals, and the accessory olfactory system detects fluid-phase chemicals. Olfaction like taste is a form of chemoreception. The chemicals that activate the olfactory system, generally at very low concentrations, are called odorants. Accordingly, there is a commonality between the perception of smell and the perception of taste. In fact, in certain instances, the sense of smell may supplement and/or otherwise enhance the sense of taste. For instance, it is well known that maladies affecting the sense of smell adversely affect the sense of taste. As taste plays an important role in one's motivation for consuming a food or drink article, there is an interest in the art for agents that enhance the perception of taste of food and drink articles.

SUMMARY

Disclosed are techniques, devices and systems for controlling scent delivery and/or preserving a scent from a scented article incorporated in a beverage container. In some aspects, the disclosed techniques, devices and systems provide improvements for applying such scented articles to a wide range of different beverage containers in ways that preserve the scented articles' ability to deliver and preserve their scent across multiple uses.

In some embodiments, a scent delivery system includes a cap removably attachable to a drinking container at an opening of the drinking container, the cap including a mechanism to move between an open position that allows fluid within the drinking container to flow outward and a closed position that prevents the fluid to flow outward; and a scented article that couples to the cap and operable to generate a scent capable of stimulating an olfactory sensation of a user including during consumption of the fluid when the cap is in the open position, which, when in the cap is in closed position, a seal is created by the cap to enclose the scented article and lock in the scent.

In some embodiments, a cap for providing a scent delivery system to a beverage container includes a fixed base including a hole through which the beverage can pour; a movable portion mounted on the fixed base so that the movable portion moves between a closed position that seals the hole and an open position that unseals the hole; an attachment assembly including a first inner wall and a first outer wall capable to dispose a scented article between them so that a portion of the scented article is exposed to air when the movable portion is in the open position; and a receiving assembly including a second inner wall and a second outer wall, which, when in the movable portion is in closed position, the first inner wall is in contact with the second inner wall, and the first outer wall is in contact with the second outer wall to create a contact seal around the scented article.

In some embodiments, a scent delivery system includes a lid removably attachable to a drinking container at an opening of the drinking container, the lid including a mechanism to move between an open position that allows fluid within the drinking container to flow outward and a closed position that prevents the fluid to flow outward; and a scented article that couples to the lid and operable to generate a scent capable of stimulating an olfactory sensation of a user including during consumption of the fluid when the mechanism is in the open position, which, when in the mechanism is in closed position, a seal is created to enclose the scented article and lock in the scent.

In some embodiments, a scent delivery system includes a straw removably attachable to a drinking container at an opening of the drinking container, the lid including a mechanism to couple a scented article to the straw and move between an open position that allows a scent to emanate therefrom and a closed position that creates a seal to lock in the scent, which the scent is capable of stimulating an olfactory sensation of a user including during consumption of the fluid when the mechanism is in the open position.

In some embodiments, a scent delivery system for a beverage includes a cap attachable to a beverage container proximate an opening of the beverage container to cover the opening into the beverage container, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a base, a movable component coupled to the base such that the movable component is able to move with respect to the base between a first position and a second position, and a scent chamber including an encasement to which the scented article is attached, the encasement coupled to the movable component or the base, wherein a portion of the scented article is exposed to air from an outside environment with respect to the cap when the movable component is in the second position, and wherein the encasement creates a contact seal to enclose the scented article within the scent chamber and lock in the scent when the movable component is in the first position.

In some embodiments, a scent delivery system for a beverage includes a cap attachable to a beverage container proximate an opening of the beverage container to cover the opening, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a fixed base including a hole through which the liquid can flow out from, a movable component coupled to the fixed base such that the movable component is able to move with respect to the fixed base between a first position to block the hole and put the cap in the closed position and a second position to unblock the hole and put the cap in the open position, and a scent chamber comprising a first encasement and a second encasement, wherein the first encasement includes a first inner wall and a first outer wall that form a first channel between them, wherein the second encasement includes a second inner wall and a second outer wall that form a second channel between them, wherein the first encasement is configured to attach the scented article to one or both of the first inner wall and the first outer wall such that the scented article is disposed in the first channel so that a portion of the scented article is exposed to air when the movable component is in the second position, and wherein the second encasement is positioned to align with the first encasement such that, when the movable component is in first position, (i) the first inner wall is in contact with the second inner wall and (ii) the first outer wall is in contact with the second outer wall to create a contact seal around the scented article, wherein, when the cap is in closed position, the contact seal created by the cap encloses the scented article and locks in the scent.

In some embodiments, a scent delivery system for a beverage includes a cap attachable to a beverage container proximate an opening of the beverage container to cover the opening, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a fixed base including a hole through which the liquid can flow out from, a movable component coupled to the fixed base such that the movable component is able to move with respect to the fixed base between a first position to block the hole and put the cap in the closed position and a second position to unblock the hole and put the cap in the open position, the movable component including a shaft and an outer wall that spans outward and downward such that the movable component forms an enclosable space with the fixed base, such that the enclosable space is enclosed when the movable component is in the first position, and a scent chamber contained within at least a portion of the enclosable space between the movable component and the fixed base, wherein the scented article is attached to the movable component or to the fixed based, such that a portion of the scented article is exposed to air from an outside environment with respect to the cap when the movable component is in the second position, wherein, when the movable component is in first position, the outer wall of the movable component is in contact with the fixed base to create a contact seal to enclose the scented article within the scent chamber and lock in the scent.

In some embodiments, a scent delivery system for a beverage includes a straw removably attachable to a drinking container proximate a hole of the drinking container, the straw operable to allow a liquid contained within the drinking container to flow through the straw and out of an opening of the straw when suction is applied to the opening; and a scented article coupled to an exterior surface of the straw and operable to generate a scent capable of stimulating an olfactory sensation of a user including during consumption of the liquid when the cap is in the open position, the straw including a cover disposed on an outside region of the straw and able to move between a first position that fully covers the scented article and a second position that at least partially exposes the scented article to allow the scent to emanate therefrom.

In some embodiments, a scent delivery system for a beverage includes a pop-top lid attached to a top surface of a beverage container proximate an opening of the beverage container that is initially covered by a cover, the pop-top lid operable to move with respect to the top surface of the beverage container, wherein the pop-top lid is in an initial position when the cover covers the opening, and wherein the pop-top lid is movable to a second position to cause the opening to be at least partially uncovered by the cover; a scented article operable to generate a scent capable of stimulating an olfactory sensation of a user including during consumption of the liquid; and a scent chamber including an encasement to which the scented article is attached, the encasement coupled to the pop-top lid or the top surface of the beverage container, wherein a portion of the scented article is exposed to air from an outside environment with respect to the scent chamber when the pop-top lid has been moved from the initial position to the second position, and wherein the encasement creates an initial contact seal to enclose the scented article within the scent chamber and lock in the scent when the pop-top lid is in the initial position.

The subject matter described in this patent document can be implemented in ways that provide one or more of the following features.

BRIEF DESCRIPTION OF THE DRAWINGS

FIGS. 6A, 6B-1, 6B-2, 6C, and 6D show example embodiments of a scented beverage system including a scented article configured inside a sealable channel of a straw for a drinking container.

FIGS. 7A-1, 7A-2, and 7B-7D show example embodiments of a scented beverage system including a scented article configured to a beverage container, such as a can, utilizing a pop-top lid.

DETAILED DESCRIPTION

Figure 1A:
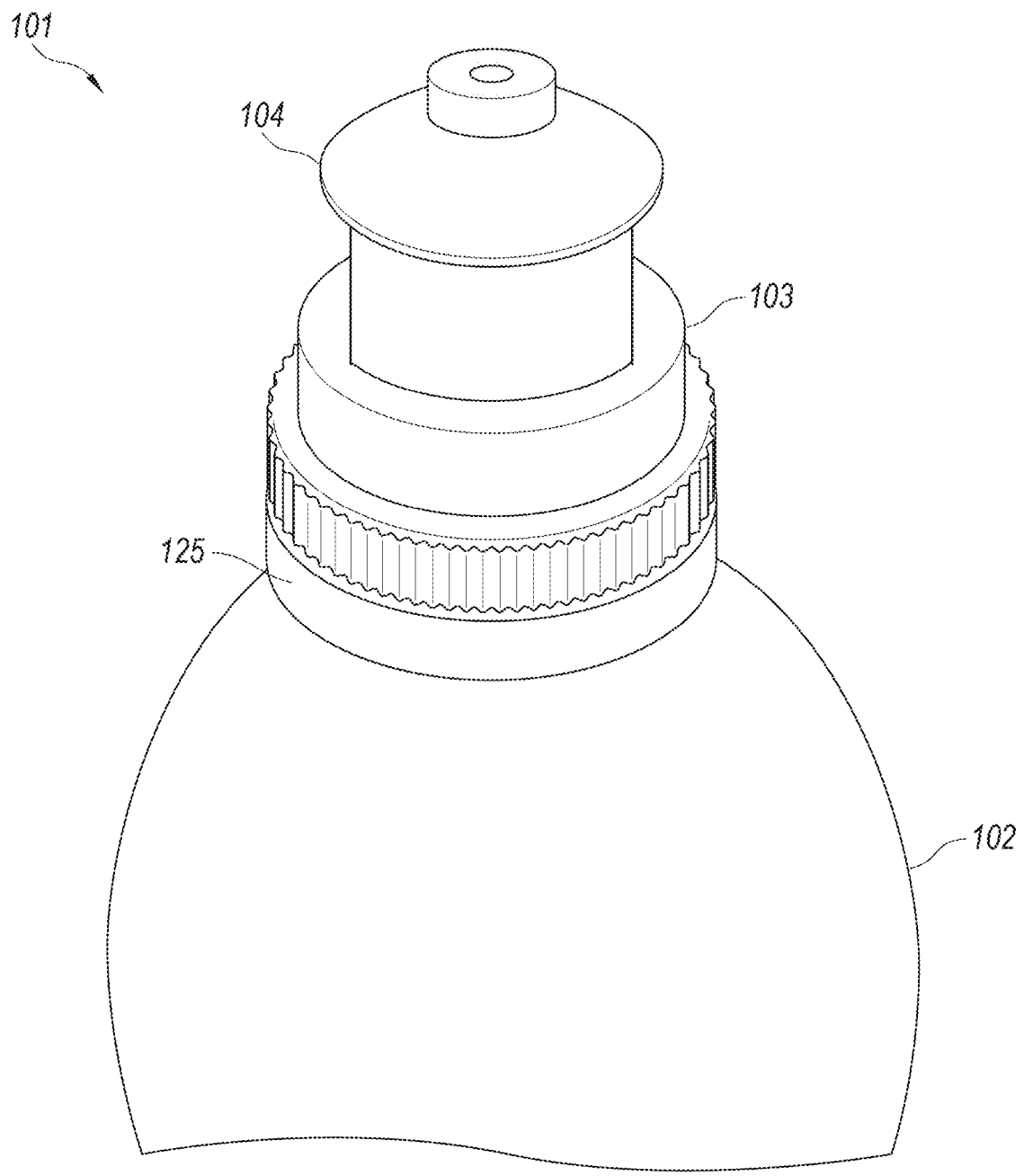
FIGS. 1A-1D show example embodiments of a scented beverage system including a scented article configured inside a sealable channel of a drinking container featuring a nipple-type spout.

For humans, mammals and other living things, the olfactory system detects airborne substances, e.g., volatile chemicals, and provides the living organism with a sense of smell. Olfaction, like taste, is a form of chemoreception. Accordingly, there is a commonality between the perception of smell and the perception of taste. In certain instances, the sense of smell may supplement and/or otherwise enhance the sense of taste, and, for example, maladies affecting the sense of smell adversely affect the sense of taste.

Taste plays an important role in one's motivation for consuming food or drink. As such, food science has spent decades formulating new processed foods and drinks having agents that enhance the perception of taste of food and drink articles. However, more and more studies are showing adverse health effects for some processed foods, which can be due to additives that were used to enhance perception of taste.

Scent-based technologies, such as scented materials and articles, can be used to augment the characteristics of the material or article to affect a person's sense of smell, and thereby sense of taste. For example, a scented material or article may include a chemical agent, such as a fragrance or aroma compound, that stimulates a chemoreceptor of the olfactory system of the subject or otherwise stimulates sense of smell and/or taste of a subject. One example of scent-based technologies includes scented articles that attach or are included as part of a drinking bottle system, in which the scented article provides a pleasing odorant to a user that stimulates a corresponding chemoreceptor of the user's olfactory system to enhance the user's sense of smell and/or taste of a drinkable fluid in the bottle. For example, the scented article can be a lime-scented ring that attaches to the bottle around the bottle opening so that, as the user drinks the beverage within the bottle, such as water, the user experiences a lime-taste to the water from the lime scent that emanates from the scented article while drinking.

Some examples of the scented articles for augmenting a user's perception of taste through smell are described in U.S. Pat. No. 9,801,969B2 entitled "SCENTED ATTACHMENT FOR CONTAINERS", which is incorporated as part of the disclosure in this patent document.

Yet, there are a variety of beverage containers that have different container structures than a typical bottle and that serves different purposes for the user. For example, squeeze bottles can squirt the beverage out from a narrow opening, such as a nipple type spout, that is coverable by a lid. Moreover, there are many variants of tops or caps for squeeze bottles, e.g., which can have different mechanisms for covering or sealing and exposing the opening of the squeeze bottle. Also, for example, some beverage containers include a straw for a user to suck out the beverage from the container portion. Just like with squeeze bottles, there are a plethora of ways to associate or incorporate a straw or straw-like mechanism into the drinking container.

For each type of drinking container design may bring a unique set of challenges to effectively and consistently provide a scented article with the particular drinking container that effectively and reliably delivers the scent during consumption of the beverage to augment the user's drinking experience by a virtual sense of taste perception due to the delivered scent. Some problems are shared by both the structural constraints of the drinking container design and that of the scented article's size, scent concentration, and position configurations with respect to the drinking container. Many conventional scented articles for affecting use of a beverage or other products have failed to effectively augment the user's experience with that product for such reasons.

Disclosed are techniques, devices and systems for controlling scent delivery and/or preserving a scent from a scented article incorporated in a beverage container. In some aspects, the disclosed techniques, devices and systems provide improvements for applying such scented articles to a wide range of different beverage containers in ways that preserve the scented articles' ability to deliver and preserve a consistent scent experience across multiple uses.

Example embodiments of scent delivery systems and methods in accordance with the present technology are described below.

FIGS. 1A-1D show example embodiments of a scented system that can be applied to a cap having a nipple-type spout that is attachable to a beverage container. As shown in FIG. 1A, a beverage container 101 includes a container body 102 that contains a beverage and cap 103 that covers an opening at the mouth of the body 102 to dispense the beverage. Instead of merely presenting an open spout for the consumer to drink from, the cap 103 includes a "nipple-type" spout 104 at an upper region of the cap 103 and attaches to the body 102 at a lower region of the cap 103, e.g., such as by a threading interfacing between a portion of the lower region of the cap 103 and an upper region 125 of the body 102 to allow the lower region of the cap 103 to screw down onto a threaded region at the mouth of body 102. For example, a consumer engaging in activities or sports may prefer a nipple-type spout where the consumer wishes to take periodic sips of beverage but wishes to seal the container when not in use to prevent spillage. Moreover, the nipple-type arrangement allows the consumer to open the spout with their lips or teeth, obviating the need to have a free hand to remove the cap. This again is consistent with consumption of beverages while a consumer is active, since the consumer's hand may be otherwise engaged in the activity. In some embodiments, the beverage container 101 can include an outer cap (not shown) that covers the cap 103, e.g., to protect the spout 104 from contaminants or unwanted contact by other objects.

Figure 1B:
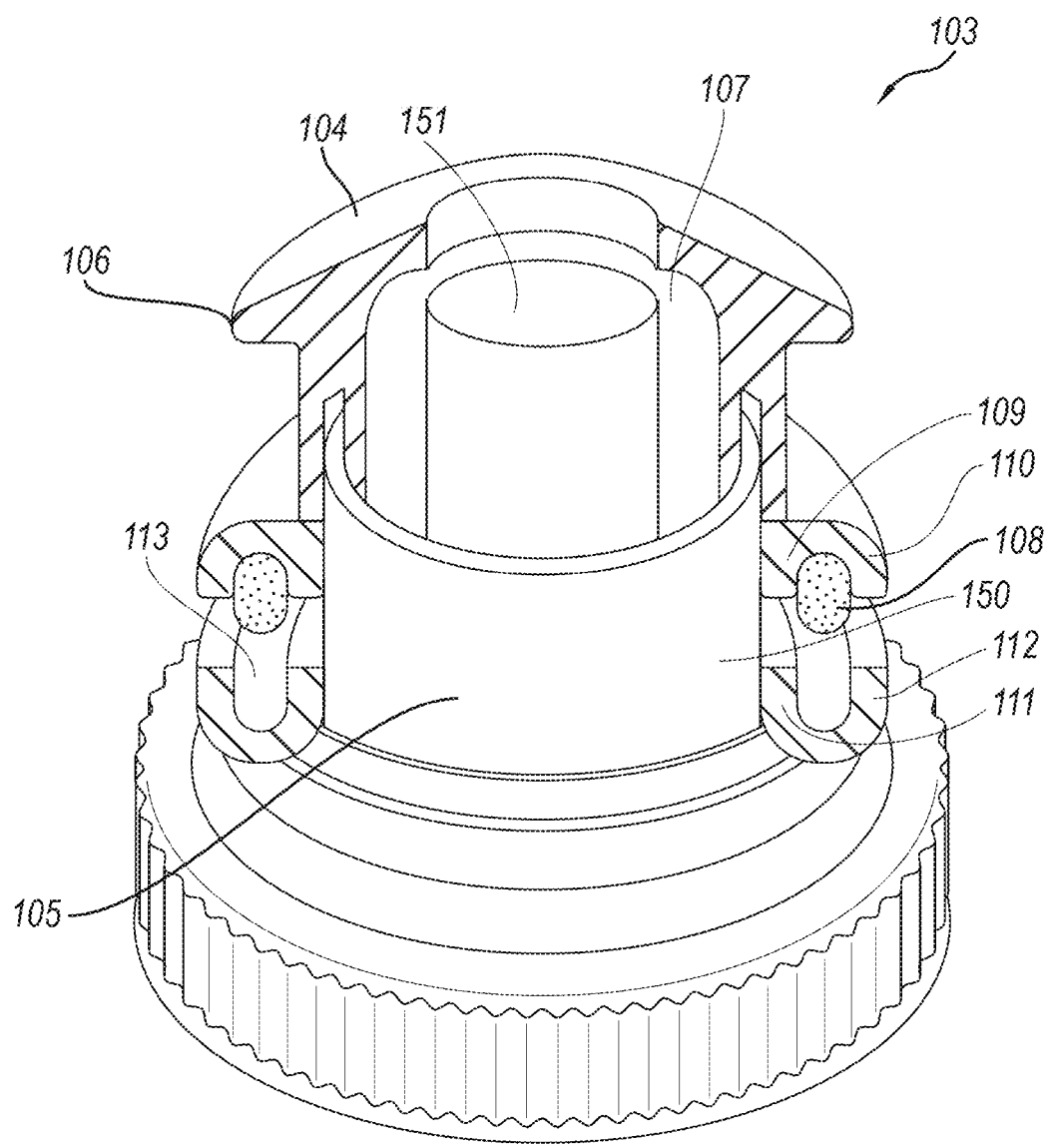

FIG. 1B shows an enlarged, semi-cross-sectional or partially cut-away view of the cap 103 that includes the nipple-type spout 104. Spout 104 includes a fixed base 105 and a movable component or assembly 106 (also referred to as "movable portion" 106), in which the fixed base 105 does not move relative to the lower region of the cap 103, and the movable portion 106 moves relative to the fixed base 105. The fixed base 105 includes a cylinder 150 and a plug 151. In the example shown in the FIG. 1B, movable portion 106 is mounted on cylinder 150 so that it can move bidirectionally relative to fixed base 105, e.g., by sliding up and down; yet, in some embodiments, the movement of movable portion 106 can be accomplished by having movable portion 106 twist along a threaded, screw-like path.

FIG. 1B shows movable portion 106 in its uppermost, or "open" position, exposing channel 107 to allow liquid to flow around plug 151 through an opening of the movable portion of the spout 104. When movable portion 106 is lowered to its lowest, or "closed" position, the flow channel 107 is blocked by plug 151 and liquid cannot flow. For example, in the "closed" position, the upper surface of the plug 151 can substantially align with the upper, outer surface of the movable portion 106, e.g., preventing spillage or leakage of the beverage out of the spout 104 of the cap 103.

In the present examples of the bottle container 101, a scented article 108 may be incorporated into the cap 103 to enhance the experience of drinking the beverage. In the particular example shown in FIG. 1B, the base of movable portion 106 is flared outward to create a first encasement structure that includes an inner wall 109 and an outer wall 110 that forms at least a portion of a first channel. The first channel between inner wall 109 and outer wall 110 can be modified to fit and hold the upper portion of scented article 108 such that a portion of scented article 108 is exposed when the movable portion 106 is in the open position. In the example of FIG. 1B, the scented article 108 protrudes below the inner wall 109 and the outer wall 110. When movable portion 106 is in the open position, as shown in FIG. 1B, the protruding portion of scented article 108 is exposed to the air but shielded from making contact with the consumer's lips, e.g., by outer wall 110. Because liquid flows through flow channel 107, the scented article 108 is physically separated from fluid flow in any of the configurations of the movable portion 106, such as in the open position, the closed position or any position therebetween. Notably, in this configuration, when a consumer is drinking from spout 104, the consumer's nostrils will be located in close and measurable proximity to scented article 108.

The cap 103 includes a second encasement structure coupled to the fixed base 105 and that includes an inner wall 111 and an outer wall 112, such that the inner wall 111 and the outer wall 112 are arranged directly below and correspond to inner wall 109 and outer wall 110, respectively. The inner wall 111 and the outer wall 112 also form a portion of a second channel, labeled 113 in FIG. 1B. Together, corresponding inner wall 111 and corresponding outer wall 112 form channel 113 into which the protruding portion of scented article 108 can fit. Corresponding inner wall 111 and corresponding outer wall 112 are located such that, when movable portion 106 is lowered completely, they will meet inner wall 109 and outer wall 110, respectively, and form a contact seal. In this way, when movable portion 106 is lowered to its "closed" position, scented article 108 becomes encased within the seal created by the four walls. In this manner, the first encasement structure and the second encasement structure provide a scent chamber or compartment wherein, when the cap is in closed position, the contact seal created by the cap encloses the scented article within the compartment and locks in and traps the scent within, allowing controlled release of the scent to the outer environment.

The contact seal serves multiple purposes. In certain embodiments, the contact seal is air and water tight to preserve the scented article inside. In this way, when the bottle is first constructed, shipped, and deployed, e.g., in a retail environment, there will be no loss of scent, nor will the scents of adjacent bottles mix in the air in a store aisle. The contact seal can also function on reuse to preserve the scented article and extend its use.

There are various ways to accomplish this type of contact seal. In the initial construction, it may be desirable to have the walls be connected, either by an adhesive or a thin layer of material that can break away upon the bottle's first opening. Alternatively, and for reversible sealing of the scented article during multiple uses, the seal can be accomplished by ensuring the materials used to construct the walls have the proper balance of give (elasticity) and rigidity to accomplish the seal when mechanically compressed against each other, by incorporation of an additional lip of material on each of the walls at the connection point to provide additional surface area to enhance the seal, and/or incorporation of an O-ring or other flexible structure between the walls to enhance the seal. There are many example embodiments of component assemblies, described throughout this patent disclosure, that produce the seal of the scented article in a space that traps the scent within, while allowing the seal to be controllably unsealed to expose at least a portion of the scented article to release and/or emanate the scent. While the component assemblies to produce a reversible seal may be described in the context of a single embodiment, the component assemblies can also be implemented in multiple embodiments separately or in any suitable subcombinations.

In some embodiments, for example, the inner wall 109 and the outer wall 110 can be relatively longer than the inner wall 111 and the outer wall 112; whereas in some embodiments, the inner wall 109 and the outer wall 110 can be relatively shorter than the inner wall 111 and the outer wall 112. For example, in some embodiments, the inner wall 111 and outer wall 112 can be configured as a flat surface, rather than protrude upward, and the inner wall 109 and the outer wall 110 may be configured to be just as long or longer than the height of the scented article 108. In such examples, the scented article 108 may sit on the flat surface and the longer inner wall 109 and outer wall 110 would cover scented article 108 when movable portion 106 is closed, while exposing the underside of the scented article 108 when the movable portion 106 is pulled open.

While FIG. 1B depicts scented article 108 as a ring, and the walls surrounding it completely circular, one of ordinary skill would understand that it need not be so. So long as the walls are constructed to seal around the entirety of scented article 108 when closed, scented article 108 can be shaped in other configurations to fit within the upper channel portion and lower channel portion 113. An example illustrating such configurations is discussed with respect to FIG. 1C.

Figure 1C:
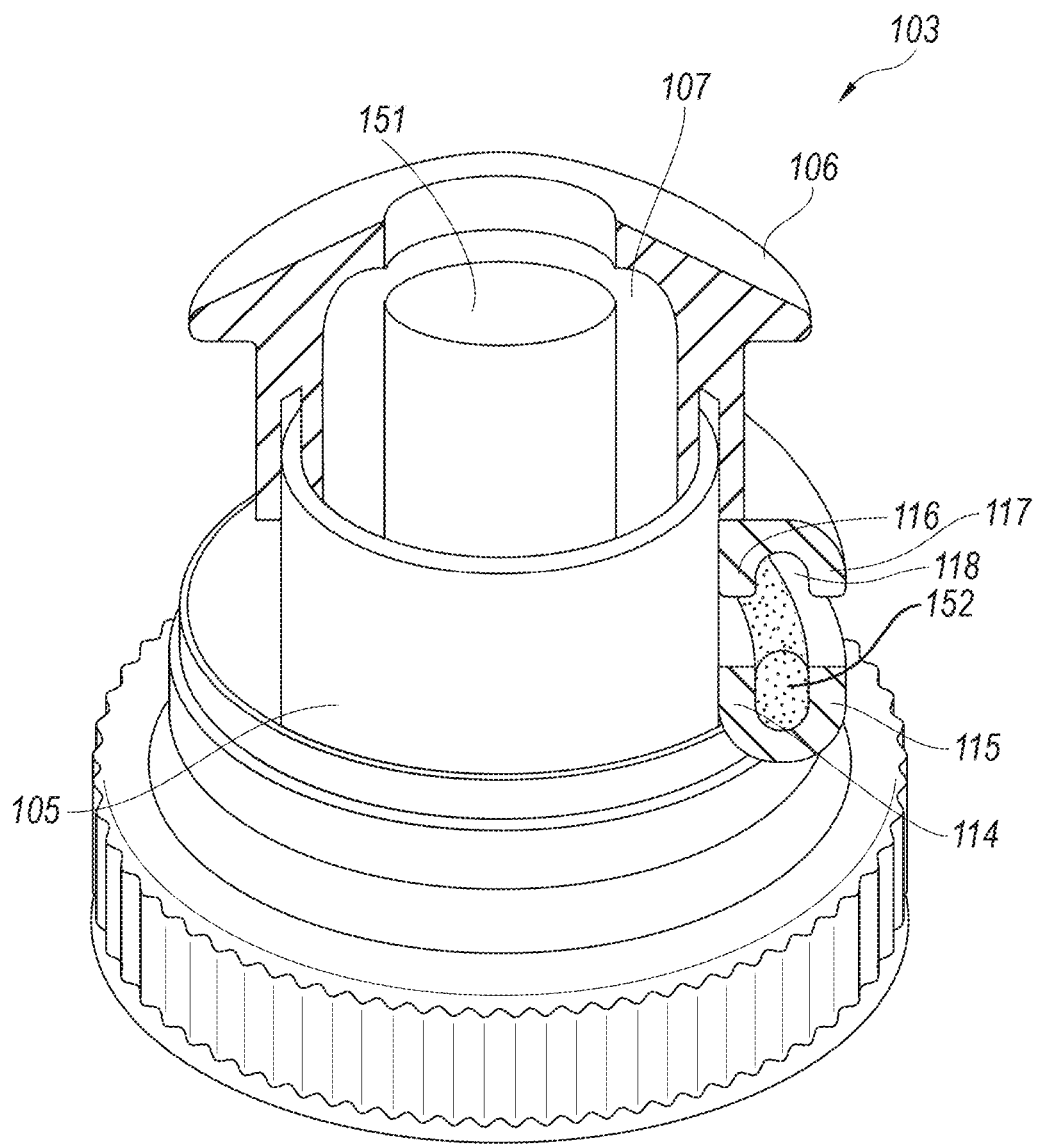

FIG. 1C presents an alternative embodiment of the arrangement in FIG. 1B, in which a scented article 152 is arranged in the cap 103 around a part of the movable portion 106. In this example, the cap 103 includes an inner wall 114 and an outer wall 115 that are built up from the top surface of fixed base 105. Scented article 152 is disposed between inner wall 114 and outer wall 115, so that a portion of scented article 152 protrudes upward above them. When movable portion 106 is in its "open" position, the protruding portion of scented article 152 is exposed to the air.

In the example of FIG. 1C, the bottom edge of movable portion 106 contains inner wall 116 and outer wall 117 that are arranged directly above and correspond to inner wall 114 and outer wall 115. Together, the inner wall 116 and outer wall 117 form a channel 118 into which the protruding portion of scented article 152 can fit. The corresponding inner wall 116 and outer wall 117 are located such that, when movable portion 106 is lowered completely, they will meet inner wall 114 and outer wall 115, respectively, and form a contact seal. In this way, when movable portion 106 is lowered to its "closed" position, scented article 152 becomes encased within the seal created by the four walls.

While scented article 152 is located beneath movable portion 106 in the embodiment in FIG. 1C, it is important to note that scented article 152 remains protected from the consumer's lips by the shape of corresponding outer wall 117. Moreover, liquid traveling through flow channel 107 is still physically separated from scented article 152.

As with the embodiment in FIG. 1B, the embodiment depicted in FIG. 1C need not use a ring-shaped scented article or ring shape spout, but rather any shape, including a portion of a curved structure that fits in the channel formed between the walls 114, 115, 116 and 117, which can be used so long as the walls are constructed to seal around the entirety of scented article 152 when movable portion 106 is closed.

Beverage containers utilizing nipple-type spouts are sometimes sold pre-filled at retail intended for single use, while others are sold intended for multiple-time re-use with washing in between. In some of the embodiments described herein, the scented article may be attached to the beverage container during its initial assembly and filling with a beverage in a way that it is nonremovable by the end user; or in some embodiments, the scented article may be attached in a removable, fashion so that it can be replaced when the end user desires to do so. While nonremovable attachment can be accomplished with chemical adhesives, FIG. 1D also shows several manners by which the scented article can be removably attachable (e.g., capable of being attached and detached) without the use of additional chemicals that might interfere with the scented article.

Figure 1D:
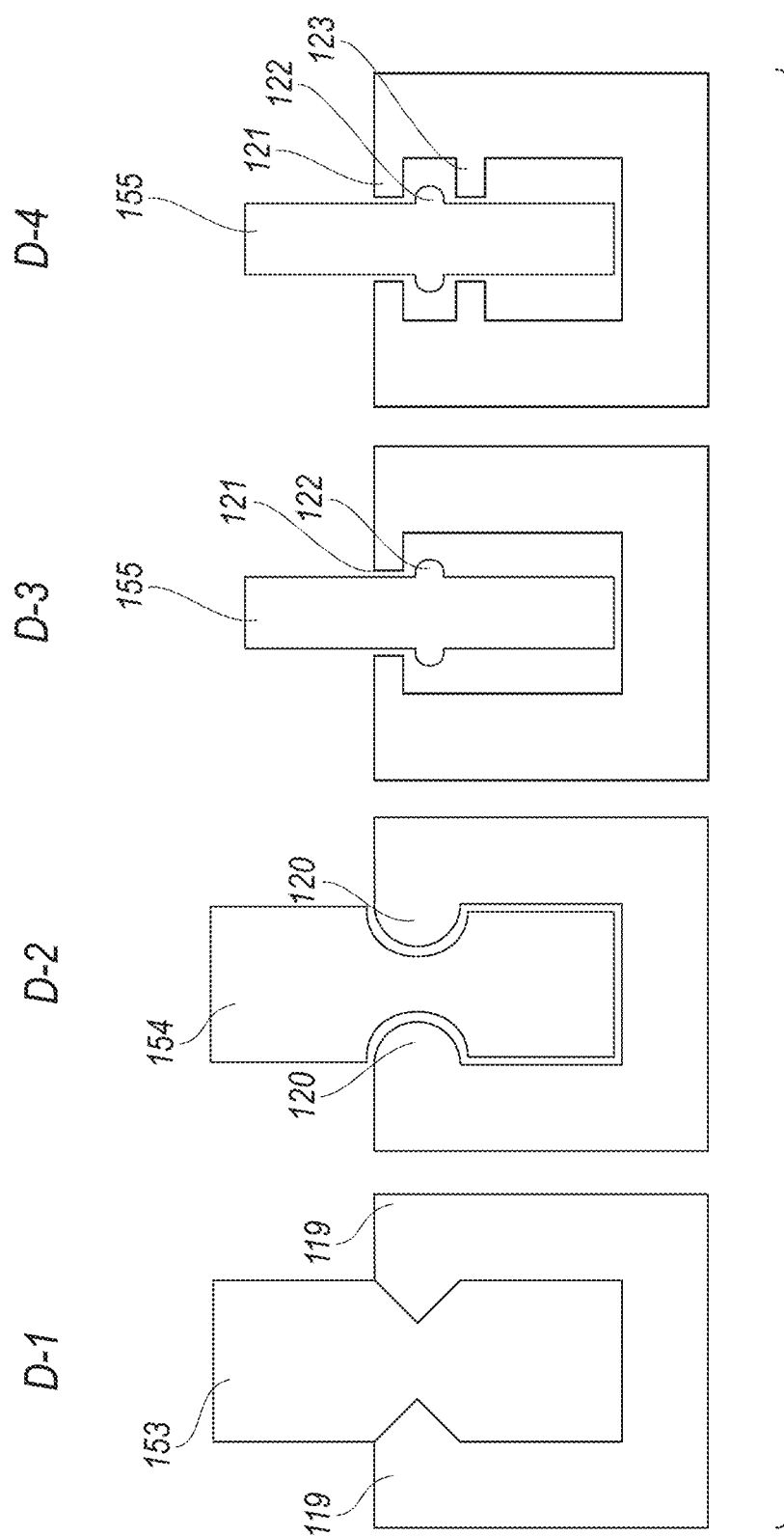

In schematic D-1 of FIG. 1D, scented article 153 is structured to be virtually the same width as the channel between the walls surrounding it, but scented article 153 contains cavities on its interior and exterior surfaces. Triangular projections 119 from the walls match the shape of these cavities and physically contact the sides of scented article 153 once it is pressed downward into place during assembly. This form of rigid attachment should prevent scented article 153 from moving. In some examples, the triangular projections 119 are discontinuously disposed along the walls of the channel and configured to align within corresponding discontinuous cavities of the scented article 153 or within uniform cavities of the scented article 153 that can span along at least a portion of the interior and exterior surfaces of the scented article 153. While the example schematic D1-1 shows the triangular projections 119 protruding from the walls of the channel to align within the cavities of the scented article 153, it is understood that the triangular projections 119 may be contained on the walls of the scented article 153 and the cavities may be disposed on the walls of the channel.

Schematic D-2 of FIG. 1D shows a slight variation of this arrangement, wherein the projections 120 extending from the walls are rounded instead of triangular, and, such that the projections 120 generally match the cavities on the sides of scented article 154. With such projections, the scented article 154 (and scented article 153, for example) can be structured to have a width slightly narrower than the channel between the walls surrounding it. Physical contact between the projections 120 and scented article 154 need not be maintained so long as projections 120 extend sufficiently into the sides of scented article 154 to keep it from dislodging.

In schematic D-3 of FIG. 1D, the walls are constructed with a lip 121 that projects out into the channel in which scented article 155 is mounted. Lip 121 restrains the scented article 155 due to projections 122 extending from the exterior surface of the scented article 155 out toward the walls. The projections 122 of the scented article 155 have a width dimension from end-to-end that is larger than the width of the opening into the channel due to the projection of the lip 121. For example, the projections 122 can be rounded like projections 120 or triangular like projections 119, or have other shapes based on other material properties of the scented article that allow it to be pushed into the channel such that the projections 122 pass the lip 121 of the walls.

Schematic D-4 of FIG. 1D is a variation of this arrangement where, in addition to lip 121, a lower lip 123 is used to bookend projection 122. Similarly, in some embodiments, a third lip (not shown) can be disposed below the lower lip 123, such that a scented article having two projections, e.g., projection 122 and a lower projection projecting from scented article 155 to be below lower lip 123 (not shown), may align in the spacing between (i) the lip 121 and lower lip 123 and (ii) the lower lip 123 and the third lip, respectively. This configuration can, among other things, allow the scented article to be manufactured with less material so that it need not abut the bottom of the channel but yet still be secured within the channel to allow for controllable reversible attachment.

FIGS. 2A-2I present other arrangements for how a scented system can be applied to a kind of nipple-type spout on drinking containers used during active pursuits such as sports.

Figure 2A:
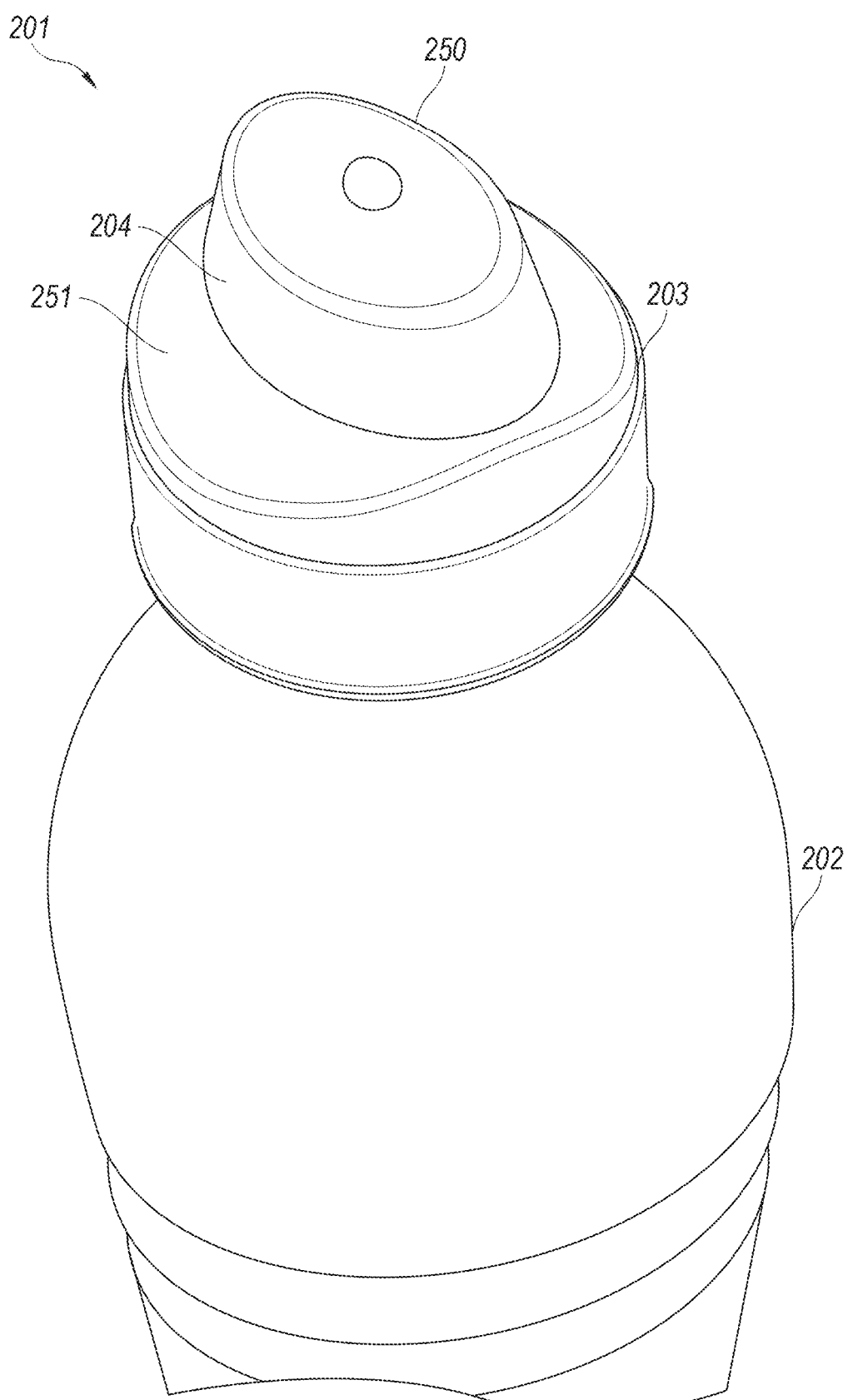
FIGS. 2A-2I show example embodiments of a scented beverage system including a scented article configured inside a sealable channel or chamber of a drinking container featuring an alternatively-shaped nipple-type spout.

As shown in FIG. 2A, beverage container 201 includes a container body 202 and cap 203. Like in FIGS. 1A-1D, instead of merely presenting an opening or spout for the consumer to drink from requiring the user to attach and remove the cap, the cap 203 of the beverage container 201 is fitted with a "nipple-type" spout 204 at an upper region of the cap 203 and attaches to the body 202 at a lower region of the cap 203. The cap 203 can attach to the body 202 at the lower region of the cap 203 by a threading that interfaces between a portion of the lower region of the cap 203 and an upper region of the body 202 to allow the lower region of the cap 203 to screw down onto a threaded region at the mouth of body 202. In some embodiments, the beverage container 201 can include an outer cap (not shown) that covers the cap 203, e.g., to protect the nipple-type spout 204 from contaminants or unwanted contact by other objects. In contrast to the narrower, cylindrical spout presented in FIGS. 1A-C, for example, the top surface of spout 204 of the beverage container 201 includes an ovular-shaped projection 250, more closely matching the general shape of an open mouth than a circle. In addition, a middle region of the spout 204 descends from that oval to a broader, flatter disk-shaped base 251 of the spout 204.

Figure 2B:
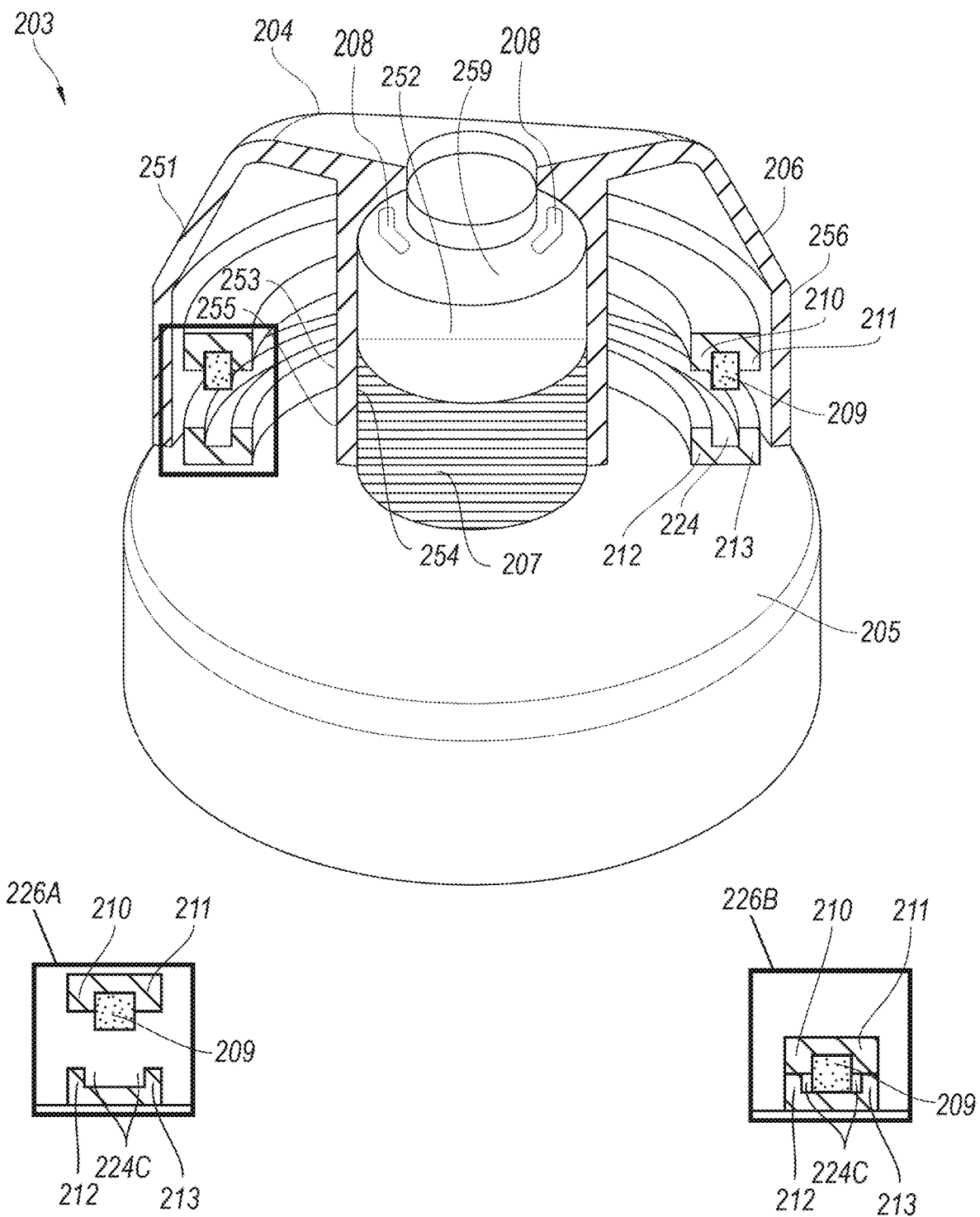

FIG. 2B shows an example embodiment of the cap 203. The diagram of FIG. 2B, showing a partial cutaway view or semi-cross-sectional enlargement of cap 203, illustrates the shape of the interior of the spout 204. Spout 204 includes a fixed base 205 and a movable component or assembly 206 (also referred to as "movable portion" 206), in which the fixed base 205 does not move relative to the lower region of the cap 203, and the movable portion 206 moves relative to the fixed base 205. In FIG. 2B, the movable portion 206 is intended to move in a twisting, rather than a sliding fashion. To accomplish this, fixed base 205 includes a hollowed barrel 259 with an opening at the bottom and having threaded region 207 and a non-threaded region 252 on the outer surface of the barrel. Movable portion 206 contains an inner cylinder 253 that is just slightly wider in its inner diameter than the outer diameter of hollowed barrel 259. Inner cylinder 253 has an inner surface 254 that is threaded to match threaded region 207 and an outer surface 255 that can be smooth. When movable portion 206 is mounted onto fixed base 205 during assembly, inner surface 254 and threaded region 207 are engaged so that movable portion 206 can be raised and lowered by way of a twisting motion. As movable portion 206 is raised and lowered, respectively, one or more fluid flow-channels 208 that lead to the hollow interior region of the barrel 259 and are opened and closed based on non-contact and contact, respectively, with the surface of the inner cylinder structure of the movable portion 206, thereby allowing or preventing access to liquid stored inside the base of the bottle. Moreover, disk-shaped base 251 includes a vertical flange 256 that meets the top surface of fixed base 205 when movable portion is closed. In this manner, for example, a scented article 209 can be incorporated in the cap 203 such that a surface of the scented article 209 is exposed and sealed when the cap is opened and closed, respectively, as described below.

In the example shown in FIG. 2B, the movable portion 206 is in its uppermost or "open" position lifted above the barrel 259, which opens (e.g., unseals and exposes) the flow-channel 208 to allow liquid to flow through and out of the cap 203. When movable portion 206 is lowered to its lowest or "closed" position, the flow-channel 208 is blocked and liquid cannot flow. In the space between the inner cylinder 253 and an outer wall (e.g., vertical flange 256) of the movable portion 206, a first encasement structure is coupled to the movable portion to attach the scented article 209. In the example of FIG. 2B, the first encasement structure is configured along the inner surface of vertical flange 256 and includes an inner wall 210 and an outer wall 211, such that the upper portion of the scented article 209 is held between the inner wall 210 and the outer wall 211, in which a portion of scented article 209 protrudes below them. When movable portion 206 is in the open position, as shown in FIG. 2B, the protruding portion of scented article 209 is exposed to the air but shielded from the consumer's lips, e.g., by the vertical flange 256. Because liquid flows through flow-channel 208, it is physically separated from scented article 209. Nevertheless, when a consumer is drinking from spout 204, the consumer's nostrils will be located in close proximity to scented article 209, e.g., thereby being able to inhale the desired scent from the scented article 209 with proximally targeted precision.

The fixed base 205 includes a second encasement structure that includes a corresponding inner wall 212 and corresponding outer wall 213, which can be built into the fixed base 205 directly below inner wall 210 and outer wall 211. Together, corresponding inner wall 212 and corresponding outer wall 213 form a receiving channel 224 into which the protruding portion of scented article 209 can fit. Corresponding inner wall 212 and corresponding outer wall 213 are located such that, when movable portion 206 is lowered completely, they will meet inner wall 210 and outer wall 211, respectively, and form a contact seal. In this way, when movable portion 106 is lowered to its "closed" position, scented article 209 becomes encased within the seal created by the four walls. In this manner, the first encasement structure and the second encasement structure provide a scent chamber or compartment wherein, when the cap 203 is in closed position, the contact seal created by the walls 210, 211, 212 and 213 of the cap encloses the scented article within the compartment and locks in and traps the scent within, allowing controlled release of the scent to the outer environment.

In some implementations, to transition between the "closed" position and the "open" position, the twisting of the movable portion 206 raises the movable portion (and thereby the walls 210, 211 with scented article 209) to a height above the fixed base 205 greater than the height of the corresponding walls 212 and 213, creating an opening into the interior of the movable portion 206 that allows the scent to dispense out of the cap 203. In some embodiments, for example, the pair of corresponding walls 211 and 213 can be configured to have a substantially the same width and the pair of corresponding walls 210 and 212 can be configured to have a substantially the same width, respectively. Yet, in some embodiments, for example, the wall 211 can be configured to have a width greater than the width of the corresponding wall 213 so that, when the movable portion 206 in in the "open" position, there is a slight gap between the outer surface of the corresponding wall 213 and the interior surface of the vertical flange 256 to allow the scent to be delivered out of the cap 203, e.g., in proximity to the user's nose while consuming the fluidic beverage dispensed from the top opening of the cap 203 into the user's mouth.

In some embodiments, the corresponding inner wall 212 and corresponding outer wall 213 are structured to include a wider gap between them than the gap between the inner wall 210 and the outer wall 211, in which the receiving channel 224 is wider than the than the width of the scented article 209. In this manner, for example, an empty space or chamber exists proximate the scented article 209 when the contact seal is formed. For example, in implementations, the scented article 209 will emanate the scent to a concentration trapped within the empty chamber; and when the movable portion 206 is raised, i.e., in the open position, the trapped scent can burst out of the chamber to be inhaled by the user as a first sip of the beverage is consumed. This example embodiment is shown in the inset boxes 226A and 226B of FIG. 2B, corresponding to the open position and closed position, respectively, in which the receiving channel 224C includes the empty space or chamber when the contact seal is formed to trap the emanated scent within.

While FIG. 2B depicts scented article 209 and the associated wall structures at the outer perimeter of movable portion 206, they could be located in any position relative to screw-like track 207, including juxtaposed to it, as shown in FIGS. 2D-2G, for example. Scented article 209 may be attached to the walls of the first encasement in any of the manners described herein, including but not limited to those in FIG. 1D. Moreover, while FIG. 2B depicts scented article 209 as a ring, and the walls surrounding span the entire circumference of the movable portion 206, other embodiments of the cap 203 include a scented article and surrounding walls that span a portion of the circumference of the movable portion 206. In such embodiments, the walls are constructed to seal around the entirety of scented article 209 when closed, and the scented article 209 can be configured of any shape.

Figure 2C:
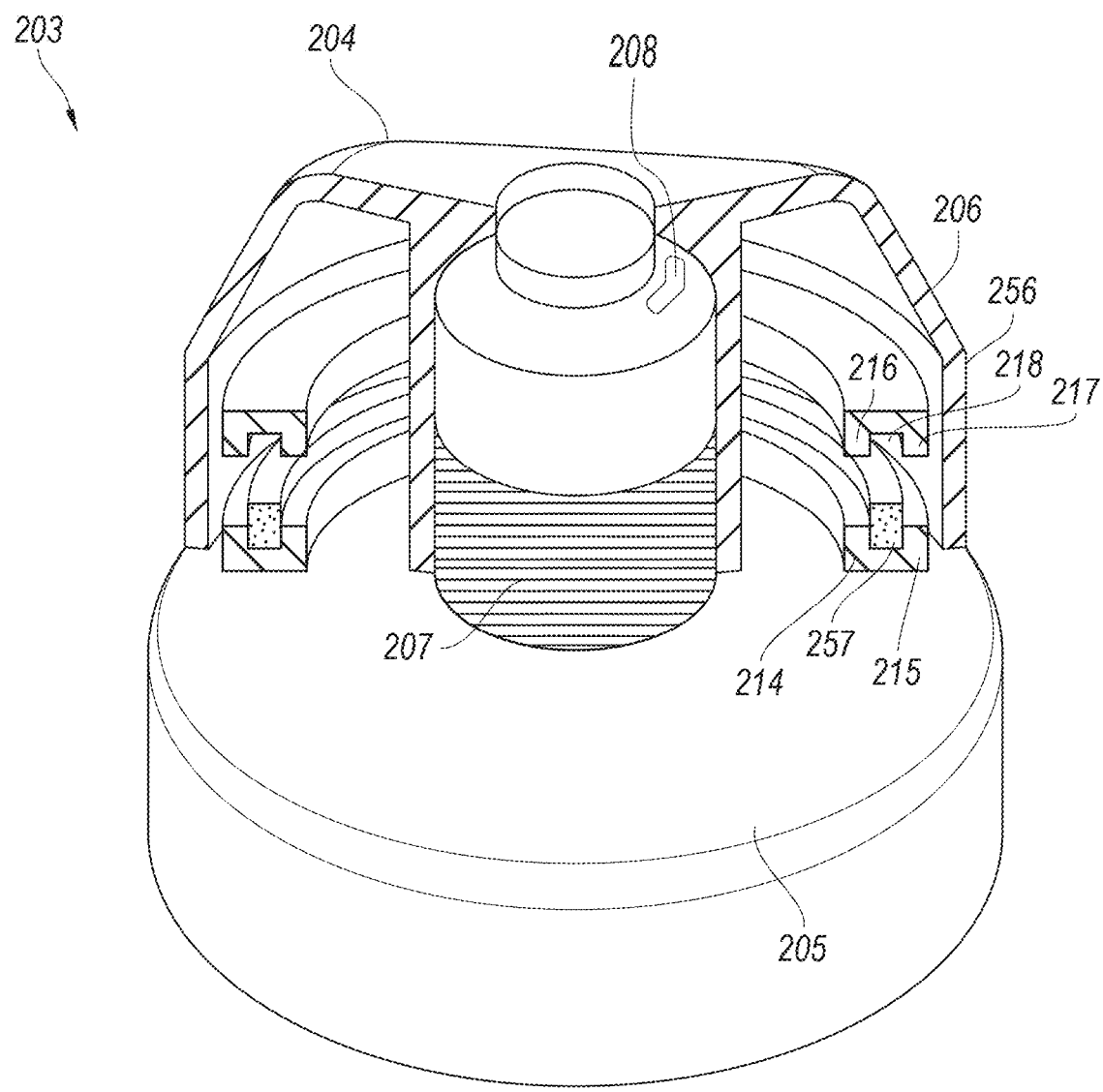

FIG. 2C presents an example embodiment of the cap 203 similar to the arrangement in FIG. 2B. In this embodiment, the first encasement structure includes an inner wall 214 and outer wall 215, which are built up from the top surface of fixed base 205 and form a portion of a channel that a scented article 257 is disposed within, so that a portion of scented article 257 protrudes upward above them. When movable portion 206 is in its "open" position, the protruding portion of scented article 257 is exposed to the air.

In the embodiment of FIG. 2C, the second encasement structure is coupled to the inside edge of vertical flange 256, which contains a corresponding inner wall 216 and corresponding outer wall 217 (e.g., corresponding to the inner wall 216 and the inner wall 215, respectively). Together, corresponding inner wall 216 and corresponding outer wall 217 form a receiving channel 218 into which the protruding portion of scented article 257 can fit. Corresponding inner wall 216 and corresponding outer wall 217 are located such that, when movable portion 206 is lowered completely, they will meet inner wall 214 and outer wall 215, respectively, and form a contact seal. In this way, when movable portion 206 is lowered to its "closed" position, scented article 209 becomes encased within the seal created by the four walls. In some implementations of the cap 203 in FIG. 2C, to transition between the "closed" position and the "open" position, the twisting of the movable portion 206 raises the movable portion (and thereby the corresponding walls 216, 217) to a height above the fixed base 205 greater than the height of the walls 214 and 215, creating an opening into the interior of the movable portion 206 that allows the scent to dispense out of the cap 203. In some embodiments, for example, the pair of corresponding walls 215 and 217 can be configured to have a substantially the same width and the pair of corresponding walls 214 and 216 can be configured to have a substantially the same width, respectively. Yet, in some embodiments, for example, the upper corresponding wall 217 can be configured to have a width greater than the width of the lower outer wall 215 so that, when the movable portion 206 in in the "open" position, there is a slight gap between the outer surface of the outer wall 215 and the interior surface of the vertical flange 256 to allow the scent to be delivered out of the cap 203, e.g., in proximity to the user's nose while consuming the fluidic beverage dispensed from the top opening of the cap 203 into the user's mouth.

While scented article 257 is located on fixed base 205 in the embodiment in FIG. 2C, it is important to note that scented article 257 remains protected from the consumer's lips by the shape of movable portion 206. Moreover, liquid traveling through channel 208 is still physically separated from scented article 257.

As with the embodiment in FIG. 2B, scented article 257 and the associated wall structures in FIG. 2C could be located in any position relative to screw-like track 207, including directly juxtaposed to it. Scented article 257 may be attached in any of the manners described herein, including but not limited to those in FIG. 1D. Moreover, the embodiment depicted in FIG. 2C need not use a ring-shaped scented article, but rather any portion of a region of the cap 203, e.g., in the interior of the movable portion 206, can be used so long as the walls are constructed to seal around the entirety of scented article 257 when movable portion 206 is closed.

Figure 2D:
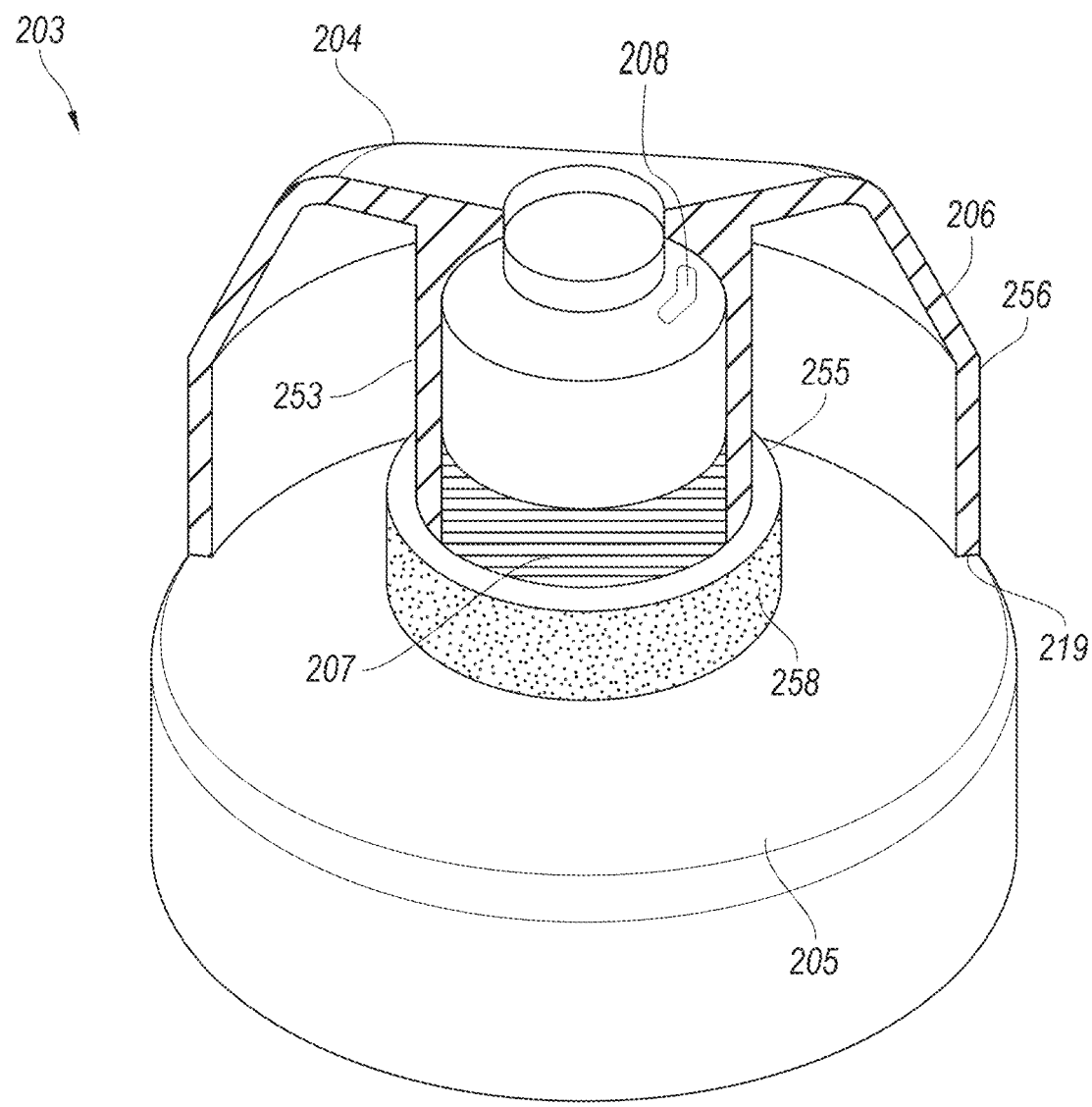

In FIG. 2D, a scented article 258 is attached in a position juxtaposed against the exterior surface 255 of inner cylinder 253. Instead of using specially-created walls disposed in the space between movable portion 206 and fixed base 205, those two structures themselves are used to create the sealed channel. Specifically, when movable portion 206 is in its "open" position, as shown in FIG. 2D, air is able to pass under vertical flange 256 at its bottommost lip 219. However, when movable portion 206 is screwed down into its "closed" position, bottommost lip 219 forms a contact seal with fixed base 205. Such an arrangement allows scented article 258 to fill the space beneath movable portion 206 with scent between uses, providing a high concentration burst of scent to the consumer the next time the bottle is opened.

In the example shown in FIG. 2D, scented article 258 is shown as a complete ring, necessitating its attachment before the installation of movable portion 206. However, scented article 258 can be constructed in a variety of shapes. Some of these, including any that are physically attached to fixed base 205 in the manners described elsewhere herein, including but not limited to those in FIG. 1D, may similarly require installation before movable portion 206. However, if scented article 258 were formed in the shape of a partial, or C-shaped ring, it could be clipped around exterior surface 255 after the installation of movable portion 206. In some implementations, for example, the example C-shaped ring can also be compressed when inserted such that it makes a complete ring. In addition, for example, the scented article 258 could be mounted inside movable portion 206 before movable portion 206 is attached to fixed base 205.

In other examples, the scented article 258 can fill most of the space under movable portion 206.

Figure 2E:
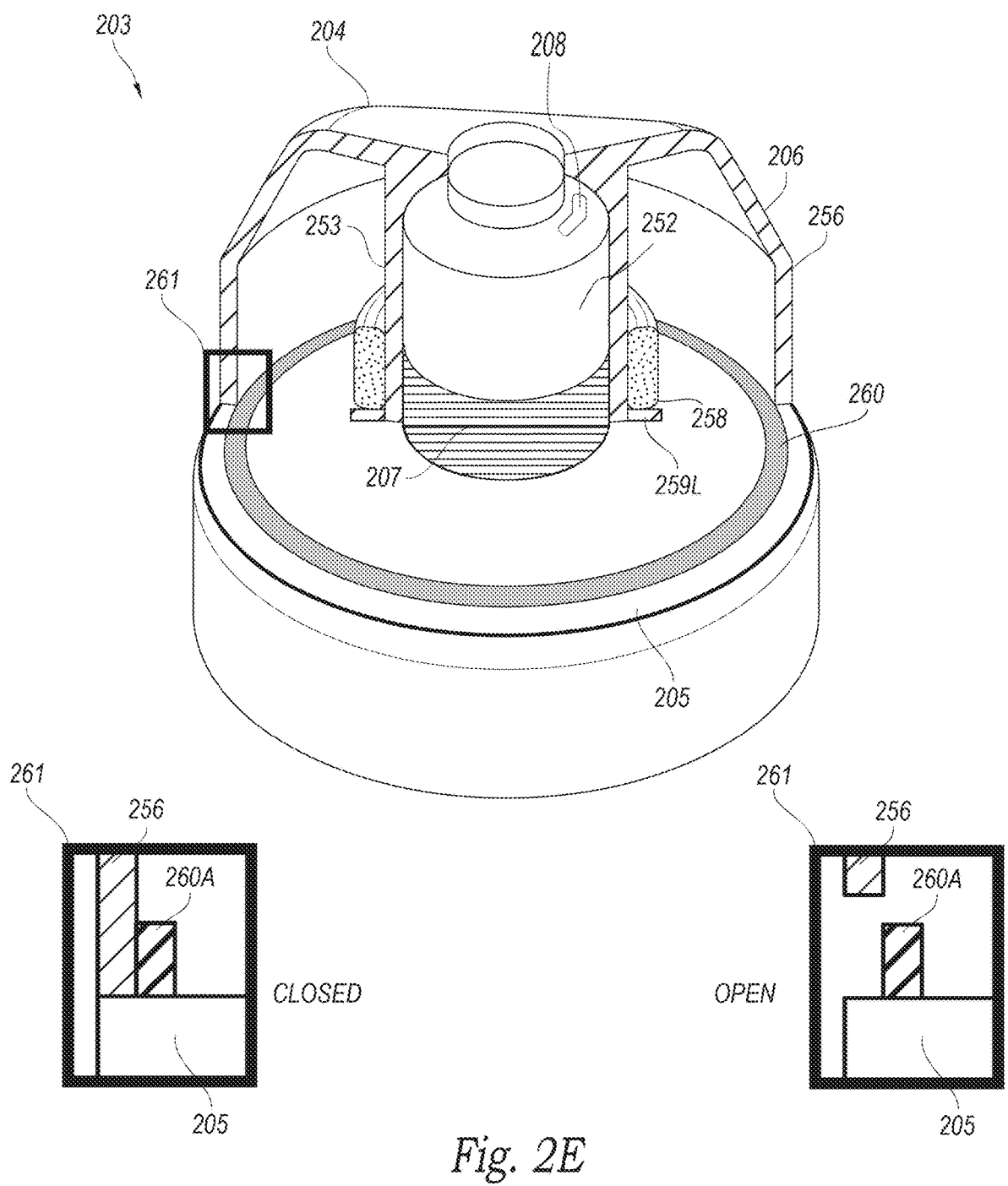
Figure 2F:
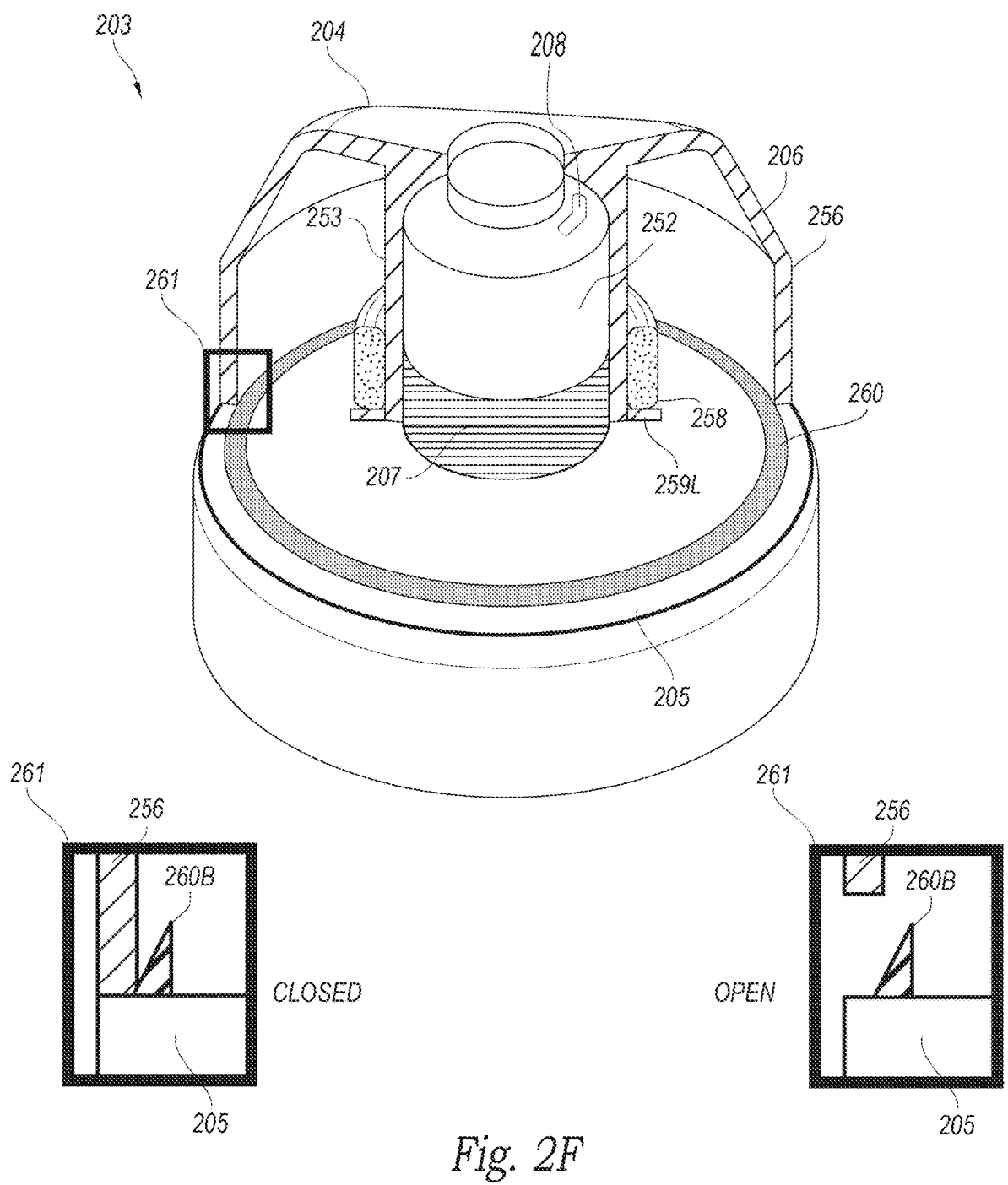
Figure 2G:
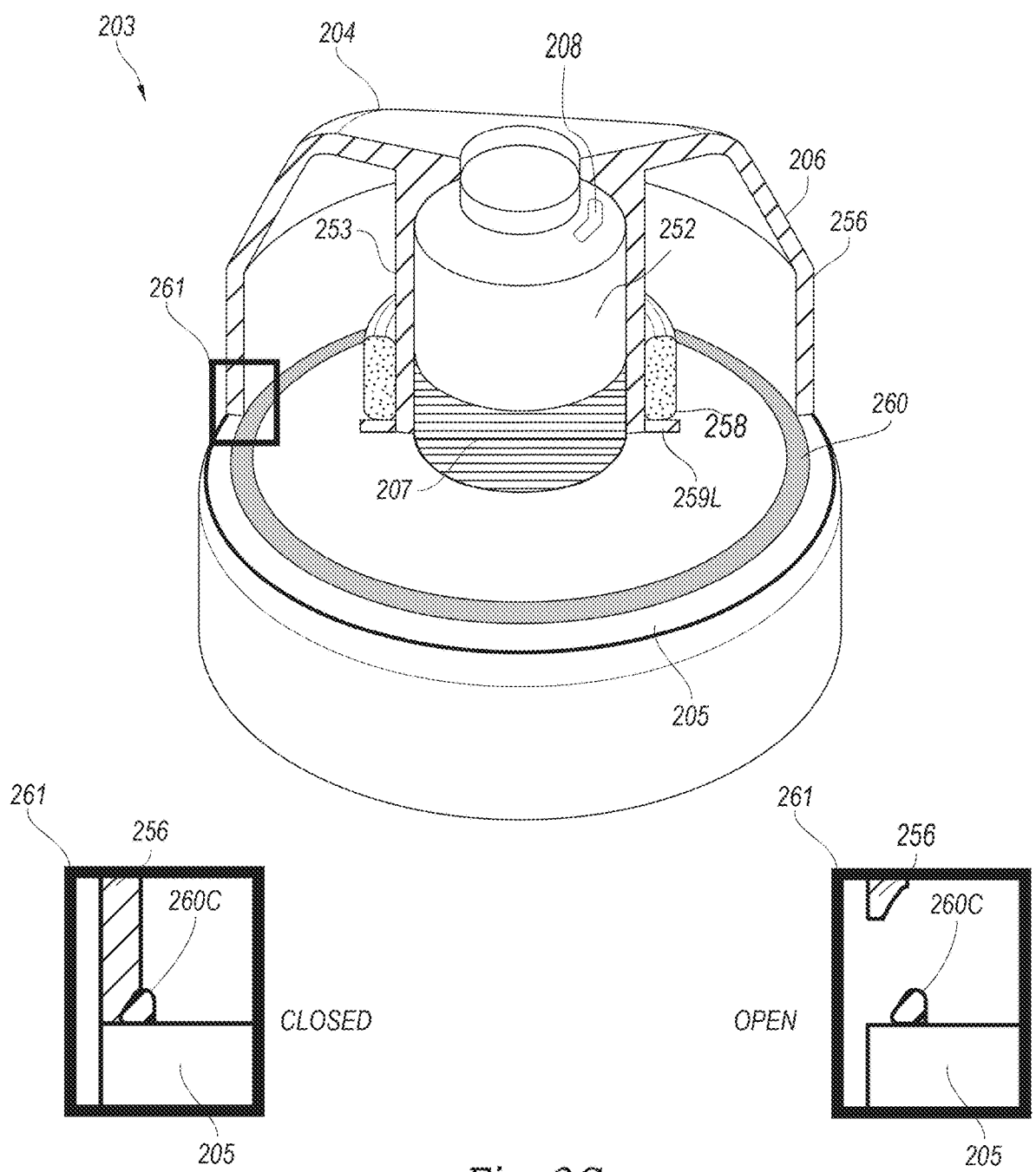

FIGS. 2E-2G show example embodiments of the cap 203, similar to FIG. 2D, in which the scented article 258 is sealed within the interior of the movable portion 206 by an interfacing structure 260 that form a seal with the interior surface of the vertical flange 256. In the examples shown in FIGS. 2E-2G, the scented article 258 is configured on a ledge 259L expanding out from the inner cylinder 253 within the interior of the movable portion 206. In some implementations, the scented article 258 is configured around the inner cylinder 253 without a ledge. A ledge, e.g., the ledge 259L, can be configured to protrude slightly outward from the surface to which the scented article 258 abuts. For example, the ledge can protrude outward at a distance that is less than 100% of the width of the scented article 258, e.g., such as a range of 10% to 99% of the width, providing sufficient surface area for the scented article 258 to rest upon while also allowing for the scented article 258 to be separately assembled thereon. Yet, in some examples, the ledge 259L can be configured to protrude outward at the same distance or greater than the width of the scented article 258.

The interfacing structure 260 can include a protrusion structure of various geometries, such as the example interfacing structure 260A in FIG. 2E, the example interfacing structure 260B in FIG. 2F, and the example interfacing structure 260C in FIG. 2G. The insets, labeled 261 as shown in FIG. 2E, show an example of the interfacing structure 260A that is disposed on the fixed base 205 to align with an outer wall with the interior wall of the vertical flange 256; such that when the cap 203 is in the closed position, the two surfaces are in contact and form the seal, and when the cap 208 is in the open position, the vertical flange 256 is raised above the height of the interfacing structure 260A.

The insets, labeled 261 as shown in FIG. 2F, show an example of an interfacing structure 260B formed of a pliant material and structured to have an angled outer wall that is disposed on the fixed base 205 partially underneath the interior wall of the vertical flange 256; such that when the cap 203 is in the closed position, the vertical flange 256 contacts and compresses a small portion of the angled outer wall that is underneath the vertical flange 256 to form the seal, and when the cap 203 is in the open position, the vertical flange 256 is raised above the height of the contact location of the angled outer wall of the interfacing structure 260B.

The insets, labeled 261 as shown in FIG. 2G, show an example of an interfacing structure 260C structured to have an angled or curved outer wall that is disposed on the fixed base 205 partially underneath the interior wall of the vertical flange 256, which has an indentation that substantially matches the geometry of the angled or curved outer wall of the interfacing structure 260C; such that when the cap 203 is in the closed position, the vertical flange 256 contacts the angled or curved outer wall of the interfacing structure 260C that is underneath the vertical flange 256 to form the seal, and when the cap 203 is in the open position, the vertical flange 256 is raised above the height of the interfacing structure 260C.

Figure 2H:
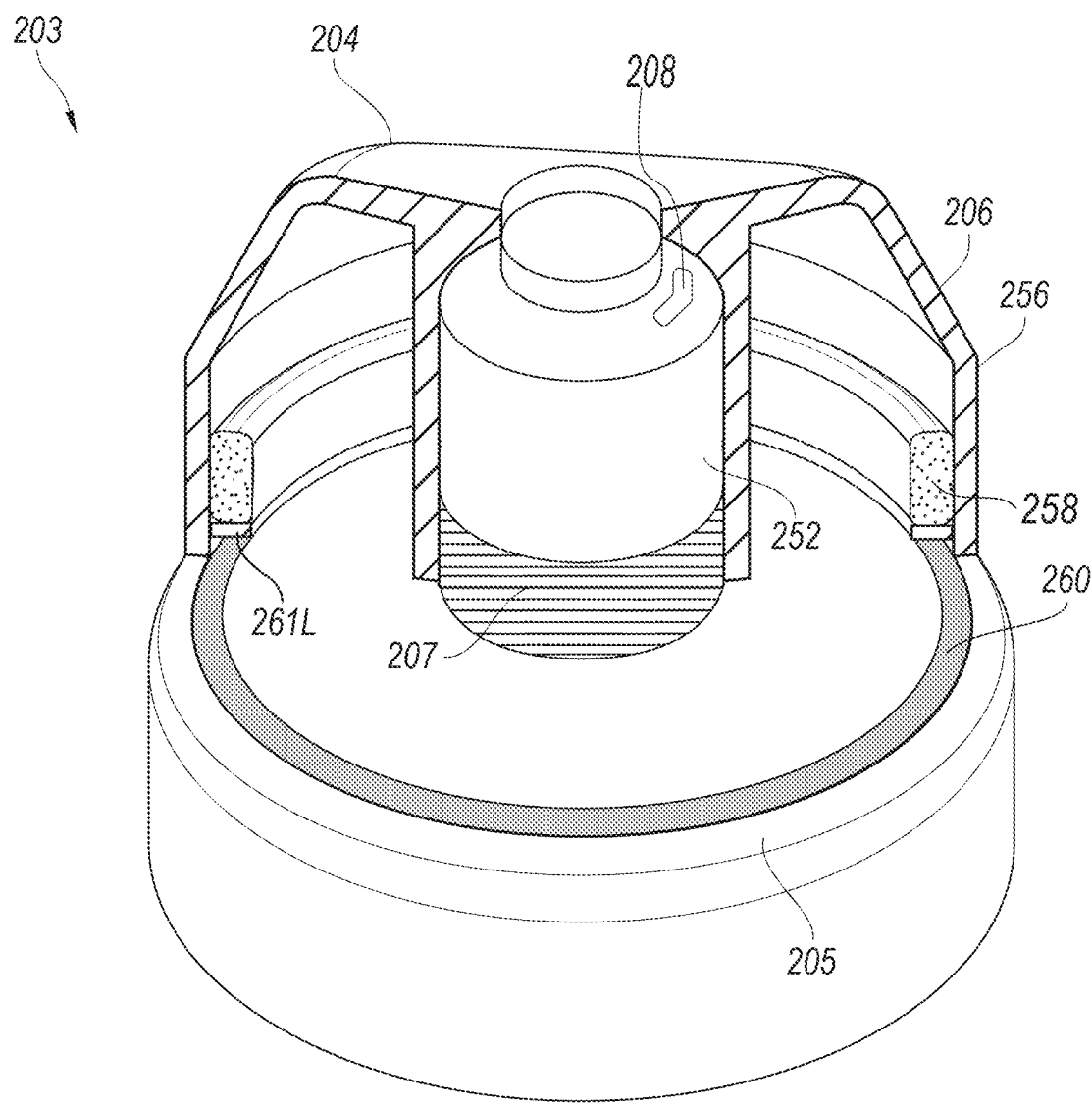
Figure 2I:
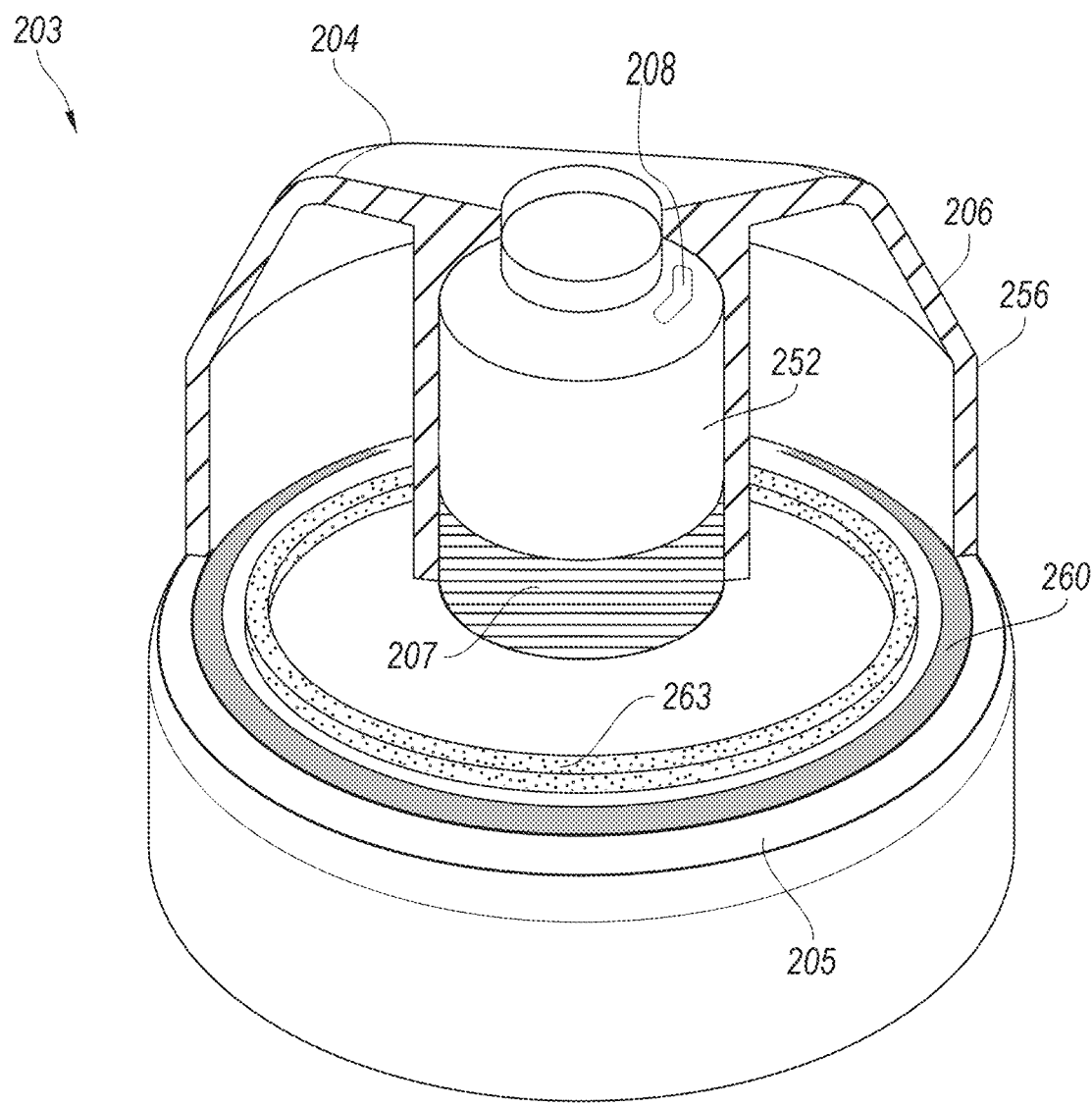

FIGS. 2H and 2I show example embodiments of the cap 203, similar to FIG. 2D and FIGS. 2E-2G, in which the scented article 258 is configured to attach to the interior wall of the vertical flange 256 or on the surface of the fixed base 205.

FIG. 2H shows an example of a ledge 261L expanding out from the interior wall of the vertical flange 256 to maintain the scented article 258 within the interior of the movable portion 206. For example, the ledge 261L can be configured to protrude slightly outward from the surface to which the scented article 258 abuts, e.g., such as protrude outward to 10% to 99% of the width of the scented article 258 to sufficiently support the scented article 258 when set upon it while also allowing for the scented article 258 to be separately assembled thereon. Yet, in some examples, the ledge 261L can be configured to protrude outward at the same distance or greater than the width of the scented article 258. In some implementations, the scented article 258 is configured around the vertical flange 256 without a ledge, e.g., based on adhesion or interfacing structures like those shown in FIG. 1D.

In some implementations, for example, the positioning and manner of attaching the scented article 258 to the cap 203 can optimize the desired amount of surface area the scented article 258 has exposed in the scent chamber or compartment, and thereby to the outer environment when the cap 203 is in the open position. In some examples, scented article 258 can be larger when it is configured around the interior wall of the vertical flange 256, e.g., as compared to when the scented article is configured around the inner cylinder 253 or locations between the interior wall of the vertical flange 256 and the inner cylinder 253. In some implementations, for example, the scented article 258 can span the space from vertical flange 256 to inner cylinder 253.

FIG. 2I shows an example of the scented article, labeled 263, that is configured on the surface of the fixed base 205. While FIGS. 2E-2I depict the scented article 258 and 263 as a ring or object that spans around the movable portion 206 at various radial distances from the center of the movable portion 206, other embodiments of the scented article can span a portion of the movable portion 206.

FIGS. 3A, 3A-1, and 3B-3D show example embodiments of a scented system applied to a beverage container utilizing a different kind of spout, namely a sealable straw-type spout. Such spouts are often preferred by parents as a drinking system for their children given that it is both rugged and prevents spillage.

Figure 3A:
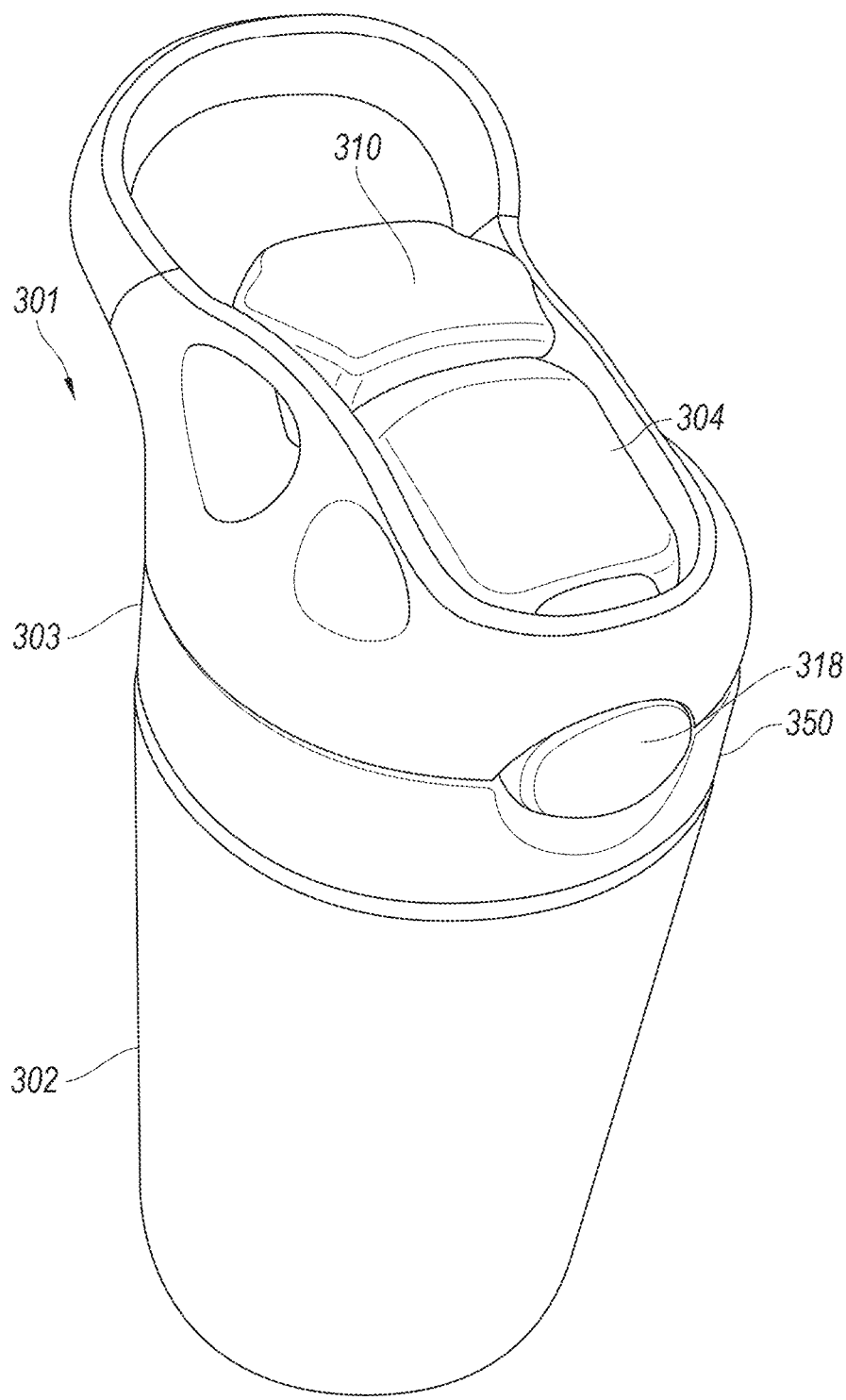
FIGS. 3A, 3A-1, and 3B-3D show example embodiments of a scented beverage system including a scented article configured inside a sealable channel of a drinking container featuring a straw-type spout.
Figures 1, 3A:
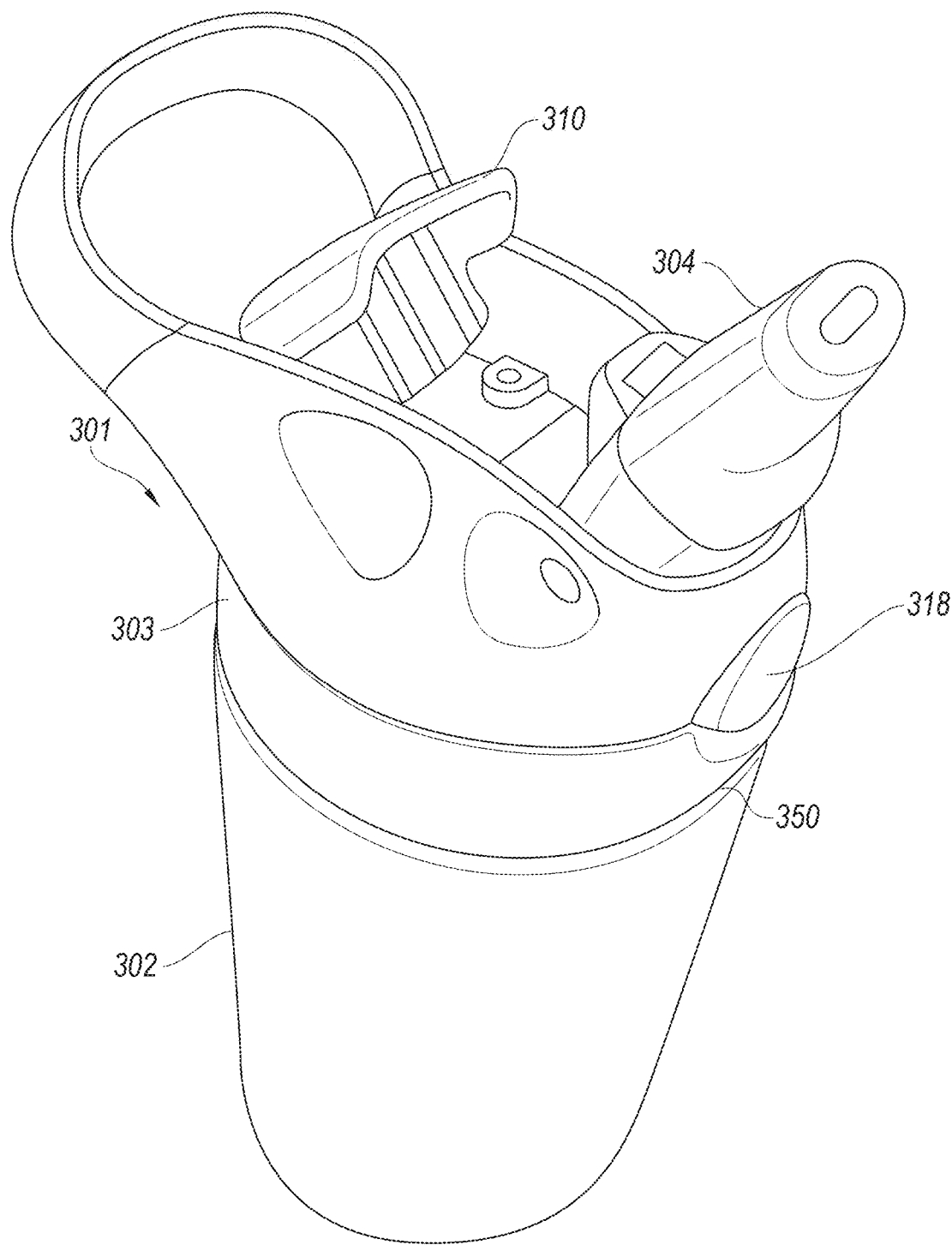

FIG. 3A shows beverage container 301. In particular, container 301 includes a container body 302 and cap 303, where cap 303 is fitted with a straw-type spout 304 and screws down over a threaded portion 350 of container body 302. As shown, straw-type spout 304 can assume two positions, an elevated, "open" position where a beverage can flow through the spout, and a lowered, "closed" position where the interior of the container is sealed. The beverage container 301 is also equipped with cover 310, which is incorporated to fold down over the tip of straw-type spout 304 when it is in the closed position. The straw-type spout 304 is operable to open from the closed position by actuation of button 318. FIG. 3A-1 shows another elevated view of the beverage container 301 depicting a hollow region or well 305.

Figure 3B:
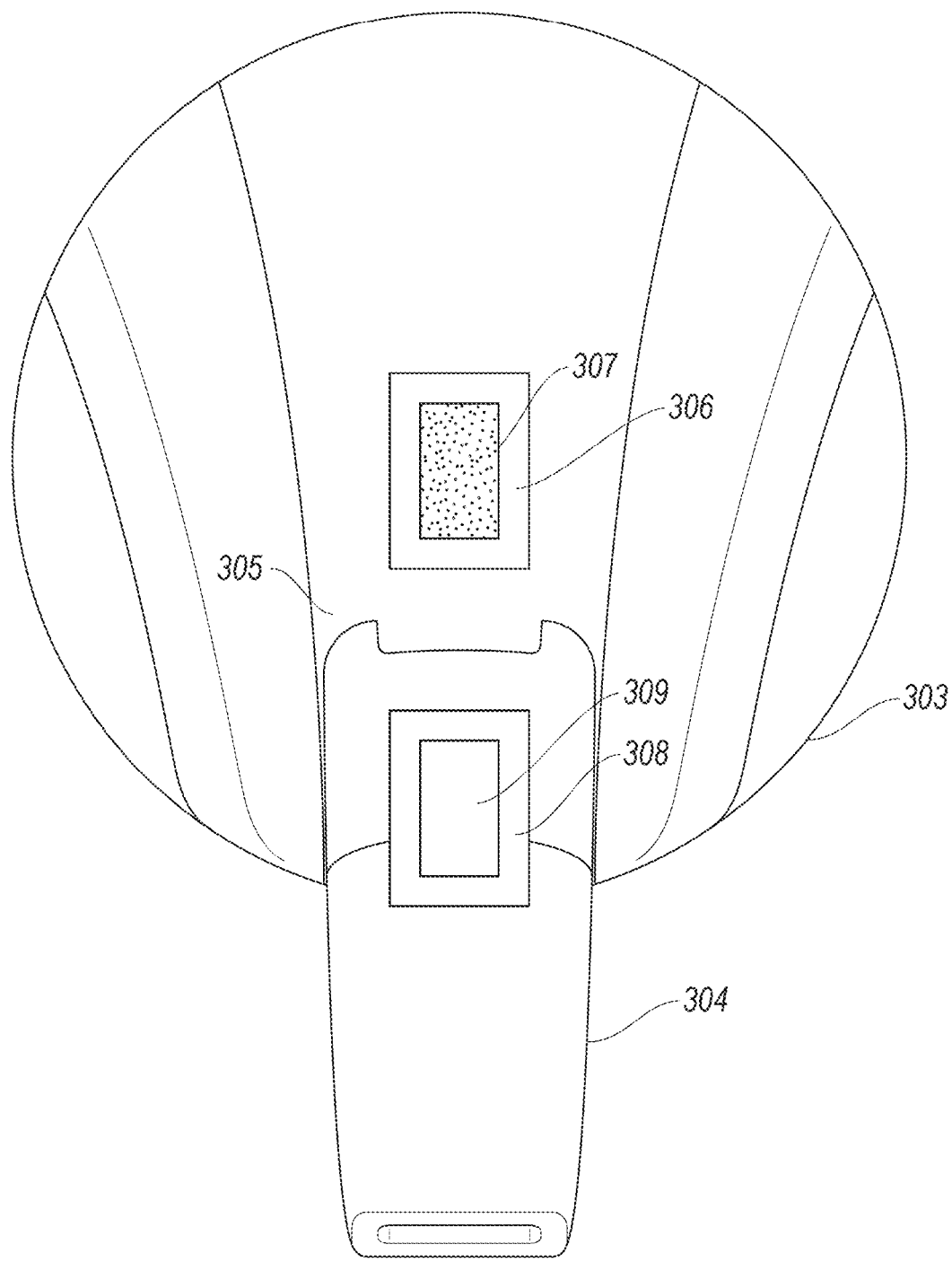

FIG. 3B shows one example positioning for the scented system in beverage container 301. Specifically, FIG. 3B shows a view down into cap 303 from directly above beverage container 301. As shown, cap 303 contains a hollow well 305 into which straw-type spout 304 folds when it is maneuvered into the "closed" position. The cap 303 includes a first encasement structure including a wall 306 that can be disposed on the floor of the well 305 in order to support scented article 307. The wall 306 forms an empty space or channel, within which the scented article 307 can be attached. As in other embodiments described herein, a scented article 307 protrudes above the top of wall 306, such that when straw-type spout 304 is in the elevated, "open" position, scented article 307 is exposed to the air. The cap 303 includes a second encasement including a corresponding wall 308 that is constructed along on the side of straw-type spout 304 to create an internal channel 309. Corresponding wall 308 is shaped to match wall 306, while internal channel 309 is shaped and sized to receive the protruding portion of scented article 307. Corresponding wall 308 is positioned such that when straw-type spout 304 is maneuvered to the closed position, corresponding wall 308 is lowered down over the top of scented article 307. Corresponding wall 308 touches wall 306 in this closed position, creating a contact seal that encloses scented article 307 inside it. In this manner, the first encasement structure and the second encasement structure provide a scent chamber or compartment wherein, when the straw-type spout 304 of the cap 303 is in the closed position, the contact seal created by the walls 306 and 308 encloses the scented article within the compartment and locks in and traps the scent within, allowing controlled release of the scent to the outer environment.

Although FIG. 3B shows scented article as an elongated shape running parallel to straw-type spout 304, one of skill the art would appreciate that, so long as both wall 306 and corresponding wall 308 are oriented to align, scented article 307 can be mounted parallel to, perpendicular to, or in any other orientation with respect to straw-type spout 304. Depending on the orientation of scented article 307 relative to straw-like spout 304, different shapes and sizes of scented article 307 may be appropriate. Scented article 307 can be attached to the bottle using any of the manners described elsewhere herein.

Figure 3C:
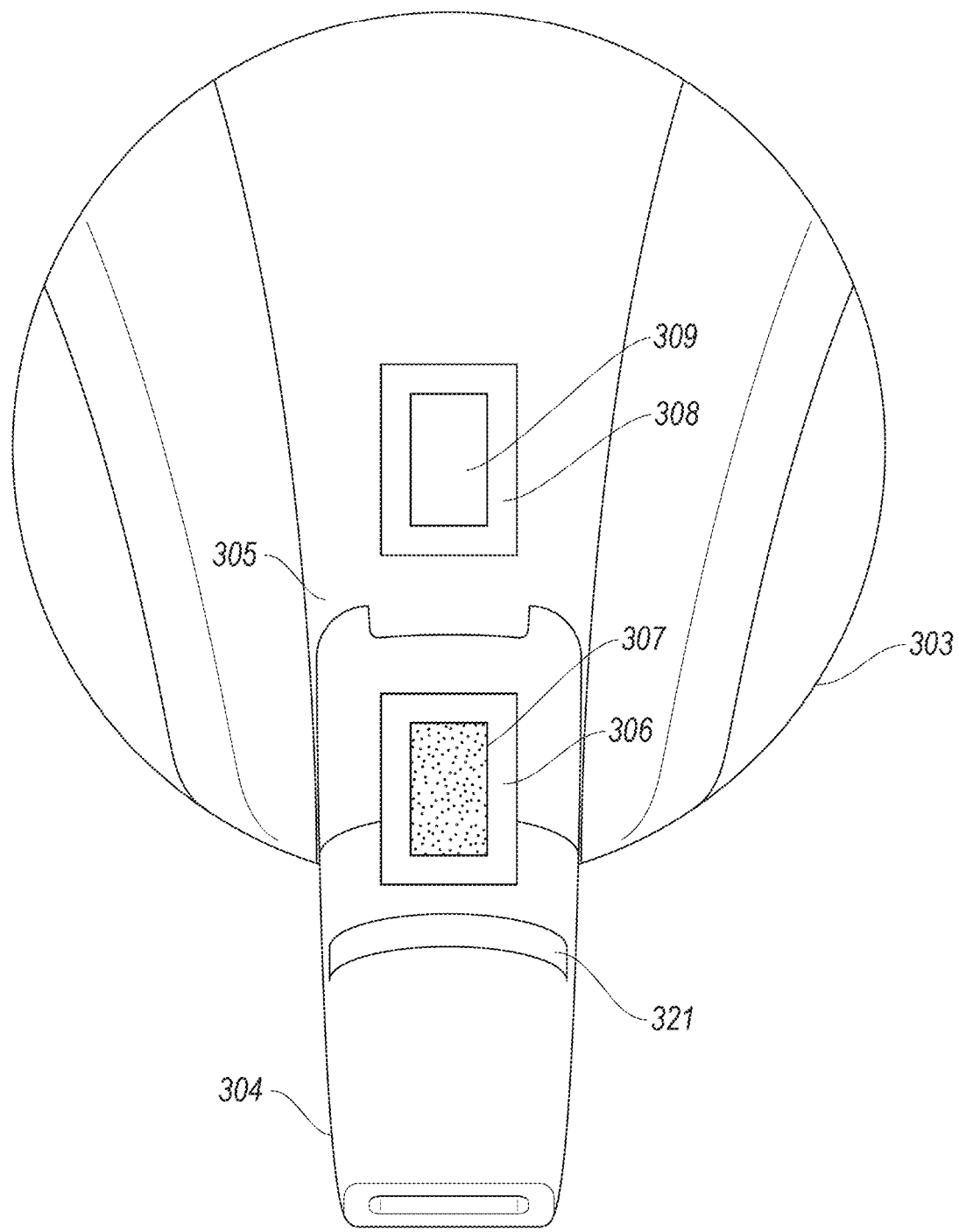

FIG. 3C shows an alternative embodiment of the system just described, in which the positions of wall 306 and corresponding wall 308 are reversed. In this embodiment, the first encasement structure with the scented article 307 is mounted on the straw-type spout 304. While the action of opening and closing the contact-sealed channel formed by wall 306 and corresponding wall 308 is identical to what was just described, in this embodiment, an optional shield 321 can be incorporated along straw-type spout 304 to avoid lip contact with the protruding portion of scented article 307. In some example, the shield 321 can include a perforated material to allow the scent from the scented article 307 to emanate through while protecting the scented article 307 from direct contact with the user's lip.

Figure 3D:
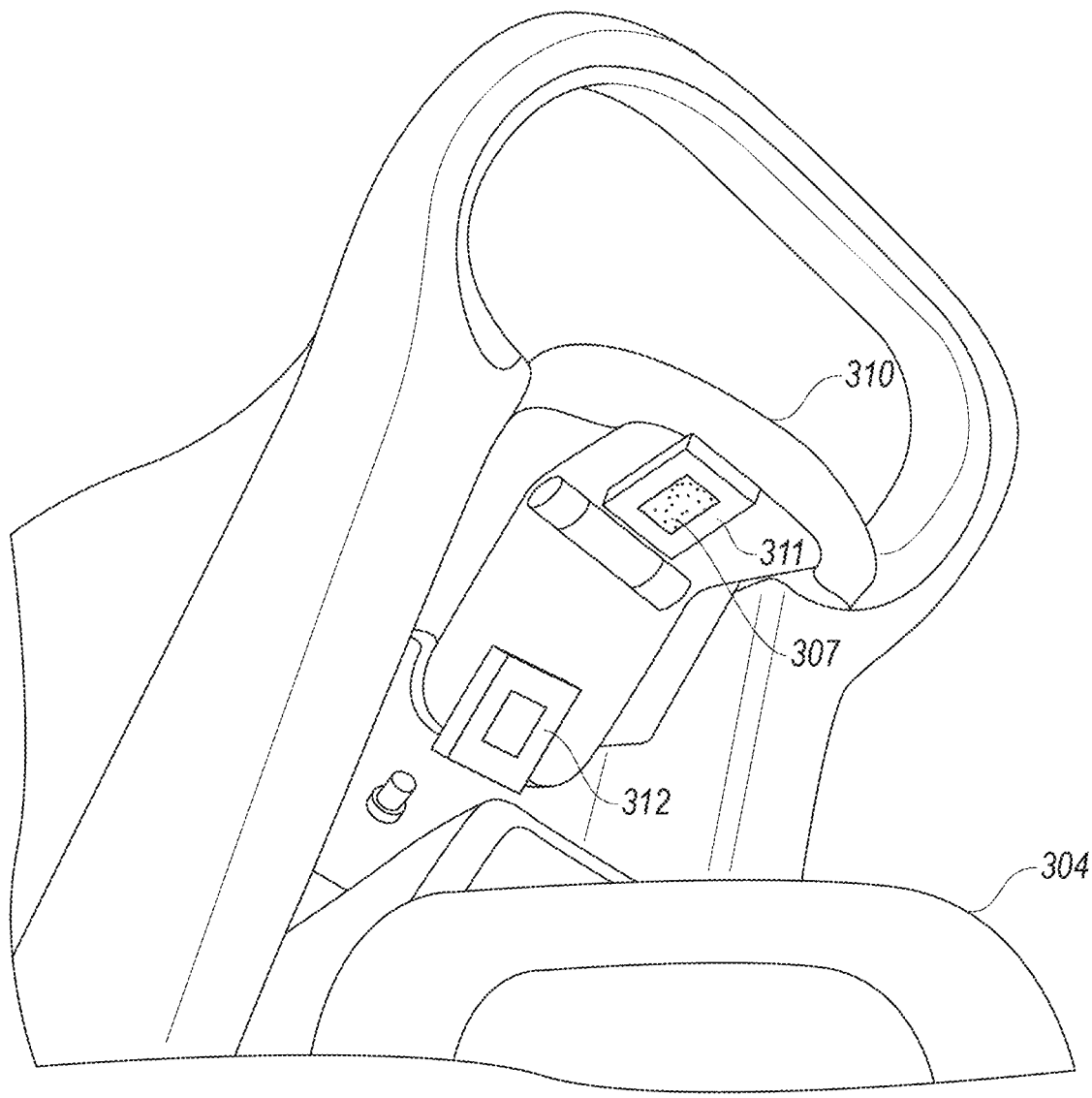

FIG. 3D shows still another alternative embodiment of a scented system applied to beverage container 301. FIG. 3D shows an elevated view from an angle down upon cap 303. In some instances, e.g., where straw-type spout 304 is spring-loaded, or where additional leak protection is desired, cover 310 can be incorporated to fold down over the tip of straw-type spout 304 when it is in the closed position. Cover 310 provides an additional site on which scented article 307 may be disposed. Specifically, wall 311 can be built on cover 310 to hold scented article 307. In such an embodiment, corresponding wall 312 can be constructed below wall 312 so as to receive the protruding portion of scented article 307 when straw-type spout 304 is maneuvered to the closed position. In some embodiments, the wall 311 and the corresponding wall 312 can be reversed such that scented article 307 is mounted on straw-type spout 304 and the internal channel 309 of the second encasement structure is on the cover 310. When either arrangement is moved to the closed position, the walls surrounding the scented article 307 and the corresponding walls receiving the protruding portion of the scented article form a contact seal to seal the scented article 307 inside. Once again, in FIG. 3D, a shield may be desirable between scented article 307 and the opening of straw-type spout 304, so that someone sipping from the spout does not make lip contact with scented article 307.

In each of these embodiments in FIGS. 3A, 3A-1, and 3B through 3D, scented article 307 can be attached to the side of the straw-type spout in one of the manners described herein, e.g., including but not limited to using the mechanisms shown in FIG. 1D. To allow for washing and drying of the straw-type spout between uses without damaging scented article 307, scented article 307 can be attached in a removable fashion. Moreover, the scented article can be constructed in any shape, so long as the surrounding walls expose a portion of the scented article to allow for dispersion of scent into the air and the corresponding walls will seal around it. For example, the scented article 307 can be configured as a ring that fits within the walls 311, 312, 308, or 306 and is therefore sealable by the corresponding wall, respectively.

Figure 4A:
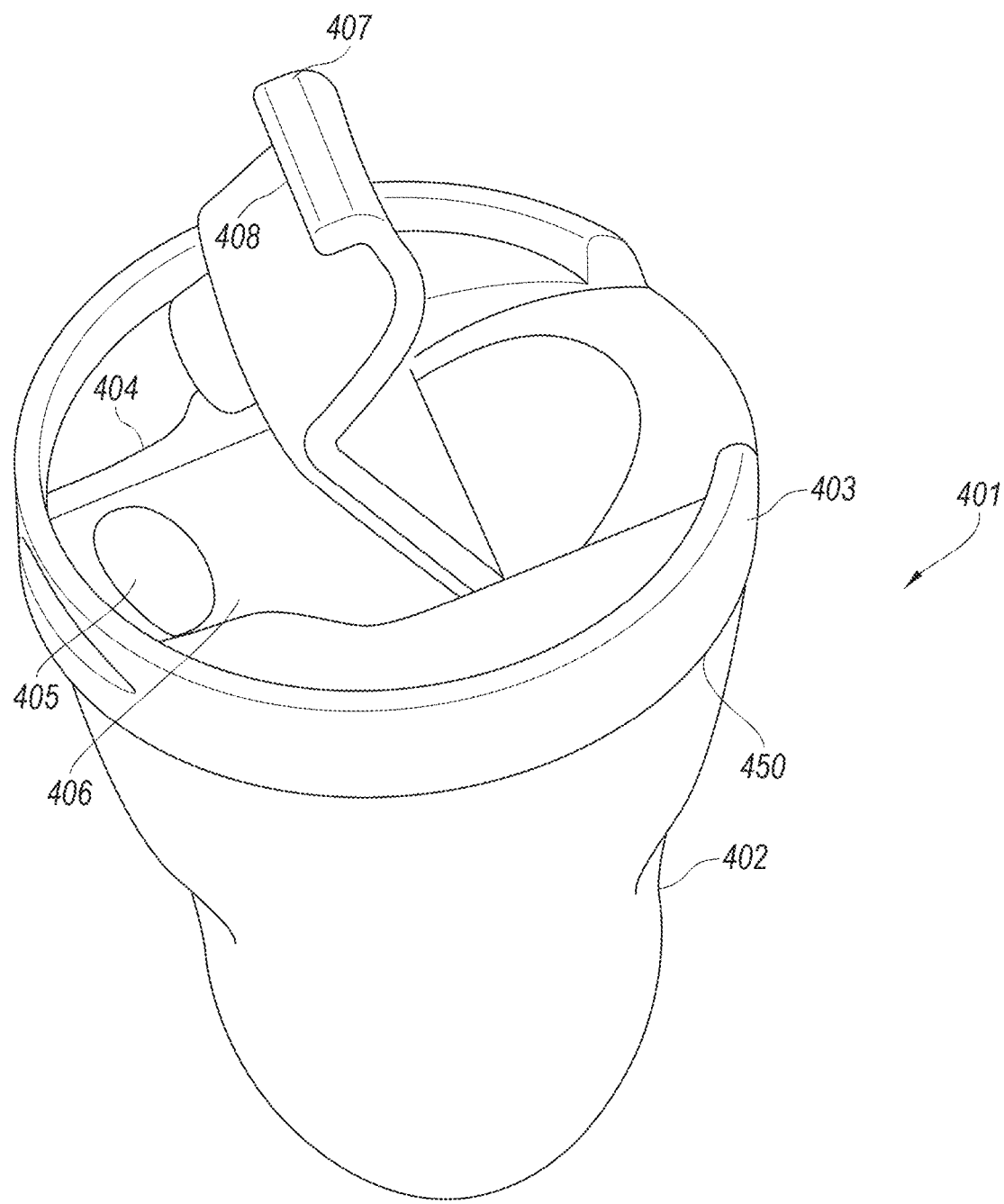
FIGS. 4A-4C show example embodiments of a scented beverage system including a scented article configured inside a sealable channel of a drinking container featuring a flip-cap spout.
Figure 4B:
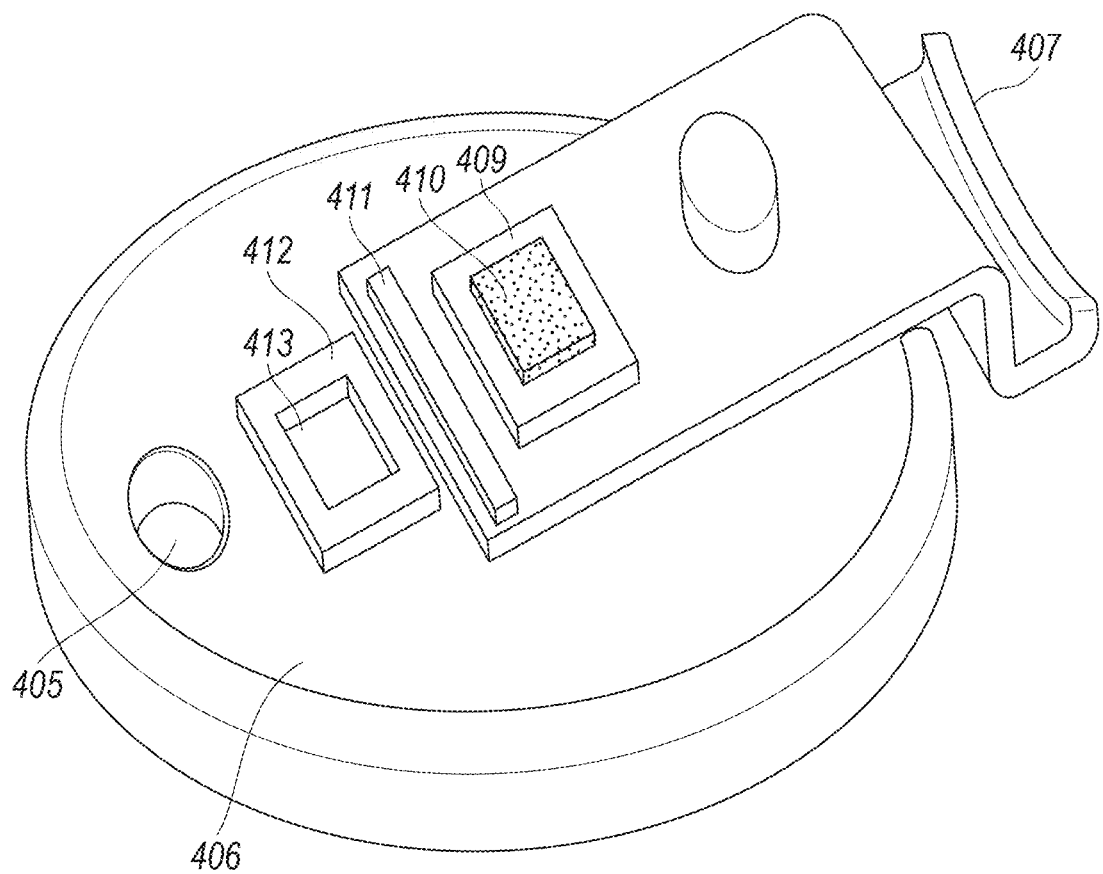
Figure 4C:
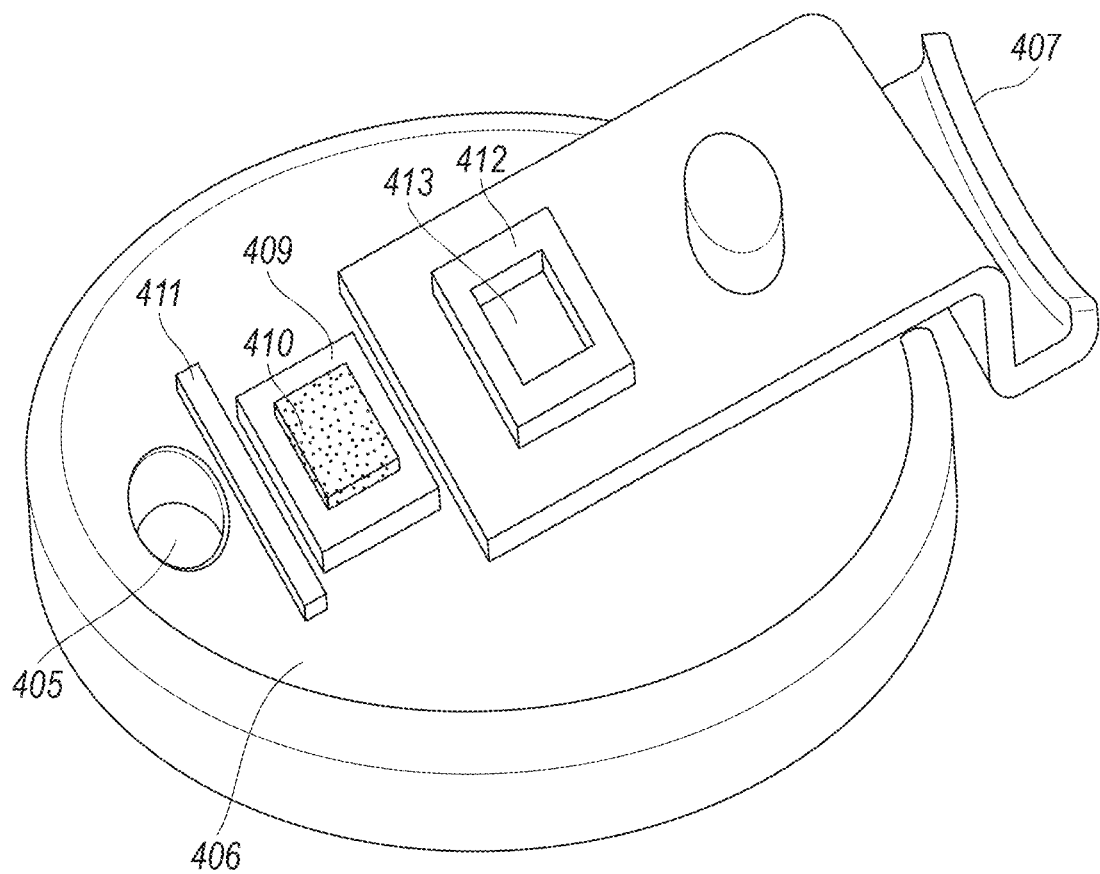

FIGS. 4A-4C show example embodiments of a scented system that can be applied to a beverage container utilizing a sealable flip-cap spout. Such flip-cap spouts are often utilized on so-called travel containers that people use to transport beverages while commuting and so forth. In these scenarios, spillage is also a concern, but a more specialized sports-type cap is not required. Moreover, such flip-cap type spouts and their containers are typically reusable, meaning they will be subject to the stresses of washing and drying repeatedly.

FIG. 4A shows beverage container 401. In particular, container 401 includes a container body 402 and cap 403. The cap 403 is fitted with a flip-cap spout 404 and is attachable to the body 402 via a threaded portion 450 between the cap 403 and the body 402. Specifically, flip-cap spout 404 includes an opening 405 in a fixed base 406 connected to the body 402 through which beverage can flow, and a movable component or assembly 407 (also referred to as "movable portion" 407). Movable portion 407 can move between a range of positions, such as an elevated position where the movable portion 407 is in an "open" position as shown so that a beverage can flow through the opening 405, and a lowered or "closed" position where the opening 405 is covered and liquid is trapped inside body 402. While not required, movable portion 407 may include a latch mechanism 408 to help lock it in the closed position.

Similar to other embodiments described herein, a scent-sealing compartment or chamber may be constructed on the cap 403 to hold a scented article beneath the movable portion 407. As shown in FIG. 4B, a first encasement structure includes a wall 409 that is created on the bottom surface of movable portion 407, which forms a channel that can support a scented article 410. Scented article 410 and wall 409 may be of any size or shape, so long as they match one another and a portion of the scented article 410 protrudes above wall 409 to expose scented article 410 to the air, e.g., on multiple sides. The greater the surface area of scented article 410 exposed to the air, the greater the dispersion of scent. In this way, when movable portion 407 is in the open position, as shown in FIG. 4B, the protruding portion of scented article 410 is in contact with the air and will be in proximity of the user's nose when the user sips from opening 405, while still being physically isolated from the beverage being sipped from opening 405 and the user's lips. In some embodiments, for example, an optional wall 411 can be included to help ensure separation between scented article 410 and the user's lip.

As shown in FIG. 4B, the cap 403 includes a second encasement structure including a corresponding wall 412 that is disposed on fixed base 406. In the example, the corresponding wall 412 matches the shape of wall 409 and contains a cavity or receiving channel 413 capable of receiving the protruding portion of scented article 410. In this way, when movable portion 407 is lowered into the closed position, corresponding wall 412 contacts wall 409, creating a contact seal in the manner described elsewhere herein and trapping scented article 410 inside. In this manner, the first encasement structure and the second encasement structure provide a scent chamber or compartment wherein, when the movable portion 407 of the cap 403 is in the closed position, the contact seal created by the walls 409 and 412 encloses the scented article 410 within the compartment and locks in and traps the scent within, allowing controlled release of the scent to the outer environment.

In some embodiments, the corresponding wall 412 may be flat, or even recessed into the fixed base with the receiving channel 413, and the wall 409 is structured to have a height such that wall 409 still encloses scented article 410 when movable portion 407 is in the closed position.

Like the other embodiments described herein, for example, the placement of the scented article in this embodiment may be reversed such that first encasement structure with the scented article 410 is mounted inside wall 409 located on the fixed base 406, while the second encasement structure including the corresponding wall 412 is constructed on the bottom surface of movable portion 407. This type of arrangement is show in FIG. 4C. In such an arrangement, wall 411 may be included on fixed base 406 in order to help ensure separation between scented article 410 and the user's lips when positioned at opening 405.

Scented article 410 can be attached to the flip-cap spout in one of the manners described herein, e.g., including but not limited to using the mechanisms shown in FIG. 1D. To allow for washing and drying of the flip-cap spout between uses without damaging scented article 410, for example, the scented article 410 can be attached in a removable fashion. Moreover, scented article 410 can be constructed in any shape, so long as the surrounding walls expose a portion of the scented article to allow for dispersion of scent into the air and the corresponding walls will seal around it. For example, the scented article 410 can be configured as a ring that fits within the walls 409 or 412 and is therefore sealable by the corresponding wall, respectively.

Figure 5:
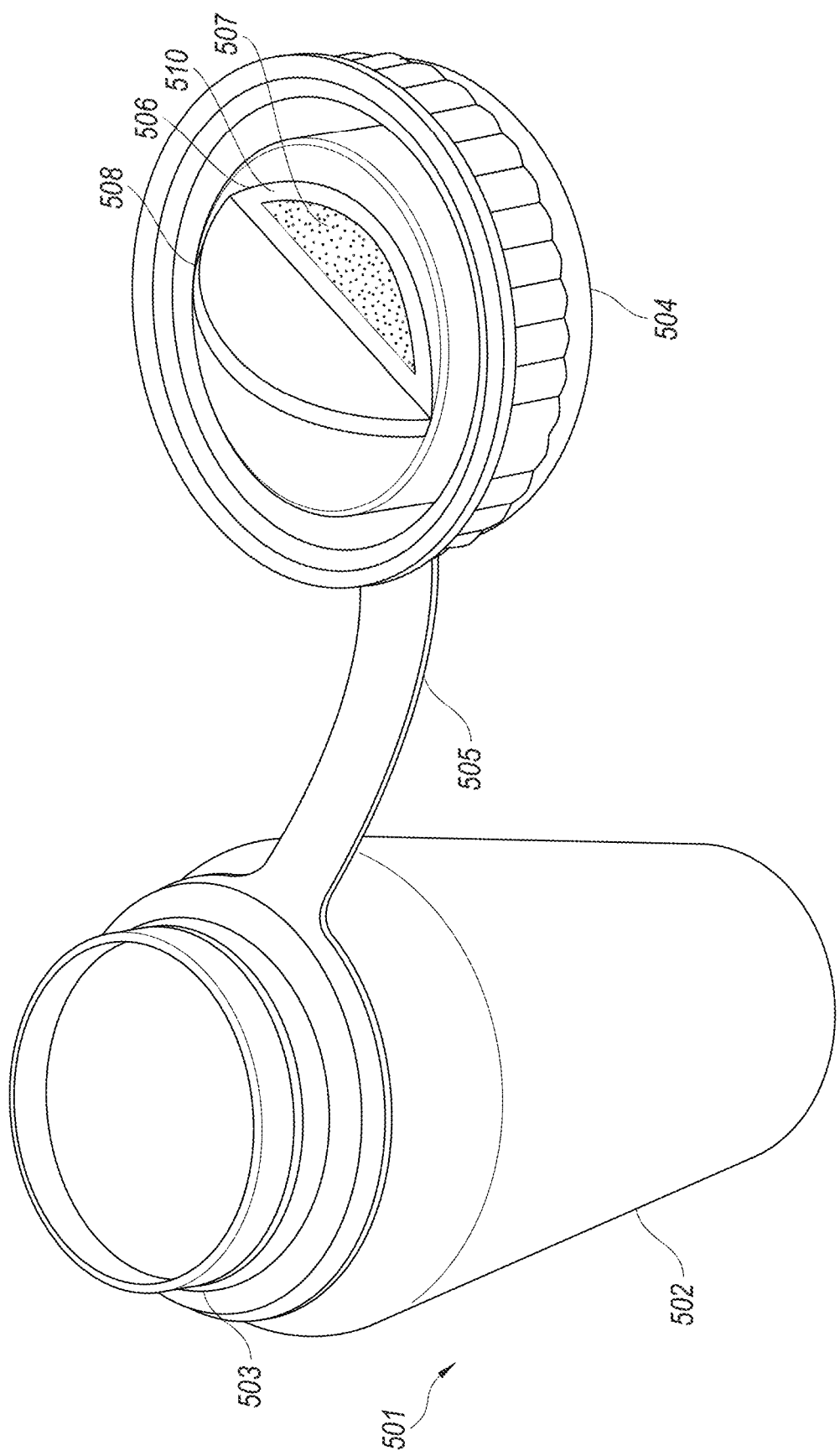
FIG. 5 shows an example embodiment of a scented beverage system applied to a beverage container containing a screw-down lid.

FIG. 5 shows an example of a scented system that can be applied to a beverage container containing a screw-down lid. Such screw-down lids may be preferable on thermoses and other, similarly insulated containers designed to maintain the temperature of chilled or heated beverages. To prevent heat transfer, the lids in these containers can be constructed of rigid, non-conductive material, and have a threaded sealing mechanism. Because these containers may be designed for repeated use, frequent washing may be necessitated. Unlike the other embodiments described previously, users consume the beverage from these types of containers by placing their lips directly against the opening; there is no spout structure utilized, and as such, there is no obvious place to incorporate a scented system.

As shown in FIG. 5, a beverage container 501 includes a container body 502 and a cap 504. Cap 504 is tethered to the container body 502 by way of strap 505 and can attach to the container body 502 by snapping or screwing down onto a threaded neck 503, for example. Cap 504 also includes a sealable compartment or chamber 506 in its bottom surface. Sealable chamber 506 includes an encasement structure to provide a channel or space for a scented article 507 and a moveable component 508 to move between an open and closed position with respect to an outer wall 510 surrounding the channel where the scented article 507 is encased. In some embodiments, the movable component 508 includes a door. In such examples, door 508 can be constructed to open and close in a number of ways, including manually or by being spring-loaded to open when cap 504 is removed from container body 502. Regardless of the closure mechanism, movable component 508 may be exposed to the beverage inside body 502 when the cap is closed, such that the movable component (e.g., door) 508 makes a waterproof seal with the outer wall of the encasement structure when covering the sealable chamber 506. In this manner, the encasement structure and the movable component provide the chamber wherein, when the movable component 508 of the cap 504 is in the closed position, the contact seal created by the wall 510 and the movable component 508 encloses the scented article 507 within the chamber and locks in and traps the scent within, allowing controlled release of the scent to the outer environment.

While the sealable chamber 506 and the scented article 507 can be made in any shape relative to cap 504, scented article 507 can be attached in one of the manners described herein, e.g., including but not limited to using the mechanisms shown in FIG. 1D. To allow for washing and drying of beverage container 501 between uses without damaging scented article 507, for example, the scented article 507 can be attached in a removable fashion. For example, the scented article 410 can be configured as a ring that fits within the sealable chamber 506.

FIGS. 6A, 6B-1, 6B-2, 6C, and 6D show an example of a scented system that can be applied to a beverage container utilizing a straw lid. Such containers are often used in replacement of disposable plastic cups and straws in order to reduce the accumulation of plastic waste in the environment. They feature thicker, more rugged walls in both the cup and the straw, and both must be capable of being washed in order to allow for reuse.

Figure 6A:
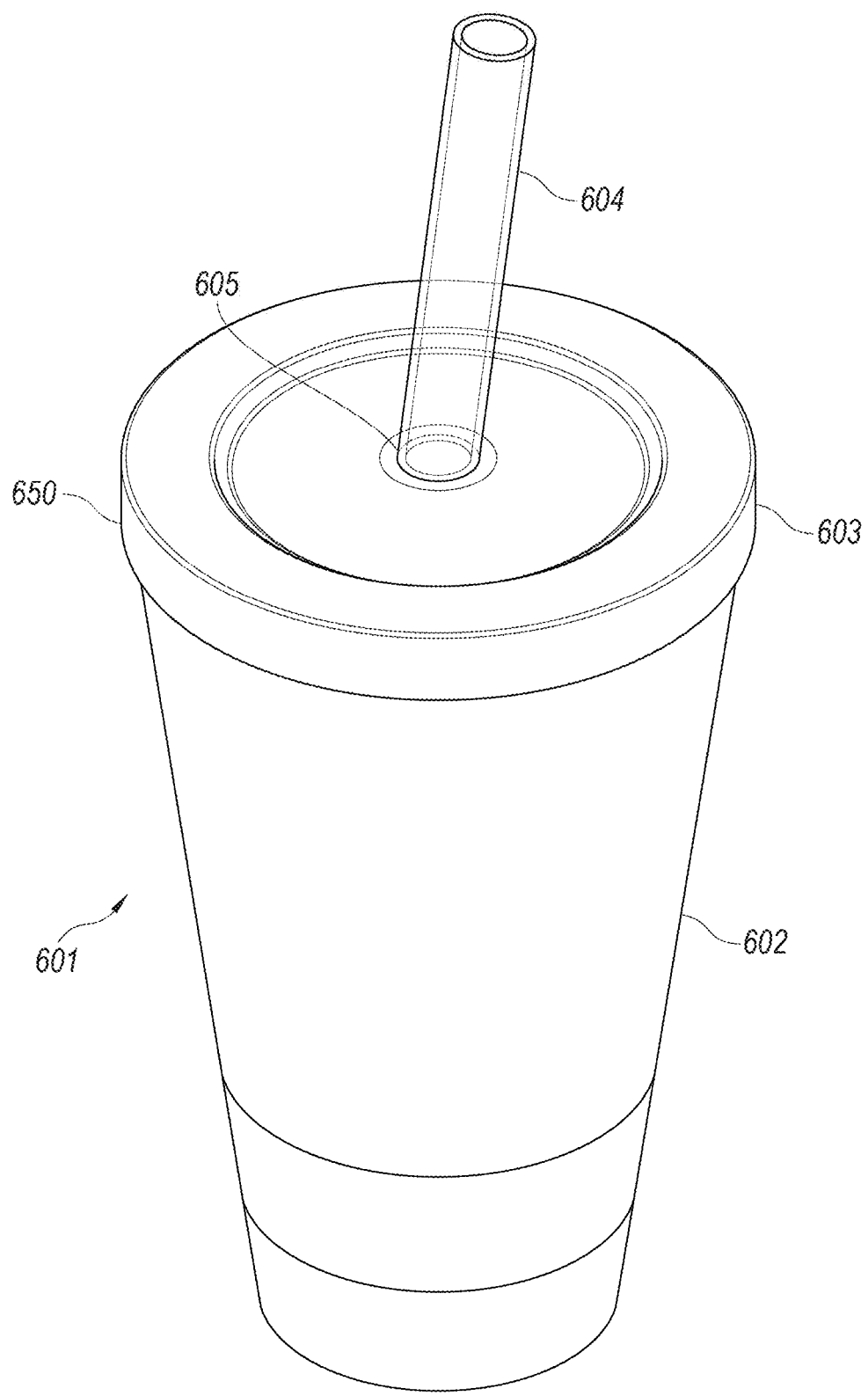

FIG. 6A shows beverage container 601, which includes a container body 602 and a lid 603. Lid 603 accommodates a straw 604 through a hole 605 and screws onto a threaded region 650 on the container body 602. While previous systems such as container 601 have attempted to utilizing scented articles by applying them at the lid, that leaves the scented article far from the user's nose. Thus, the embodiments disclosed here deploy the scented article much closer to the user's olfactory sensors by placing it on the straw. For example, the scented article can be configured within an optimal distal range from the opening of the straw 604, e.g., between 2 inches to 0.5 inches away from the opening, so that the scented article is proximate the user's nose when the beverage is being consumed through the straw 604. This presents a challenge in terms of mounting and sealing the scented article.

Figures 1, 6B:
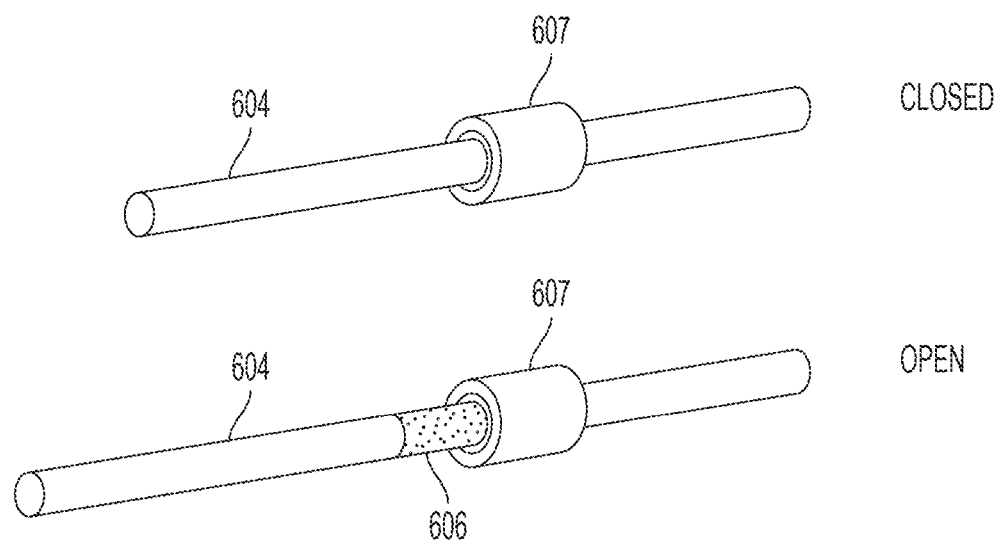

FIG. 6B-1 shows one example embodiment designed to overcome this obstacle. Straw 604 includes a scented article 606 attached to it and a cover 607 to provide a movable encasement that forms a sealable chamber to trap the scent emanated by the scented article for controllable release. In some embodiments, scented article 606 can be a cylinder or ring, whose internal diameter is just slightly larger than the outer diameter of straw 604. Cover 607 can be configured as a cylindrical piece of just slightly larger internal diameter than scented article 606. When drinking from straw 604, cover 607 may be slid up or down straw 604 into an "open" position in order to expose scented article 606 to the air. When straw 604 is not in use, cover 607 may be slid back down into a "closed" position over scented article 606 to protect it. In some embodiments, a lip of straw material can be added to straw 604, e.g., below scented article 606, such that when cover 607 is "closed," it contacts the lip of straw material to seal in the scented article 606.

Scented article 606 is shown as a complete cylinder with a ring-shaped cross-section, which can be slid over one end of straw 604 and attached to straw 604 by the use of adhesives or through one of the other attachment mechanisms described herein, e.g., in FIG. 1D. In some implementations, for example, the scented article 606 can alternatively be constructed as a partial cylinder with C-shaped cross-section that can snap directly over the side straw 604. Scented article 606 should be positioned on straw 604 close enough to one end that scented article 606 will be in proximity of the user's nose while the user is sipping from straw 604.

Figures 2, 6B:
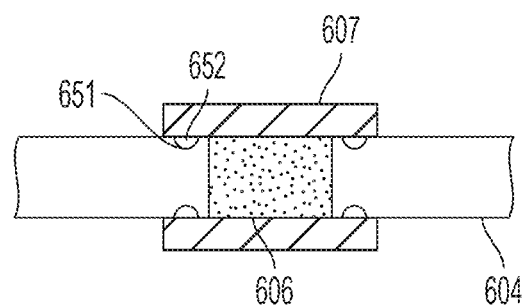

While cover 607 can protect scented article and remain in place strictly through friction against scented article 606, cover 607 may also utilize a locking mechanism to hold in place. FIG. 6B-2 shows a cross section of straw 604, cover 607, and the scented article 606. Straw 604 can be constructed with one or more grooves, 651, while cover 607 can be constructed with a corresponding tongue 652 to match each groove. When cover 607 is slid into the closed position over scented article 606, tongue 652 will pop into groove 651, creating a contact seal around scented article 606.

Figure 6C:
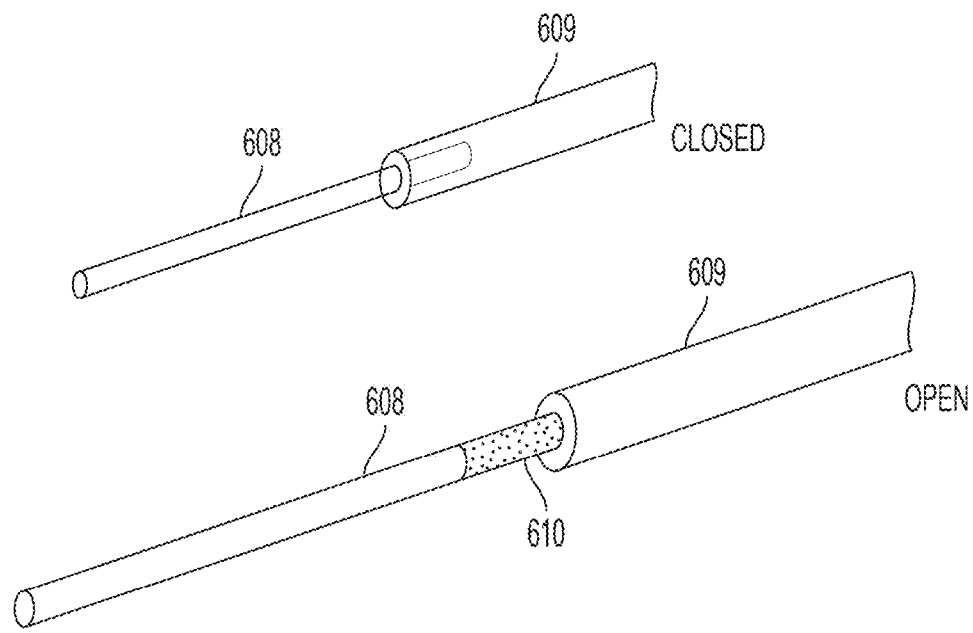

FIG. 6C shows an alternative embodiment by which a scented article can be disposed on straw 604. In FIG. 6C, a close-up of straw 604 reveals that it can be constructed from two, separate pieces, inner straw 608 and outer straw 609. As FIG. 6C depicts, the inner diameter of outer straw 609 is just slightly greater than that the outer diameter of inner straw 608. In this way, they fit together snugly, but with the capability of moving relative to one another when force is applied along an axis perpendicular to those diameters. In the example embodiment, an upper portion of inner straw 608 includes a scented article 610. In some examples, scented article 610 is likely to be configured as a cylinder or ring shape sized so that it will surround inner straw 608 without collapsing it while still fitting within the inner diameter of outer straw 609. Outer straw 609 may be positioned in an "open" position that exposes scented article 610 to the air, or a "closed" position in which scented article 610 is protected underneath outer straw 609. In some embodiments, a lip of straw material can be added to straw 608, e.g., below scented article 610, such that when outer straw 609 is "closed," it contacts the lip of straw material to seal in the scented article 610.

As in the embodiments shown in FIGS. 6B-1 and 6B-2, the scented article in FIG. 6C may be a complete cylinder with a ring-shaped cross-section, or a partial ring with a C-shaped cross-section that can be attached to inner straw 608 in the same manners as described in reference to those figures. In various embodiments of the straw 604 shown in FIG. 6C, the scented article 610 can be located on inner straw 608 in a position where it will be in proximity to the user's nose when sipping from the straw.

Figure 6D:
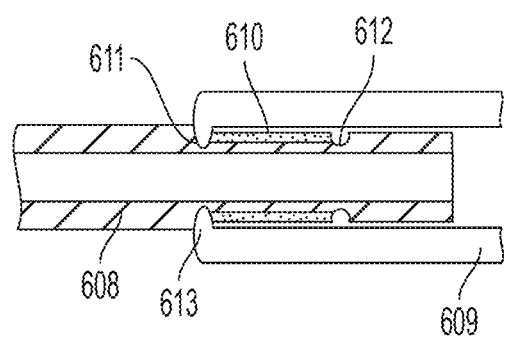

FIG. 6D shows a diagram of the example embodiment of the straw 604 from FIG. 6C in more detail regarding the sealing mechanism, e.g., showing inner straw 608, outer straw 609, and scented article 610 in a cross-sectional view. In this example, inner straw 608 is constructed with a lower groove 611 and an upper groove 612. Outer straw 609 is constructed with a tongue ridge 613 protruding into its internal diameter. Tongue ridge 613 is capable of fitting within both lower groove 611 and upper groove 612. When outer straw 609 is in the "closed" position, tongue ridge 613 will be positioned in lower groove 611 and scented article 610 will be covered. To expose scented article 610, force is applied in a direction perpendicular to the diameter of the straws and toward upper groove 612. Tongue ridge 613 will be displaced from lower groove 611 and slide up inner straw 608 until reaching upper groove 612. Tongue ridge 613 will drop into upper groove 612, locking outer straw 609 in place and exposing scented article 610. Applying force in the opposite direction will reverse the process and seal scented article 610 between inner straw 608 and outer straw 609. Significantly, because of the contact seal between inner straw 608 and outer straw 609, beverage will never contact scented article 610. Nor will the user's lips, which will be disposed at a far end of the straw, even though scented article is located within close proximity to user's nose.

FIGS. 7A-1, 7A-2, and 7B-7D show example embodiments of a scented system that can be applied to a beverage container utilizing a pop-top lid. Such pop-top lids are commonly deployed on aluminum beverage cans. These cans are typically meant to be disposed of or recycled following consumption of the beverage inside. Therefore, such beverage systems typically do not need to stand up to the rigors of being washed between uses. Nevertheless, such systems present a challenge for combination with a scent system given the limited real estate available on the can.

FIG. 7A-1 shows such a beverage container 701. Pop-top lid 702 includes a raiseable tab 703 connected to the container by way of a flexible portion 704 that is connected to the top surface 705 of the container 701. Lifting raiseable tab 703 applies a downward force against tear-away cover 706, pushing it into container 701 and thereby creating an opening through which the beverage can be consumed.

In some embodiments, raiseable tab 703 contains a finger ring 707 to assist the user in grabbing and pulling on it. Finger ring 707 can be created by bending some of the aluminum back under tab 703. Given this example construction, FIG. 7A-2 depicts how a scented article 709 can be placed within the finger ring 707, held in place by this bent-under aluminum. In this example embodiment, before the container 701 is opened, the scented article 709 is sealed against top surface 705 by the downward pressure of tab 703. When tab 703 is raised to open container 701, scented article 709 is exposed to the air. In this manner, the bottom surface of tab 703 can provide a movable encasement of the scented article 709 that is sealed to trap the scent when pressed against the top surface 705, such as during the manufacturing process of the beverage container 701 or bottling process of the beverage into beverage container 701. Notably, while the scented article 709 cannot be resealed in this embodiment, e.g., because container 701 will likely be discarded or recycled as soon as the beverage inside is consumed, the user should not experience any significant diminishment in scent performance.

Figure 7B:
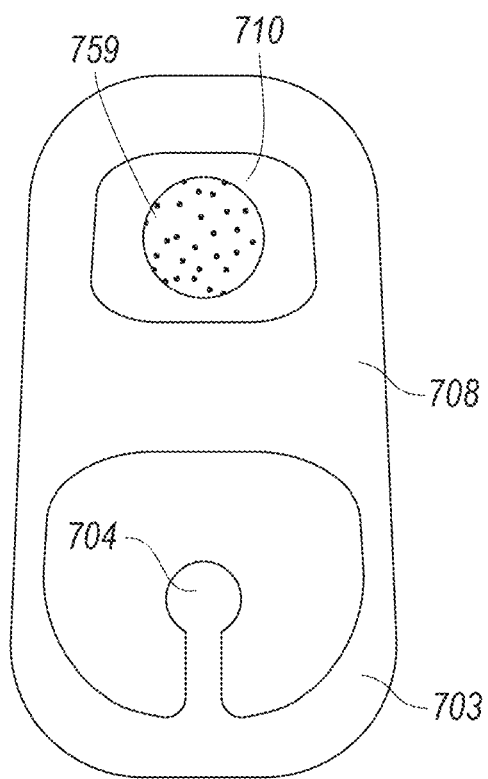

FIG. 7B shows another embodiment of how a scent system can be deployed on such a container like the container 701 with a pop-top lid. Specifically, FIG. 7B shows a view of the underside of tab 703. Instead of utilizing a finger ring, the end of tab 703 opposite of flexible portion 704 in this embodiment is a flat, solid region 708. In this solid region 708, a scented article 759 is affixed to the underside of tab 703. The sides of scented article 759 are surrounded by an encasement that includes a wall 710 to form a channel in which the scented article 759 is contained. After manufacturing of the pop-top lid with the container, the encasement including the wall 710 and scented article 759 begin affixed to the top surface 705 of container 701 and to the underside of tab 703. In this way, scented article 759 is completely encased before container 701 is opened. When tab 703 is raised to open container 701, wall 710 breaks away from top surface 705, exposing the scented article 759 to the air. Positioned in this way, the scented article 759 is in close proximity to the user's nose when a drink is taken from the container 701. Alternatively, scented article 759 and the encasement including the wall 710 may be affixed to top surface 705, instead of tab 703; in such a case, all of the other aspects of the embodiment can be maintained and function identically. As with the previous embodiment, the embodiment in FIG. 7B would not be resealable, but instead could be disposed/recycled as soon as the beverage inside container 701 was consumed. Notably, for example, the walls in this embodiment can be constructed of the same aluminum as container 705, or separately constructed from plastic or foil that is applied during assembly.

Figure 7C:
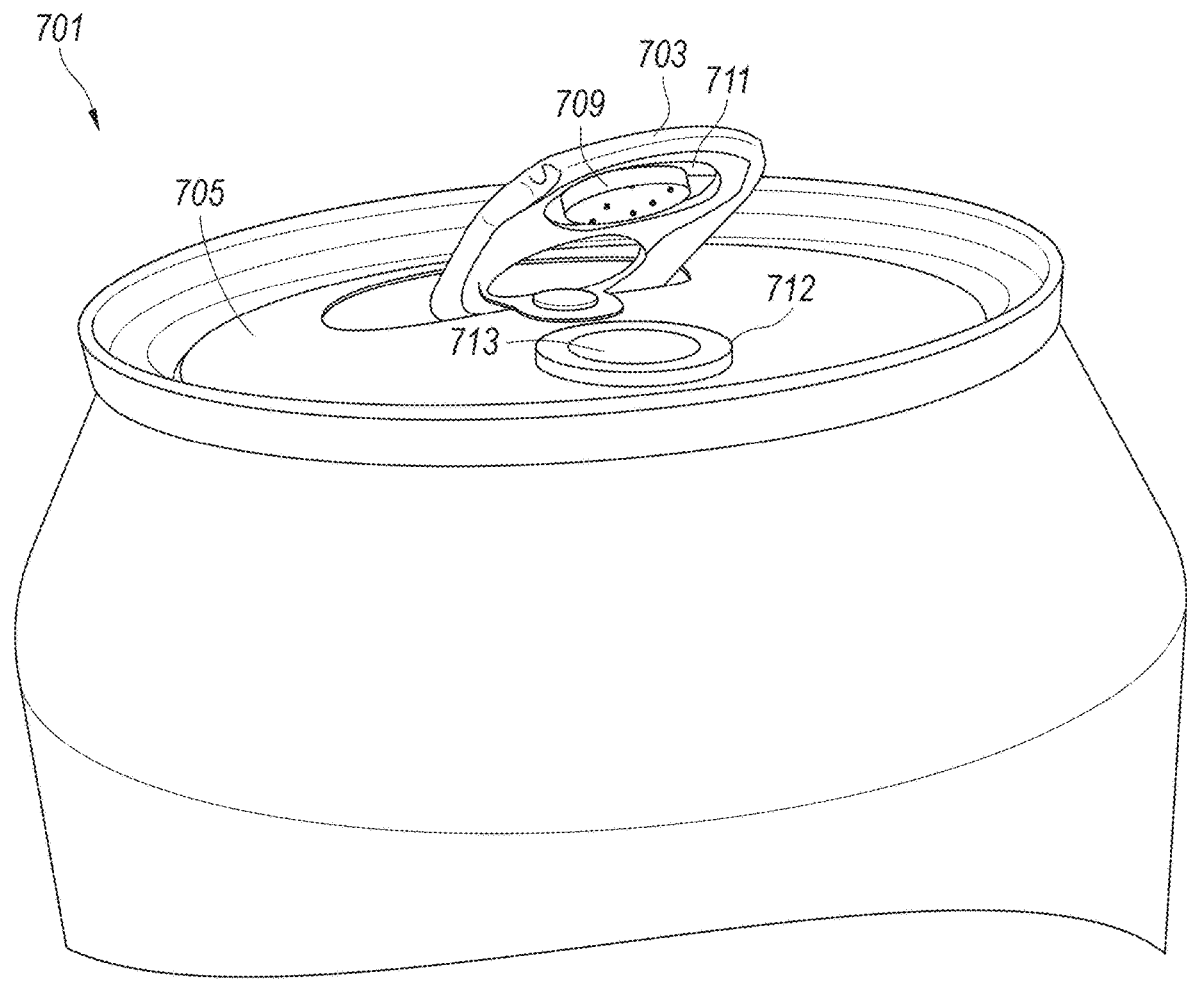

FIG. 7C shows a variation of the previous embodiment in which the scented system would be resealable. Specifically, FIG. 7C shows a rotated view of the top surface 705 of container 701 with tab 703 raised. Scented article 709 is located inside a wall 711 such that portion of scented article protrudes from wall 711. Below wall 711, arranged to match its shape but have an inner diameter just larger than the outer diameter of wall 711 is corresponding wall 712. Corresponding wall 712 contains a channel 713 of a shape and depth that it can receive the protruding portion of scented article 709. When originally assembled, scented article 709 is sealed inside wall 711 and corresponding wall 712, which are fused but perforated to separate when tab 703 is raised. After container 701 is opened by raising tab 703, tab 703 can be pressed back down so that the inner circumference of corresponding wall 712 engages with the outer circumference of wall 711 and the friction between them is sufficient to hold channel 713 closed.

While corresponding wall 712 has been depicted as being raised off the top surface 705, one of ordinary skill would appreciate that corresponding wall 712 could just as easily be constructed as a depressed area on top surface 705. Similarly, one of ordinary skill in the art will also appreciate that the relative positions of scented article 709, wall 711, and corresponding wall 712 could be reversed such that scented article 709 and wall 711 are disposed on top surface 705 rather than on the bottom surface of tab 703, and they engage corresponding wall 712 which is mounted on the bottom surface of tab 703. As with the previous embodiment, the walls in this embodiment can be constructed of the same aluminum as container 701, or separately constructed from plastic or foil that is applied during assembly.

Figure 7D:
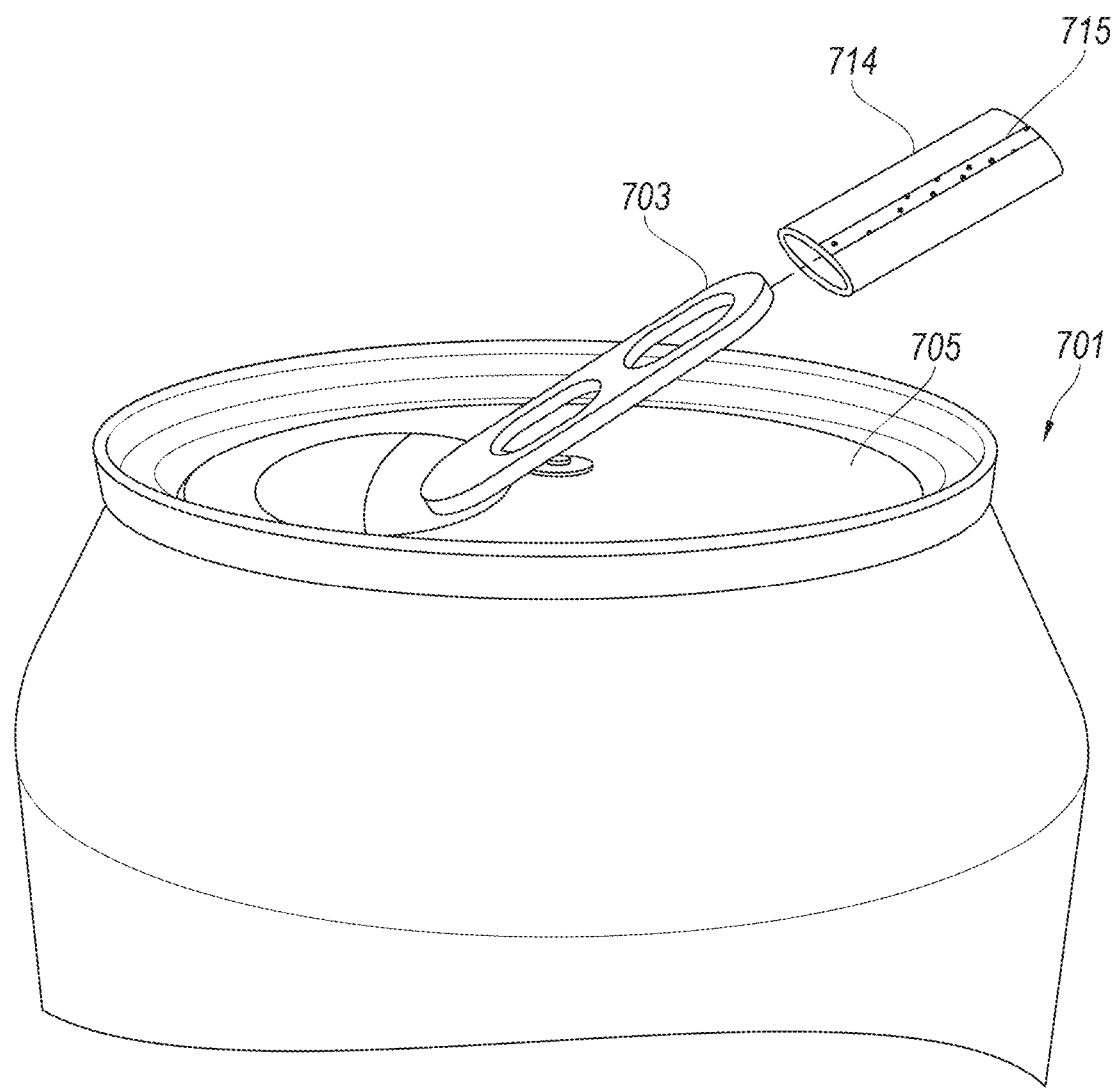

FIG. 7D shows a final embodiment for applying a scented system to such a beverage can. Sleeve 714 is designed to be slightly larger in width and thickness than tab 703. Open at least one end, sleeve 711 can slide over tab 703 once tab 703 is raised away from top surface 705 to open container 701. Sleeve 714 contains scented article 715 mounted on its surface so that, once sleeve 714 is mounted on tab 703, scented article 715 will be in close proximity to the nose of a user consuming the beverage from container 701. In this embodiment, or any of the other embodiments discussed in FIGS. 7A-1, 7A-2, and 7C, the top of the container 701 can be covered in a plastic wrap or foil to add to the seal and assist in preservation of the scented articles during assembly, transit, and in the retail environment prior to being opened.

The example embodiments described above include features that address and balance a number of design tradeoffs and challenges presented when engineering and constructing containers for beverage consumption to augment a user's drinking experience by delivering a scent from the container or container's appendage using a scented article. For example, the scented article should be able to deliver scent reliably to the consumer of the beverage repeatedly across multiple uses, even as the container is exposed to various environmental stressors such as heat, cold, and/or washing. The scented article may be presented in close proximity to the consumer's nose while the consumer is drinking the beverage, but it is optimal that neither the beverage nor the consumer's lips should physically touch the scented article. The scented article should be maintained a consistent distance from the user's nose no matter how the container is used so that the intensity of the scented article can be calibrated to be strong enough to stimulate a sense of taste but not so strong that it will antagonize the user and those in a proximate environment of the user. The scented article should be sealable to preserve the scent during product manufacturing, shipping and storage to prevent cross-contamination of scents from the same or differing scented articles in proximity to the product. The scented article should be large enough to hold a sufficient amount of scent such that it can stimulate a sense of taste, while small enough to minimize construction materials and integrate and attach to the beverage container in the precise location to optimally deliver and preserve the scent. The location of the scented article should expose enough surface area that scent is released with sufficient intensity to stimulate a sense of taste. Moreover, different types of containers serve varying functions, and those functions must still be satisfied despite the additional delivery of the scent from the scented article to the consumer. The above example embodiments of the scented articles and beverage containers are engineered to overcome at least some if not all of these challenges to provide the associated benefits to the user to create an enjoyable drinking experience through controlled delivery of a scent for augmenting the user's taste perception.

Scented Materials for Scented Articles in Beverage Containers

As discussed above, the ability to control scent delivery and preserve the scent for repeated scent deliveries by the particular bottle container may also be impacted by the materials engineered to form the scented article. For the example scented articles to be attachable to and/or incorporated in a drinking container, the scented article typically requires a small size relative to the container structures (e.g., bottle and/or cap of the drinking container), and therefore limited surface area, while also possessing a durable, solid structure to prevent unintentional detachments from the container (e.g., which could cause choking), unwanted leaching of chemicals into a beverage, or unintended uses (e.g., user eating the scented article) and, all the while, must still provide a strong-enough scent for the user to smell while consuming the beverage, but not too-strong of a pungent scent to adversely affect the user's beverage experience. For the scented article to achieve such functionality with a small size and sufficient structure, the fragrance composition that creates the scent in the scented article should be loaded at and must maintain a sufficient concentration range in the base material to produce a robust, stable scented product suitable for applications like scented beverage container systems.

Example embodiments of scented materials to produce the scented articles can include a fragrance material (e.g., such as a fragrant or scented compound in the form of an oil, emulsion or other liquid or liquid like phase) incorporated into a base material (e.g., a plastic). In some examples, the fragrant compounds are engineered to be compatible with certain polymer base materials, such as polyolefin, in which the fragrant compounds are integrated into the base material at particularly high loads, such as in % wt ranges of 10% or greater, e.g., 10-30% fragrant compound. The fragrant material can include an odorless flavor carrier compound and a scent flavor compound, which can be formed as a scented oil. In some embodiments, the odorless flavor carrier compound includes medium chain triglyceride (MCT) and Triacetin (1,2,3-triacetoxypropane). In such embodiments, for example, the flavor or fragrance material, such as fragrance oil, includes MCT, Triacetin, and the scent-flavor compound, in which the MCT includes a % wt in a range of 50-80% wt, the Triacetin includes a % wt in a range of 15-25% wt, and the scent-flavor compound includes a % wt in a range of 1-30% wt. In some examples, the fragrance oil includes MCT at a 50-70% wt range (e.g., 60% wt), triacetin at a 15-25% wt range (e.g., 20% wt), and the scent-flavor compound at 15-25% wt range (e.g., 20% wt).

In various embodiments of scented articles in accordance with the present technology, for example, the scented article can include the scented material (e.g., fragrance material incorporated into a base material) that has an exterior surface that includes cavities (e.g., pores, troughs, etc.) that recede inward with respect to the exterior surface of the scented article and/or protrusions (e.g., bumps, ridges, etc.) that protrude outward with respect to the surface of the exterior surface. In various embodiments, for example, the scented article can include a uniform exterior surface of the scented material. In various embodiments, for example, the cavities, protrusions, and/or uniform surface can be organized along the surface of the scented article in a variety of arrangements, e.g., including an array of periodic or aperiodic positioning, or randomly. For example, the scented article can include certain regions of the exterior surface to have cavities, the protrusions and/or the uniform surface; and/or the exterior surface can have a mixture of the cavities, the protrusions, and/or the uniform surface. In implementations, for example, the cavities and/or protrusions provide additional surface area to the scented article that can increase the concentration of the scent exposed to the outer environment (e.g., air), and thereby enhance the delivery of the scent to the user. In some embodiments, for example, the cavities and/or protrusions can be used to create letters, shapes, or symbols as a form of advertising or product differentiation.

In some embodiments, the scented articles can contain the scent by various methods and materials, including incorporating the scent into the material of the article, e.g., during a fabrication process to produce the article, as described in U.S. Pat. No. 9,801,969B2, entitled "SCENTED ATTACHMENT FOR CONTAINERS", the entire content of which is incorporated by reference in this patent document. For example, the scented article (e.g., scented ring) can be fabricated using a plastic material, e.g., polyethylene, polyurethane or other example materials described herein, that is loaded with the odorous compound or aggregate that produces the scent to a desired concentration, e.g., which can be selected based on multiple variables including the type of scent (e.g., degree of pungency of a particular scent).

EXAMPLES

In some embodiments in accordance with the present technology (example A1), a scent delivery system includes a cap removably attachable to a drinking container at an opening of the drinking container, the cap including a mechanism to move between an open position that allows fluid within the drinking container to flow outward and a closed position that prevents the fluid to flow outward; and a scented article that couples to the cap and operable to generate a scent capable of stimulating an olfactory sensation of a user including during consumption of the fluid when the cap is in the open position, wherein, when in the cap is in closed position, a seal is created by the cap to enclose the scented article and lock in the scent.

In some embodiments in accordance with the present technology (example A2), a cap for providing a scent delivery system to a beverage container includes a fixed base including a hole through which the beverage can pour; a movable portion mounted on the fixed base so that the movable portion moves between a closed position that seals the hole and an open position that unseals the hole; an attachment assembly including a first inner wall and a first outer wall capable to dispose a scented article between them so that a portion of the scented article is exposed to air when the movable portion is in the open position; and a receiving assembly including a second inner wall and a second outer wall, wherein, when in the movable portion is in closed position, the first inner wall is in contact with the second inner wall, and the first outer wall is in contact with the second outer wall to create a contact seal around the scented article.

In some embodiments in accordance with the present technology (example A3), a scent delivery system includes a lid removably attachable to a drinking container at an opening of the drinking container, the lid including a mechanism to move between an open position that allows fluid within the drinking container to flow outward and a closed position that prevents the fluid to flow outward; and a scented article that couples to the lid and operable to generate a scent capable of stimulating an olfactory sensation of a user including during consumption of the fluid when the mechanism is in the open position, wherein, when in the mechanism is in closed position, a seal is created to enclose the scented article and lock in the scent.

In some embodiments in accordance with the present technology (example A4), a scent delivery system includes a straw removably attachable to a drinking container at an opening of the drinking container, the lid including a mechanism to couple a scented article to the straw and move between an open position that allows a scent to emanate therefrom and a closed position that creates a seal to lock in the scent, wherein the scent is capable of stimulating an olfactory sensation of a user including during consumption of the fluid when the mechanism is in the open position.

In some embodiments in accordance with the present technology (example B1), a scent delivery system for a beverage includes a cap attachable to a beverage container proximate an opening of the beverage container to cover the opening, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a fixed base including a hole through which the liquid can flow out from, a movable component coupled to the fixed base such that the movable component is able to move with respect to the fixed base between a first position to block the hole and put the cap in the closed position and a second position to unblock the hole and put the cap in the open position, and a scent chamber comprising a first encasement and a second encasement, wherein the first encasement includes a first inner wall and a first outer wall that form a first channel between them, wherein the second encasement includes a second inner wall and a second outer wall that form a second channel between them, wherein the first encasement is configured to attach the scented article to one or both of the first inner wall and the first outer wall such that the scented article is disposed in the first channel so that a portion of the scented article is exposed to air when the movable component is in the second position, and wherein the second encasement is positioned to align with the first encasement such that, when the movable component is in first position, (i) the first inner wall is in contact with the second inner wall and (ii) the first outer wall is in contact with the second outer wall to create a contact seal around the scented article, wherein, when the cap is in closed position, the contact seal created by the cap encloses the scented article and locks in the scent.

Example B2 includes the scent delivery system of any of the preceding or subsequent examples B1-B27, wherein the first encasement of the scent chamber is coupled to the movable component, and the second encasement of the scent chamber is coupled to the fixed base.

Example B3 includes the scent delivery system of example B2 or any of the preceding or subsequent examples B1-B27, wherein the first encasement is coupled to a peripheral wall of the movable component.

Example B4 includes the scent delivery system of example B2 or any of the preceding or subsequent examples B1-B27, wherein the first inner wall and the first outer wall of the first encasement have a height with respect to a trough of the first channel that is less than a height of the scented article such that the scented article protrudes out of the first channel.

Example B5 includes the scent delivery system of any of the preceding or subsequent examples B1-B27, wherein the second encasement of the scent chamber is coupled to the movable component, and the first encasement of the scent chamber is coupled to the fixed base.

Example B6 includes the scent delivery system of example B5 or any of the preceding or subsequent examples B1-B27, wherein the first encasement is disposed on a surface of the fixed base.

Example B7 includes the scent delivery system of example B5 or any of the preceding or subsequent examples B1-B27, wherein the first inner wall and the first outer wall of the first encasement have a height with respect to a trough of the first channel that is less than a height of the scented article such that the scented article protrudes out of the first channel.

Example B8 includes the scent delivery system of any of the preceding or subsequent examples B1-B27, wherein the movable component includes a shaft and an outer wall that spans outward and downward such that the movable component forms an enclosable space with the fixed base, such that the enclosable space is enclosed when the movable component is in the first position, and wherein the scent chamber is contained within at least a portion of the enclosable space between the movable component and the fixed base.

Example B9 includes the scent delivery system of example B8 or any of the preceding or subsequent examples B1-B27, wherein the first encasement is coupled to a peripheral wall of the movable component.

Example B10 includes the scent delivery system of example B8 or any of the preceding or subsequent examples B1-B27, wherein the first encasement is coupled to an interior wall of the movable component.

Example B11 includes the scent delivery system of example B8 or any of the preceding or subsequent examples B1-B27, wherein the first encasement is disposed on a surface of the fixed base.

Example B12 includes the scent delivery system of any of the preceding or subsequent examples B1-B27, wherein the first encasement of the scent chamber includes a curved geometry spanning around the movable component of the cap.

Example B13 includes the scent delivery system of any of the preceding or subsequent examples B1-B27, wherein the first encasement of the scent chamber includes a curved geometry partially spanning around a portion of the movable component of the cap.

Example B14 includes the scent delivery system of any of the preceding or subsequent examples B1-B27, wherein at least one of the first inner wall, the second inner wall, the first outer wall, or the second outer wall includes a material to mechanically compress against an interfacing surface of a corresponding wall to create the contact seal when the cap is in the closed position.

Example B15 includes the scent delivery system of any of the preceding or subsequent examples B1-B27, wherein at least one of the first inner wall, the second inner wall, the first outer wall, or the second outer wall includes an additional lip of material on a contacting surface to contact against an interfacing surface of a corresponding wall to create the contact seal when the cap is in the closed position.

Example B16 includes the scent delivery system of any of the preceding or subsequent examples B1-B27, wherein the first encasement or the second encasement includes an O-ring to contact against an interfacing surface of a corresponding wall to create the contact seal when the cap is in the closed position.

Example B17 includes the scent delivery system of any of the preceding or subsequent examples B1-B27, wherein the fixed base includes a cylinder and a plug.

Example B18 includes the scent delivery system of example B17 or any of the preceding or subsequent examples B1-B27, wherein the movable component is moveably coupled to the cylinder and operable to move bidirectionally by sliding up and down with respect to the cylinder.

Example B19 includes the scent delivery system of example B17 or any of the preceding or subsequent examples B1-B27, wherein the movable component is moveably coupled to the cylinder and operable to rotate with respect to the cylinder along a threading or projection on the cylinder.

Example B20 includes the scent delivery system of any of the preceding or subsequent examples B1-B27, wherein the scented article includes a ring.

Example B21 includes the scent delivery system of any of the preceding or subsequent examples B1-B27, wherein the scented article includes at least a portion of a ring.

Example B22 includes the scent delivery system of any of the preceding or subsequent examples B1-B27, wherein the scented article includes one or more cavities along at least one side surface of the scented article, and wherein the first channel includes one or more projections along at least one corresponding side surface of the first channel, such that the one or more projections of the first channel align with and fit within the one or more cavities of the scented article when the scented article is attached to the first channel.

Example B23 includes the scent delivery system of any of the preceding or subsequent examples B1-B27, wherein the scented article includes one or more projections along at least one side surface of the scented article, and wherein the first channel includes one or more cavities along at least one corresponding side surface of the first channel, such that the one or more projections of the scented article align with and fit within the one or more cavities of the first channel when the scented article is attached to the first channel.

Example B24 includes the scent delivery system of any of the preceding or subsequent examples B1-B27, wherein the scented article includes one or more projections along a side surface of the scented article directed at the first inner wall or the first outer wall, and wherein one or both of the first inner wall and the first outer wall includes a lip that projects out into the first channel at a location closer to an aperture of the first channel than the one or more projections of the scented article to retain the scented article within the first channel.

Example B25 includes the scent delivery system of any of the preceding or subsequent examples B1-B27, wherein the scent delivery system is operable to repeatedly trap the scent generated by the scented article in the scent chamber and release the scent to an outer environment from the cap over a plurality of instances where a user moves the cap between the closed position and the open position.

Example B26 includes the scent delivery system of any of the preceding or subsequent examples B1-B27, wherein the beverage container includes a sports bottle and the cap includes a nipple-type spout.

Example B27 includes the scent delivery system of any of the preceding or subsequent examples B1-B27, wherein the cap includes a sealable flip-cap spout or a sealable straw-type spout.

In some embodiments in accordance with the present technology (example B28), a scent delivery system for a beverage includes a cap attachable to a beverage container proximate an opening of the beverage container to cover the opening, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a fixed base including a hole through which the liquid can flow out from, a movable component coupled to the fixed base such that the movable component is able to move with respect to the fixed base between a first position to block the hole and put the cap in the closed position and a second position to unblock the hole and put the cap in the open position, the movable component including a shaft and an outer wall that spans outward and downward such that the movable component forms an enclosable space with the fixed base, such that the enclosable space is enclosed when the movable component is in the first position, and a scent chamber contained within at least a portion of the enclosable space between the movable component and the fixed base, wherein the scented article is attached to the movable component or to the fixed based, such that a portion of the scented article is exposed to air from an outside environment with respect to the cap when the movable component is in the second position, wherein, when the movable component is in first position, the outer wall of the movable component is in contact with the fixed base to create a contact seal to enclose the scented article within the scent chamber and lock in the scent.

Example B29 includes the scent delivery system of any of the preceding or subsequent examples B28-B35, wherein at least one of the outer wall or the fixed base includes a material to mechanically compress against a corresponding surface when the movable component is in the first position to create the contact seal when the cap is in the closed position.

Example B30 includes the scent delivery system of any of the preceding or subsequent examples B28-B35, wherein at least one of the outer wall or the fixed base includes an additional lip of material on a contacting surface to contact against a corresponding surface when the movable component is in the first position to create the contact seal when the cap is in the closed position.

Example B31 includes the scent delivery system of any of the preceding or subsequent examples B28-B35, wherein at least one of the outer wall or the fixed base includes an O-ring to contact against a corresponding surface to create the contact seal when the movable component is in the first position when the cap is in the closed position.

Example B32 includes the scent delivery system of any of the preceding or subsequent examples B28-B35, wherein the fixed base includes an interior cylinder, and wherein the shaft of the movable component is moveably coupled to the interior cylinder and operable to rotate with respect to the interior cylinder along a threading or projection on the interior cylinder.

Example B33 includes the scent delivery system of any of the preceding or subsequent examples B28-B35, wherein the scented article includes a ring.

Example B34 includes the scent delivery system of any of the preceding or subsequent examples B28-B35, wherein the scented article includes at least a portion of a ring.

Example B35 includes the scent delivery system of any of the preceding or subsequent examples B28-B35, wherein the beverage container includes a sports bottle and the cap includes a nipple-type spout, or wherein the beverage container includes a sealable flip-cap spout.

In some embodiments in accordance with the present technology (example B36), a scent delivery system for a beverage includes a straw removably attachable to a drinking container proximate a hole of the drinking container, the straw operable to allow a liquid contained within the drinking container to flow through the straw and out of an opening of the straw when suction is applied to the opening; and a scented article coupled to an exterior surface of the straw and operable to generate a scent capable of stimulating an olfactory sensation of a user including during consumption of the liquid when the cap is in the open position, the straw including a cover disposed on an outside region of the straw and able to move between a first position that fully covers the scented article and a second position that at least partially exposes the scented article to allow the scent to emanate therefrom.

Example B37 includes the scent delivery system of any of the preceding or subsequent examples B36-B42, comprising a locking assembly that includes one or more cavities disposed on the external surface of the straw proximate the scented article, and one or more protrusions disposed on an interior surface of the cover proximate an end of the cover configured to cover the scented article, wherein the one or more protrusions are structured to fit within the one or more cavities, wherein, when the cover is in first position, the one or more protrusions on the cover are disposed within the one or more cavities on the straw to create a contact seal to enclose the scented article underneath the cover and lock in the scent.

Example B38 includes the scent delivery system of any of the preceding or subsequent examples B36-B42, comprising a locking assembly that includes one or more protrusions disposed on the external surface of the straw proximate the scented article, and one or more cavities disposed on an interior surface of the cover proximate an end of the cover configured to cover the scented article, wherein the one or more protrusions are structured to fit within the one or more cavities, wherein, when the cover is in first position, the one or more protrusions on the straw are disposed within the one or more cavities on the cover to create a contact seal to enclose the scented article underneath the cover and lock in the scent.

Example B39 includes the scent delivery system of any of the preceding or subsequent examples B36-B42, wherein the straw includes an inner straw, and the cover includes an outer straw having an inner diameter greater than an outer diameter of the inner straw.

Example B40 includes the scent delivery system of any of the preceding or subsequent examples B36-B42, wherein the scented article includes a ring that wraps around the circumference of the straw.

Example B41 includes the scent delivery system of any of the preceding or subsequent examples B36-B42, wherein the scented article includes at least a portion of a ring.

Example B42 includes the scent delivery system of any of the preceding or subsequent examples B36-B42, wherein the scented article is positioned from the opening of the straw between 0.5 inches to 2 inches away from the opening.

In some embodiments in accordance with the present technology (example B43), a scent delivery system for a beverage includes a pop-top lid attached to a top surface of a beverage container proximate an opening of the beverage container that is initially covered by a cover, the pop-top lid operable to move with respect to the top surface of the beverage container, wherein the pop-top lid is in an initial position when the cover covers the opening, and wherein the pop-top lid is movable to a second position to cause the opening to be at least partially uncovered by the cover; a scented article operable to generate a scent capable of stimulating an olfactory sensation of a user including during consumption of the liquid; and a scent chamber including an encasement to which the scented article is attached, the encasement coupled to the pop-top lid or the top surface of the beverage container, wherein a portion of the scented article is exposed to air from an outside environment with respect to the scent chamber when the pop-top lid has been moved from the initial position to the second position, and wherein the encasement creates an initial contact seal to enclose the scented article within the scent chamber and lock in the scent when the pop-top lid is in the initial position.

Example B44 includes the scent delivery system of any of the preceding or subsequent examples B43-46, wherein the encasement includes a sleeve.

Example B45 includes the scent delivery system of any of the preceding or subsequent examples B43-46, wherein the pop-top lid includes a finger ring, and the encasement includes a portion of the finger ring proximate an aperture in the finger ring that is bent over a portion of the scented article to allow a remaining portion exposed, such that the finger ring is pressed against the top surface of the beverage container when the pop-top lid is in the initial position to trap the scent.

Example B46 includes the scent delivery system of any of the preceding or subsequent examples B43-46, wherein the scented article is surrounded by the encasement, and the encasement includes a wall to form a channel in which the scented article is contained within.

In some embodiments in accordance with the present technology (example B47), a scent delivery system for a beverage includes a cap attachable to a beverage container proximate an opening of the beverage container to cover the opening into the beverage container, the cap operable to move, reversibly, between a closed position that prevents a liquid contained within the beverage container to flow outward from the beverage container and an open position that allows the liquid within the beverage container to flow outward while the cap is attached to the beverage container; and a scented article that couples to the cap and operable to generate a scent capable of stimulating an olfactory sensation of a user including during consumption of the liquid when the cap is in the open position, wherein the cap comprises: a base, a movable component coupled to the base such that the movable component is able to move with respect to the base between a first position and a second position, and a scent chamber including an encasement to which the scented article is attached, the encasement coupled to the movable component or the base, wherein a portion of the scented article is exposed to air from an outside environment with respect to the cap when the movable component is in the second position, and wherein the encasement creates a contact seal to enclose the scented article within the scent chamber and lock in the scent when the movable component is in the first position.

Example B44 includes the scent delivery system of example B47, which includes one or more features described in any of examples B1-B46.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A scent delivery system for a beverage, comprising:
    a cap reversibly attachable to a beverage container to cover an opening of the beverage container able to contain a liquid;
    an outer cap cover attachable to the cap or to the beverage container and operable to move, reversibly, between a closed position that prevents the liquid contained within the beverage container to be dispensed and an open position that allows the liquid within the beverage container to flow outward from the beverage container through the cap; and
    a scented article operable to generate a scent capable of stimulating an olfactory sensation of a user including during consumption of the liquid,
    wherein the cap comprises:
        a fixed base including a hole through which the liquid can flow out from,
        a movable component coupled to the fixed base such that the movable component is able to move between a first position and a second position, and
        a scent chamber comprising a first encasement and a second encasement, wherein the first encasement includes a first inner wall and a first outer wall that form a first channel between them, wherein the second encasement includes a second inner wall and a second outer wall that form a second channel between them, wherein the first encasement is configured to attach the scented article to one or both of the first inner wall and the first outer wall such that the scented article is disposed in the first channel so that a portion of the scented article is exposed to air when the movable component is in the second position, and wherein the second encasement is positioned to align with the first encasement such that, when the movable component is in the first position, (i) the first inner wall is in contact with the second inner wall and (ii) the first outer wall is in contact with the second outer wall to create a contact seal around the scented article,
    wherein the first encasement of the scent chamber is coupled to the movable component, and the second encasement of the scent chamber is coupled to the fixed base, wherein the first encasement is coupled to a peripheral wall of the movable component.

2. The scent delivery system of claim 1, wherein the first inner wall and the first outer wall of the first encasement have a height with respect to a trough of the first channel that is less than a height of the scented article such that the scented article protrudes out of the first channel.

3. The scent delivery system of claim 1, wherein the first inner wall and the first outer wall of the first encasement have a height with respect to a trough of the first channel that is less than a height of the scented article such that the scented article protrudes out of the first channel.

4. The scent delivery device of claim 1, wherein at least one of the first inner wall, the second inner wall, the first outer wall, or the second outer wall includes a material to mechanically compress against an interfacing surface of a corresponding wall.

5. The scent delivery device of claim 1, wherein at least one of the first inner wall, the second inner wall, the first outer wall, or the second outer wall includes an additional lip of material on a contacting surface to contact against an interfacing surface of a corresponding wall.

6. The scent delivery system of claim 1, wherein the scented article includes a ring, or wherein the scented article includes at least a portion of a ring.

7. The scent delivery system of claim 1, wherein the scent delivery system is operable to repeatedly trap the scent generated by the scented article in the scent chamber and release the scent to an outer environment from the cap over a plurality of instances where a user moves the outer cap cover between the closed position and the open position.

8. The scent delivery system of claim 1, wherein the beverage container includes a sports bottle and the cap includes a nipple-type spout, or wherein the cap includes a sealable flip-cap spout, or wherein the cap includes a sealable straw-type spout.

9. A scent delivery system for a beverage, comprising:
a cap reversibly attachable to a beverage container to cover an opening of the beverage container able to contain a liquid;
an outer cap cover attachable to the cap or to the beverage container and operable to move, reversibly, between a closed position that prevents the liquid contained within the beverage container to be dispensed and an open position that allows the liquid within the beverage container to flow outward from the beverage container through the cap; and
a scented article operable to generate a scent capable of stimulating an olfactory sensation of a user including during consumption of the liquid,
wherein the cap comprises:
a fixed base including a hole through which the liquid can flow out from,
a movable component coupled to the fixed base such that the movable component is able to move between a first position and a second position, and
a scent chamber comprising a first encasement and a second encasement, wherein the first encasement includes a first inner wall and a first outer wall that form a first channel between them, wherein the second encasement includes a second inner wall and a second outer wall that form a second channel between them, wherein the first encasement is configured to attach the scented article to one or both of the first inner wall and the first outer wall such that the scented article is disposed in the first channel so that a portion of the scented article is exposed to air when the movable component is in the second position, and wherein the second encasement is positioned to align with the first encasement such that, when the movable component is in the first position, (i) the first inner wall is in contact with the second inner wall and (ii) the first outer wall is in contact with the second outer wall to create a contact seal around the scented article,
wherein the movable component includes a shaft and an outer wall that spans outward and downward such that the movable component forms an enclosable space with the fixed base, such that the enclosable space is enclosed when the movable component is in the first position, and wherein the scent chamber is contained within at least a portion of the enclosable space between the movable component and the fixed base.

10. The scent delivery system of claim 9, wherein the first encasement is coupled to the movable component.

11. The scent delivery system of claim 9, wherein the first encasement is coupled to the fixed base.

12. The scent delivery system of claim 9, wherein the scented article includes a ring, or wherein the scented article includes at least a portion of a ring.

13. A scent delivery system for a beverage, comprising:
a cap reversibly attachable to a beverage container to cover an opening of the beverage container able to contain a liquid;
an outer cap cover attachable to the cap or to the beverage container and operable to move, reversibly, between a closed position that prevents the liquid contained within the beverage container to be dispensed and an open position that allows the liquid within the beverage container to flow outward from the beverage container through the cap; and
a scented article operable to generate a scent capable of stimulating an olfactory sensation of a user including during consumption of the liquid,
wherein the cap comprises:
a fixed base including a hole through which the liquid can flow out from,
a movable component coupled to the fixed base such that the movable component is able to move between a first position and a second position, and
a scent chamber comprising a first encasement and a second encasement, wherein the first encasement includes a first inner wall and a first outer wall that form a first channel between them, wherein the second encasement includes a second inner wall and a second outer wall that form a second channel between them, wherein the first encasement is configured to attach the scented article to one or both of the first inner wall and the first outer wall such that the scented article is disposed in the first channel so that a portion of the scented article is exposed to air when the movable component is in the second position, and wherein the second encasement is positioned to align with the first encasement such that, when the movable component is in the first position, (i) the first inner wall is in contact with the second inner wall and (ii) the first outer wall is in contact with the second outer wall to create a contact seal around the scented article,
wherein the scented article includes one or more cavities along at least one side surface of the scented article, and wherein the first channel includes one or more projections along at least one corresponding side surface of the first channel, such that the one or more projections of the first channel align with and fit within the one or more cavities of the scented article when the scented article is attached to the first channel, or wherein the scented article includes one or more projections along at least one side surface of the scented article, and wherein the first channel includes one or more cavities along at least one corresponding side surface of the first channel, such that the one or more projections of the scented article align with and fit within the one or more cavities of the first channel when the scented article is attached to the first channel.

14. The scent delivery system of claim 13, wherein the scented article includes a ring, or wherein the scented article includes at least a portion of a ring.

15. A scent delivery system for a beverage, comprising:
a cap attachable to a beverage container to cover an opening of the beverage container able to contain a liquid;
an outer cap cover reversibly attachable to the cap and operable to move between a closed position that prevents the liquid contained within the beverage container to be dispensed and an open position that allows the liquid within the beverage container to flow outward from the beverage container through the cap; and
a scented article operable to generate a scent capable of stimulating an olfactory sensation of a user including during consumption of the liquid,
wherein the cap comprises:
a base including a first aperture and a second aperture through which the liquid from the beverage container can flow out from,
a movable component reversibly coupled to the base such that the movable component is able to attach and detach with respect to the base, and
a scent chamber configured in the movable component and comprising an encasement structure, wherein the encasement structure includes a bottom wall, an inner side wall, and an outer side wall that form a channel between them, wherein the encasement structure is configured to attach the scented article to one or both of the inner side wall and the outer side wall such that the scented article is disposed in the channel so that a portion of the scented article is exposed to air, and wherein the outer cap cover is configured to attach to the base of the cap in the closed position such that a space surrounding an exposed region of the scented article is encased between the movable component and the outer cap cover to create a contact seal around the space surrounding the scented article, wherein the scented article includes one or more cavities along at least one side surface of the scented article, and wherein the channel includes one or more corresponding projections along the inner side wall of the encasement structure, such that the one or more corresponding projections align with and fit within the one or more cavities of the scented article when the scented article is disposed in the channel.

16. The scent delivery system of claim 15, wherein the scent delivery system is operable to repeatedly trap the scent generated by the scented article in the scent chamber and release the scent to an outer environment from the cap over a plurality of instances where the user moves the outer cap cover between the closed position and the open position.

17. The scent delivery system of claim 15, wherein the inner side wall and the outer side wall of the encasement structure have a height with respect to a trough of the channel that is less than a height of the scented article such that the scented article protrudes out of the channel.

18. The scent delivery system of claim 15, wherein the movable component includes a shaft that spans outward from the inner side wall of the first channel such that the shaft is enclosed when the outer cap cover is in the closed position.

19. The scent delivery system of claim 15, wherein the scented article includes a ring, or wherein the scented article includes at least a portion of a ring.

* * * * *

UNITED STATES PATENT AND TRADEMARK OFFICE
CERTIFICATE OF CORRECTION

| | | |
|---|---|---|
| PATENT NO. | : 12,202,662 B2 | Page 1 of 1 |
| APPLICATION NO. | : 18/185357 | |
| DATED | : January 21, 2025 | |
| INVENTOR(S) | : Shawn Griffis | |

It is certified that error appears in the above-identified patent and that said Letters Patent is hereby corrected as shown below:

On the Title Page

On the page 5, in Column 2, item (56) under "Other Publications", Line 21, delete "Recived" and insert -- Received --.

On the page 6, in Column 2, item (56) under "Other Publications", Line 6, delete "retai l" and insert -- retail --.

On the page 6, in Column 2, item (56) under "Other Publications", Line 12, delete "retreived" and insert -- retrieved --.

In the Specification

In Column 12, Line 22, delete "in in" and insert -- is in --.

In Column 13, Line 33, delete "in in" and insert -- is in --.

In Column 24, Line 6, delete "and," and insert -- —and, --.

In the Claims

In Column 33, Line 13, delete "delivery device of" and insert -- delivery system of --.

In Column 33, Line 18, delete "delivery device of" and insert -- delivery system of --.

Signed and Sealed this
Eighth Day of April, 2025

Coke Morgan Stewart
*Acting Director of the United States Patent and Trademark Office*